United States Patent
Firestone et al.

(12) 
(10) Patent No.: US 6,214,345 B1
(45) Date of Patent: *Apr. 10, 2001

(54) LYSOSOMAL ENZYME-CLEAVABLE ANTITUMOR DRUG CONJUGATES

(75) Inventors: Raymond Armand Firestone, New Haven; Gene Michael Dubowchik, Middlefield, both of CT (US)

(73) Assignee: Bristol-Myers Squibb Co., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 08/062,366

(22) Filed: May 14, 1993

(51) Int. Cl.$^7$ ................................................. A61K 39/40

(52) U.S. Cl. .................................. 424/178.1; 530/391.7; 530/391.9

(58) Field of Search ............................. 530/391.7, 391.9, 530/351; 424/178.1, 179.1, 181.1, 184.1

(56) References Cited

U.S. PATENT DOCUMENTS

| | | | |
|---|---|---|---|
| 4,543,211 | * 9/1985 | Kato et al. ........................ | 530/391.9 |
| 4,671,958 | * 6/1987 | Rodwell et al. .................. | 424/85.91 |
| 4,867,973 | 9/1989 | Goers et al. ...................... | 424/85.91 |
| 5,013,547 | * 5/1991 | Sweet et al. ...................... | 424/85.91 |
| 5,045,451 | * 9/1991 | Uhr et al. .......................... | 435/7.23 |
| 5,057,301 | 10/1991 | Wilbur et al. .................... | 424/1.1 |
| 5,057,313 | 10/1991 | Shih et al. ........................ | 424/85.91 |
| 5,087,616 | 2/1992 | Myers et al. ..................... | 514/21 |
| 5,094,849 | 3/1992 | Cullinan et al. ................. | 424/85.91 |
| 5,106,951 | * 4/1992 | Morgan et al. ................... | 530/391.9 |
| 5,144,012 | 9/1992 | Johnson et al. .................. | 530/391.9 |
| 5,155,210 | 10/1992 | Wrasidlo .......................... | 530/317 |
| 5,169,933 | 12/1992 | Anderson et al. ................ | 424/1.1 |
| 5,198,560 | 3/1993 | Kadow et al. ..................... | 556/142 |
| 5,208,020 | 5/1993 | Chari et al. ....................... | 424/85.91 |

FOREIGN PATENT DOCUMENTS

| | | | |
|---|---|---|---|
| 0554 708 A1 | 8/1993 | (EP) | ............................ A61K/47/48 |
| WO 81/01145 | 4/1981 | (WO) | .................................. 103/52 |
| WO 88/00837 | 2/1988 | (WO) | ......................... A61K/47/00 |
| WO 90/03188 | 4/1990 | (WO) | ......................... A61K/43/00 |
| WO 90/03401 | 4/1990 | (WO) | .......................... C07K/17/00 |

OTHER PUBLICATIONS

Borrebaeck, Journal of Immunological Methods, vol. 123, pp. 157–165 (1989).*
Waldmann, Science, vol. 252, pp. 1657–1662 (1991).*
Osband et al., Immunology Today, vol. 11, No. 6, pp. 193–195 (1990).*
Hermentin et al., Behring Inst. Mitt. No. 82, pp. 197–215 (1988).*
Seaver, Genetic Engineering News, pp. 10 and 21, 1994.*
Harris et al., TIBTECH, vol. 11, pp. 42–44, (1993).*
Allen, Ann. Rep. in Med. Chem. "Section VI–Topics in Chemistry and Drug Design. Chapter 28, Recent Advances in Drug Delivery System Technology," 1983.
Baurian et al., J. Med. Chem., "Amino Acid and Dipeptide Derivatives of Daunorubicin. 2. Cellular Pharmacology and Antitumor Activity on L1210 Leukemic Cells in vitro and in vivo." 23: 1171–1174, 1980.
Bounkhala et al., J. Med. Chem. "Coupling Products of Amino Acids to Penicillin V and Cephalothin: Synthesis and Susceptibility to Carboxypeptidases and Lysosomal Enzymes," 31: 976–983, 1988.
Bruesch et al., Int. J. Cancer, "Plasminogen Activator in Normal and Tumor–bearing Mice," 32: 121–126, 1983.

(List continued on next page.)

Primary Examiner—Ponnathapura Achutamurthy
(74) Attorney, Agent, or Firm—James M. Bogden; Thomas R. Savitsky; Audrey F. Sher

(57) ABSTRACT

The present invention relates to drug-ligand conjugates wherein the drug is linked to the ligand through a protein peptide linker and a connector, a process for the preparation of the conjugates, method of controlling the growth of undesirable cells, pharmaceutical compositions, and intermediates thereof.

258 Claims, 2 Drawing Sheets

OTHER PUBLICATIONS

Canal et al., *Clin, Pharmacol. Ther.*, Human Pharmacokinetics of N–L–leucyl–doxorubicin, a New Anthracycline Derivative, and its Correlation with Clinical Toxicities, 51: 249, 1992.

Carl et al., *Proc. Nat'l Acad. Sci.*, "Protease–activated "prodrugs" for cancer chemotherapy," 78: 2224–2228, 1980.

Chakravarty et al., *J. Amer. Chem. Soc.*, "Plasmin–Activated Prodrugs for Cancer Chemotherapy. 2. Synthesis and Biological Activity of Peptidyl Derivatives of Doxorubicin," 26 (5): 638–643, 1983.

Chakravarty et al., *J. Med. Chem.*, "Plasmin–Activated Prodrugs for Cancer Chemotherapy. 1. Synthesis and Biological Activity of Peptidylacivicin and Peptidylphenylenediamine Mustard," 26: 633–638, 1983.

Carl et al., *J. of Med. Chem.*, "A Novel Connector Linkage Applicable in Prodrug Design," 24 (5): 479, 1981.

Duncan et al., *Biochem. and Biophys. Res. Comm.*, "Degradation of Side Chains of N–(2–Hydroxypropl)Methacrylamide Copolymers by Lysosomal Enzymes," 94: (1), 1980.

Duncan et al., *Biosci. Rep.*, "Degradation of side–chains of N–(2–hydroxypropyl)methacrylamide copolymers by lysosomal thiol–proteinases," 2: 1041–1046, 1982.

Duncan et al., *Br. J. Cancer*, "Anticancer agents coupled to N–(2–hydorxypropyl)methacrylamide copolymers. I. Evaluation of daunomycin conjugated in vivo against L1210 leukaemia," 57: 147, 1988.

Rejmanova et al., *Makromol. Chem.*, "Degradation of Oligopeptide Sequences in N–(2–hydroxypropyl)methacryalmide copolymers by Bovine Spleen Cathespin B," 184: 2009–2220, 1983.

Firestone et al., *J. Med. Chem.*, "Lysosomotropic Agent. 4. Carbobenzoxglycylphenylalanyl, a New Protease–Sensitive Masking Group for Introduction into Cells," 25: 539–544, 1982.

Chakrabarti, *Chem. and Ind.*, "Synthesis of Potentially Cytoactive Peptide Mustards," 898, 1965.

Kingsbury et al., *J. Med. Chem.*, A Novel Peptide Delivery System Involving Peptidase Activated Prodrugs as Antimicrobial Agents. Synthesis and Biological Activity of Peptidyl Derivatives of 5–Fluorouacil, 17: 1447–1451, 1984.

Kohn et al., *Analytical Biochem.*, "A Peptidyl Derivative of [$^3$H]Aniline as a Sensitive, Stable, Protease Substrate," 97: 269–276, 1979.

Law et al., *Anticancer Research*, Tumor Reactive cis–Aconitylated Monoclonal Antibodies Coupled to Daunorubicin through a Peptide Spacer are Unable to Kill Tumor Cells, 10: 845–852, 1990.

Levin and Sela, *Febs. Letters*, "Studies on Amino Acid and Peptide Derivatives of Daunorubicine," 98: (1), 119–122, 1979.

Magnan et al., *J. Med. Chem.*, "Drug Latentiation by γ–Glutamyl Transpeptidase," 25: 1018–1021, 1982.

Masquelier et al., *J. Med. Chem.* "Amino Acid and Dipeptide Derivatives of Daunorubicin. 1. Synthesis, Physicochemical Properties, and Lysosomal Digestion," 23: 1166–1170, 1980.

Mitchell et al., *J. Chem. Soc.*, "Prodrugs of Phosphonoformate: Products, Kinetics and Mechanisms of Hydrolysis of Dibenzyl (methoxycarbonyl)phosphonate," 1297, 1991.

Payne, *Drugs Exptl. Res.*, "Drug Delivery Systems: Optimizing the Structure of Peptide Carriers for Synthetic Antimicrobial Drugs," XII(6/7): 585–594, 1986.

Ponpipom et al., *Amer. Chem. Soc.*, "Cell–Specific Ligands for Selective Drug Delivery to Tissues and Organs," 24: 1388–1395, 1981.

Renard et al., *J. Med. Chem.*, "Hydrolysis of Pro–Ala Dipeptides by Lysosomal Hydrolases. Models for the Study of Lysosomotropic Amino Acid Prodrugs of Penicillins," 29: 1291–1293, 1986.

Ringrose, *Biochem. Soc. Trans.*, "Small Peptides as Carriers and Targets in Human Therapy," 11:804, 1983.

Ringsdorf et al., *Makromol. Chem.*, "Bis(2–chloroethyl)amine bound to copolymers of N–1(2–hydroxypropyl)methacrylamide and methacryloylated oligopeptides via biodegradable bonds," 188: 257–264, 1987.

Sela and Levin, *Cells*, "Improved Antitumor Activity of Basic Amino Acid and Dipeptide Derivatives of Daunorubicin on E L4 Leukemia Cells in Mice," 65: 277–281, 1981.

Senter et al., *J. Org. Chem.*, "Development of Drug–Release Strategy Based on the Reductive Fragmentation of Benzyl Carbamate Disulfides," 55: 2975–2978, 1990.

Thomas, *Biochem. Soc. Trans.*, "Prodrugs," 383–387, 1986.

Trouet et al., *Topics in Pharm. Sci.*, "Target Oriented Drug Delivery in Cancer Treatment," 153–162, 1981.

Trouet, *Eur. J. Cancer*, "Increased Selectivity of Drugs by Linking to Carriers," 14: 105–111, 1978.

Trouet, *Proc. Natl. Acad. Sci.*, "A Covalent Linkage Between Daunorubicin and Proteins that is Stable in Serum and Reversible by Lysosomal Hydrolases, as Required for a Lysosomotropic Drug–Carrier Conjugate: In vitro and in vivo Studies," 79:626–629, 1982.

Weber et al., *Annals NY Acad. Sci.*, "Plasmin–Activated Anticancer Prodrugs," 397: 324, 1982.

Umemoto, N. et al., "Preparation and In Vitro Cytotocity of a Methotrexate–Anti–MM46 Monoclonal Antibody Conjugate Via an Oligopeptide Spacer" (1989) Int. J. Cancer, 43, 677–684.

Tsukada, Y. et al., "An Anti–α–Fetoprotein Antibody–Daunorubicin Conjugate With a Novel Poly–L–Glutamic Acid Derivative as Intermediated Drug Carrier" (1984) JNCI, 73, 721–729.

\* cited by examiner

| L2987 | 3.9 |

FIG. 1A

| L2987 | 176.7 |

FIG. 1B

| A2780 | 1.6 |

FIG. 1C

| A2780 | 104.8 |

FIG. 1D

| HCT116 | 3.8 |

FIG. 1E

| HCT116 | 3.3 |

FIG. 1F

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:1:

Gly Phe Leu Gly
1

-continued (2) INFORMATION FOR SEQ ID NO:2:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:2:

Ala Leu Ala Leu

LYSOSOMAL ENZYME-CLEAVABLE ANTITUMOR DRUG CONJUGATES

BACKGROUND OF THE INVENTION

1. Field of the Invention

The present invention provides drug-ligand conjugates wherein the ligand is connected to the drug moiety through a peptide linker made up of a protein peptide specifier, a carboxylic acyl unit, and a self-immolating spacer, and which conjugates are activated by lysosomal enzymes.

2. Description of the Art

Bipartate compounds consisting of a carrier or linker moiety and a drug moiety are known. These compounds have been particularly useful in the formation of immuno-conjugates directed against tumor associated antigens. In certain cases, however, bipartate compounds may be unstable due to the inherent nature of the bond linking the antibodies to the drug or due to the electronic or steric features of the drug moiety which may hinder hydrolysis of the bond by the desired target enzyme. Katzenellenbogen, *J. Amer. Chem. Soc.*, (1981) 24: 479–480.

SUMMARY OF THE INVENTION

The present invention provides tumor specific, drug-ligand conjugates composed of a ligand, a drug, and a peptide linker, which conjugate is selectively activatible at the site of the tumor.

The drug-ligand conjugates of this invention comprise at least one drug molecule, a ligand capable of targeting a selected cell population, and a peptide linker which contains a carboxylic acyl, and a protein peptide specifier. The peptide linker may also contain a self-immolating spacer which spaces the protein peptide sequence and the drug.

The ligand is linked to the carboxylic acyl unit via a thioether-containing linker unit arm, which thioether bond is created by reaction of a sulfhydryl group on the ligand. In a preferred embodiment, the targeting ligand is attached directly to the peptide linker through a covalent thioether bond.

An aspect of the present invention provides drug conjugates which are selectively activatible at the site of the tumor.

Another aspect of the invention provides tumor-specific drug conjugates which are highly selective substrates for drug-activating enzymatic cleavage by one or more tumor-associated enzymes.

A further aspect of the invention provides tumor-specific drug conjugates wherein the activating enzyme is one which is present in the tumor in sufficient amounts to generate cytotoxic levels of free drug in the vicinity of the tumor.

Another aspect of the invention provides tumor-specific drug conjugates which tumor specificity arises solely from the ligand.

Another aspect of the invention provides tumor-specific drug conjugates which are stable to adventitious proteases in blood.

A still further aspect of the present invention provides a tumor-specific drug conjugate in accordance with the preceding aspects, which is considerably less toxic than the activated drug.

In another aspect the present invention provides a method for the production of the drug conjugates and pharmaceutical compositions and methods for delivering the conjugates to target cells in which a modification in biological process is desired, such as in the treatment of diseases such as cancer.

The present invention also provides a method for delivering to the site of tumor cells in a warm-blooded animal an active antitumor drug by administering to said warm-blooded animal the drug-ligand conjugate according to this invention.

In one embodiment the drug moiety is an anthracycline antibiotic, the ligand is an antibody, A is a carboxylic acyl unit, Y is Phe, Z is Lys, and n is 5.

In a preferred embodiments the anthracycline drug moiety is doxorubicin, the ligand moiety is a chimeric antibody, A is carboxylic acyl unit, Y is Phe, Z is Lys, and n is 5.

In another preferred embodiment the drug moiety is taxol, the ligand is an antibody, Y is Phe, Z is Lys and n is 5.

In another preferred embodiment the drug moiety is mitomycin C, the ligand is an antibody, Y is Phe, Z is Lys and n is 5.

The above and other aspects of the present invention are achieved by derivatizing an antitumor agent linked to a ligand through a peptide linker, made up of a protein peptide sequence and a self-immolating spacer, at a reactive site appropriate for inhibiting the pharmacological activity of the antitumor agent to thereby convert the antitumor agent into a pharmacologically inactive peptidyl derivative conjugate. The peptide linker has an amino acid residue sequence specifically tailored so as to render the peptidyl derivative a selective substrate for drug-activating enzymatic cleavage by one or more lysosomal proteases, such as cathepsin B, C or D. The enzymatic cleavage reaction will remove the peptide linker moiety from the drug conjugate and effect release of the antitumor agent in pharmacologically active form selectively at the tumor site. In comparison with ligand-drug linkers which rely on simple acid hydrolysis for drug release this new method provides significantly less systemic toxicity due to premature linker hydrolysis in the blood, consequently a greater amount of drug is delivered to the tumor site, and the method results in a longer storage life and simplified handling conditions for the conjugate.

The drug-ligand conjugates of the present invention show significantly less systemic toxicity than biparte conjugates and free drug. The conjugates of the invention retain both specificity and therapeutic drug activity for the treatment of a selected target cell population. They may be used in a pharmaceutical composition, such as one comprising a pharmaceutically effective amount of a compound of Formula (I) below, associated with a pharmaceutically acceptable carrier, diluent or excipient.

BRIEF DESCRIPTION OF THE DRAWINGS

FIGS. 1A and 1B illustrate the expression of the BR96 antigen in the L2987 lung line.

FIGS. 1C and 1D illustrate the expression of the BR96 antigen in the A2780 ovarian line.

FIGS. 1E and 1F illustrate expression of the BR96 antigen in the HCT116 colon line.

DETAILED DESCRIPTION OF THE INVENTION

Figure 2A:
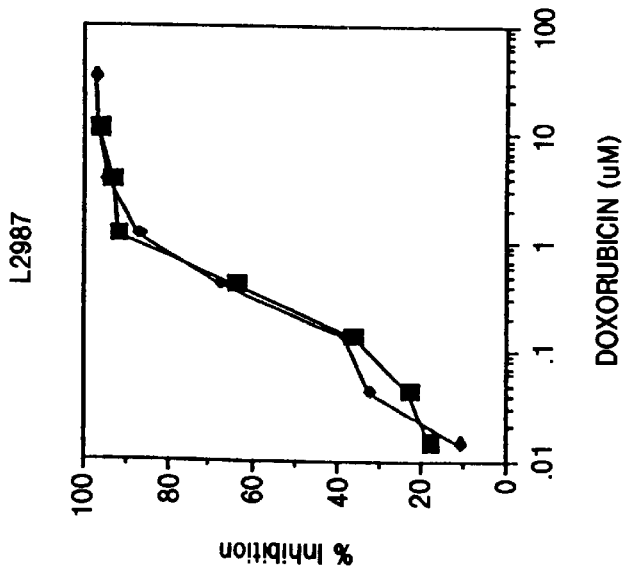
FIG. 2A shows the potency of the BR96-doxorubicin conjugate and the unconjugated doxorubicin in the L2987 lung line.

The following detailed description is provided so that the invention may be more fully understood.

The present invention provides novel drug-ligand conjugates composed of a ligand capable of targeting a selected cell population, and a drug connected to the ligand by a peptide linker. The peptide linker is made up of a carboxylic acyl unit and a protein peptide sequence. The peptide linker may also contain a self-immolating spacer, which spaces the drug and the protein peptide sequence.

The ligand molecule can be an immunoreactive protein such as an antibody, or fragment thereof, a non-immunoreactive protein, or peptide ligand such as bombesin or, a binding ligand recognizing a cell associated receptor such as a lectin, or any protein or peptide that possesses a reactive sulfhydryl group (—SH) or can be modified to contain such a sulfhydryl group. The carboxylic acyl unit is linked to the ligand via a thioether bond, and the drug is linked to the linker via a functional group selected from primary or seconday amine, hydroxyl, sulfhydryl, carboxyl, aldehyde or ketone.

A conjugate of the present invention is represented by general Formula (I):

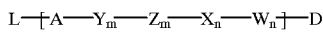

Formula (I)

in which
D is a drug moiety;
L is a ligand;
A is a carboxylic acyl unit
Y is an amino acid;
Z is an amino acid;
X is a self-immolative spacer;
W is a self-immolative spacer;
m is an integer of 1, 2, 3, 4, 5 or 6.
n is an integer of 0 or 1.

For a better understanding of the invention, the drugs, ligands, peptides and spacers will be discussed individually. The synthesis of the conjugates then will be explained.

It will be understood that in the following detailed description and appended claims, the abbreviations and nomenclature employed are those which are standard in amino acid and peptide chemistry, and that all the amino acids referred to are in the L-form unless otherwise specified.

The abbreviations used in the present application, unless otherwise indicated are as follows:

AcOH: acetic acid; Ala: L-alanine; Alloc: allyloxycarbonyl; Arg: L-arginine; Boc: t-butyloxycarbonyl; Cit: L-citrulline; DBU: diazobicycloundecene; DCC: dicyclohexylcarbodiimide; DCI: direct chemical ionization; DCU: dicyclohexylurea; DIEA: diisopropylethylamine; DMAP: 4-dimethylaminopyridine; DME: 1,2-dimethoxyethane; DOX: doxorubicin; DTT: dithiothreitol; EEDQ: N-ethoxycarbonyl-2-ethoxy-1,2-dihydroquinoline; EtOAc: ethyl acetate; FAB: fast atom bombardment; Fmoc: fluorenylmethoxycarbonyl; GABA: γ-aminobutyric acid; Gly: glycine; HOBt: N-hydroxybenzotriazole; HRMS: high resolution mass spectroscopy; LDL: low density lipoprotein; Ile: L-isoleucine; Leu: L-leucine; Lys: L-lysine; MC: 6-maleimidocaproyl; MMA: mitomycin A, MMC: mitomycin C; Mtr: 4-methoxytrityl; NHS: N-hydroxysuccinimide; NMP: N-methylpyrrolidinone; PABC: p-aminobenzyl-carbamoyl; PAB-OH: p-aminobenzyl alcohol; Phe:L-phenylalanine; PNP: p-nitrophenol; TFA: trifluoroacetic acid; THF: tetrahydrofuran; Trp:L-tryptophan; Val: L-valine; Z: benzyloxycarbonyl.

THE PEPTIDE LINKER

The peptide linker of the present invention is made up of a carboxylic acyl unit, and a protein peptide sequence. The linker may also contain a self-immolating spacer which spaces the drug and the protein peptide sequence.

In the conjugate of Formula I, the peptide linker is represented by "A—Y—Z—X—W" in which "A" is the carboxylic acyl unit, "Y" and "Z" are each amino acids and together form the protein peptide sequence, and "X" and "W" are individualy self-immolating spacers which spaces the protein peptide and the drug.

THE PROTEIN PEPTIDE SEQUENCE

In the conjugate of Formula I,

Y is at least one amino acid selected from the group consisting of alanine, valine, leucine, isoleucine, methionine, phenylalanine, tryptophan and proline, preferably phenylalanine or valine; and Z is at least one amino acid selected from the group consisting of lysine, lysine protected with acetyl or formyl, arginine, arginine protected with tosyl or nitro groups, histidine, ornithine, ornithine protected with acetyl or formyl, and citrulline, preferably lysine, or citrulline.

The amino acid residue sequence is specifically tailored so that it will be selectively enzymatically cleaved from the resulting peptidyl derivative drug-conjugate by one or more of the tumor-associated proteases.

The amino acid residue chain length of the peptide linker preferably ranges from that of a dipeptide to that of a tetrapeptide. It will be understood, however, that peptide linkers as long as eight amino acid residues may also suitably be employed.

The following group of exemplary peptide linker groups, are named in order to illustrate further the conjugates of the present invention:

Phe-Lys, Val-Lys, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Gly-Phe-Leu-Gly [SEQ ID NO: 1], Ala-Leu-Ala-Leu [SEQ ID NO:2], Phe-$N^9$-tosyl-Arg, and Phe-$N^9$-Nitro-Arg.

Specific examples of the preferred embodiment of peptide sequences include Phe-Lys, Val-Lys, Val-Cit, and D-Phe-L-Phe-Lys.

Numerous specific peptide linker molecules suitable for use in the present invention can be designed and optimized in their selectivity for enzymatic cleavage by a particular tumor-associated protease. The preferred peptide linkers for use in the present invention are those which are optimized toward the proteases, cathepsin B, C and D. Cathepsin B was shown to release DOX from the conjugate at pH 5.3 (37° C.) with ($t_{1/2}$=3.0 hrs.).

THE SPACER

The drug-conjugates in accordance with the present invention may employ an intermediate self-immolative spacer moiety which spaces and covalently links together the drug moiety and the protein peptide moiety. A self-immolative spacer may be defined as a bifunctional chemical moiety which is capable of covalently linking together two spaced chemical moieties into a normally stable tripartate molecule, releasing one of said spaced chemical moieties from the tripartate molecule by means of enzymatic cleavage; and following said enzymatic cleavage, spontaneously cleaving from the remainder of the molecule to release the other of said spaced chemical moieties. In accordance with the present invention, the self-immolative spacer is covalently linked at one of its ends to the protein peptide moiety and covalently linked at its other end to the chemical reactive site of the drug moiety whose derivatization inhibits pharmacological activity, so as to space and covalently link together the protein peptide moiety and the drug moiety into a tripartate molecule which is stable and pharmacologically inactive in the absence of the target enzyme, but which is enzymatically cleavable by such target enzyme at the bond covalently linking the spacer moiety and the protein peptide moiety to thereby effect release of the protein peptide moiety from the tripartate molecule. Such enzymatic cleavage, in turn, will activate the self-immolating character of the spacer moiety and initiate spontaneous cleavage of the bond covalently linking the spacer moiety to the drug moiety, to thereby effect release of the drug in pharmacologically active form.

In the conjugate of Formula I,

X is a spacer moiety which spaces and covalently links together the drug moiety and the amino acid, in which the spacer is linked to the drug moiety via the T moiety, and which may be represented by the compounds of Formulae (III), (IV), (V) or (VI):

Formula (III)

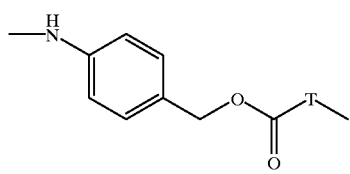

in which T is O, NH, N or S,

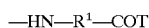

Formula (IV)

in which T is O, NH, N or S, and
$R^1$ is $C_1$–$C_5$ alkyl;

Formula (V)

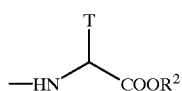

(*J. Med. Chem.*, 27: 1447 (1984))
in which T is O, NH, N or S, and
$R^2$ is H or $C_1$–$C_5$ alkyl, Formula (VI)

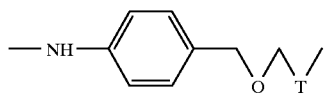

or

W is a spacer moiety represented by the Formula (VII)

Formula (VII)

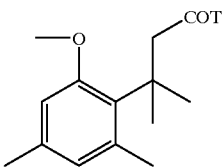

wherein T is O, S or NH, N.

As used herein "$C_1$–$C_5$ alkyl" is meant to include branched or unbranched hydrocarbon chain having, unless otherwise noted, one to five carbon atoms, including but not limited to methyl, ethyl, isopropyl, n-propyl, sec-butyl, isobutyl, n-butyl and the like.

A preferred spacer moiety suitable for use in the present invention is PABC represented by the Formula (IIIa):

Formula (IIIa)

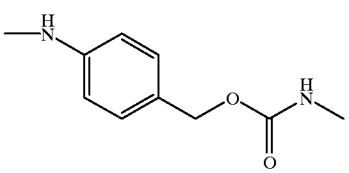

Another preferred spacer moiety suitable for use in the present invention is GABA represented by the Formula (IVa):

Formula (IVa)

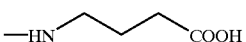

Yet another preferred spacer moiety suitable for use in the present invention is α,α-dimethyl GABA represented by the Formula (IVb):

Formula (IVb)

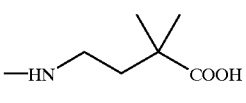

Another preferred spacer moiety suitable for use in the present invention is β,β-dimethyl GABA represented by the Formula (IVc):

THE CARBOXYLIC ACYL UNIT

In the conjugate of Formula (I), the carboxylic unit "A" is linked to the ligand via a sulfur atom derived from the ligand. Representative of conjugates of this invention are compounds of Formulae (IXa), (IXb), (IXc), (IXd) and (IXe), which "A" is the compound in brackets.

Formula (IXa)

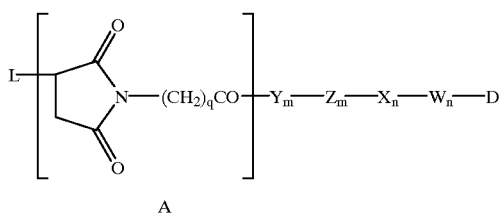

in which q is 1–10, and L, Y, Z, X, W, D, n and m are as previously defined;

Formula (IXb)

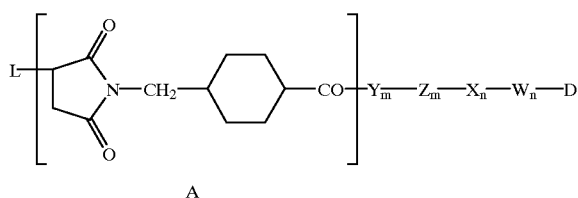

made from succinimidyl 4-(N-maleimidomethyl)-cyclohexane-1-carboxylate (SMCC) (Pierce Catalog p. E-15 (1992)), wherein L, Y, Z, X, W, D, n and m are previouly defined;

Formula (IXc)

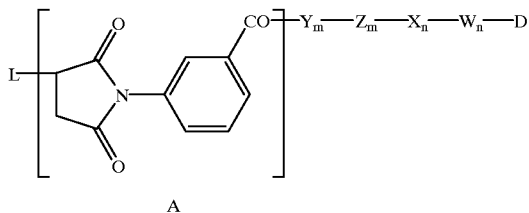

made from m-maleimidobenzoyl-N-hydroxysuccinimide ester (MBS) (Pierce Catalog p. E-16 (1992)), wherein L, Y, Z, X, W, D, n and m are as previously defined;

Formula (IXd)

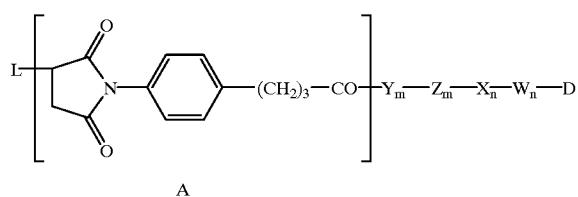

made from succinimidyl 4-(p-maleimidophenyl)butyrate (SMPB) (Pierce catalog p. E-18 (1992)), wherein L, Y, Z, X, W, D, n and m are as previously defined;

Formula (IXe)

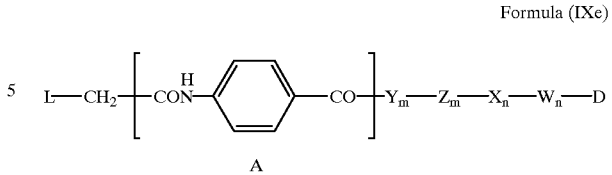

made from N-succinimidyl(4-iodoacetyl)aminobenzoate (SIAB) (Pierce catalog p. E-17 (1992)), wherein L, Y, Z, X, W, D, n and m are as previously defined; or A is a compound that joins up to the peptide and is linked to the ligand via a sulfur atom derived from the ligand, and a sulfur atom derived from the carboxylic acyl unit to form a dithio link. Representative of conjugates of this invention are compounds of Formulae (Xa), (Xb) and (Xc)

Formula (Xa)

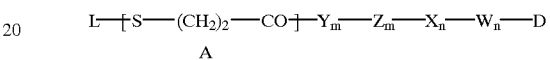

made from N-succinimidyl 3-(2-pyridyldithio)propionate (SPDP) (Pierce catalog p. E-13 (1992)), wherein L, Y, Z, X, W, D, n and m are as previously defined;

Formula (Xb)

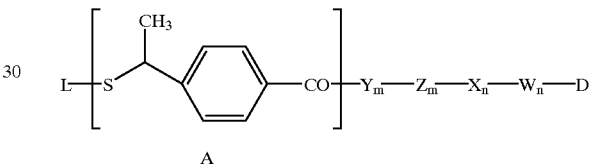

made from 4-succinimidyloxycarbonyl-α-methyl-α-(2-pyridyldithio)-toluene (SMPT) (Pierce catalog p. E-12 (1992)), wherein L, Y, Z, X, W, D, n and m are as previously defined; and Formula (Xc)

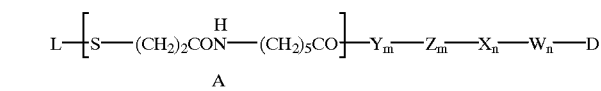

made from long chain SPDP (Pierce catalog p. E-14 (1992), wherein L, Y, Z, X, W, D, n and m are as previously defined.

THE DRUG

The drug conjugates of the present invention are effective for the usual purposes for which the corresponding drugs are effective, and have superior efficacy because of the ability, inherent in the ligand, to transport the drug to the desired cell where it is of particular benefit. Further, because the conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a protein such as tumor necrosis factor.

The preferred drugs for use in the present invention are cytotoxic drugs, particularly those which are used for cancer therapy. Such drugs include, in general, DNA damaging agents, anti-metabolites, natural products and their analogs. Preferred classes of cytotoxic agents include, for example, the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, differentiation inducers, and taxols. Particularly useful members of those classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, carminomycin, aminopterin, tallysomycin, podophyllotoxin and podophyllotoxin derivatives such as etoposide or etoposide phosphate, vinblastine, vincristine, vindesine, taxol, taxotere retinoic acid, butyric acid, $N^8$-acetyl spermidine, camptothecin, and their analogues.

As noted previously, one skilled in the art may make chemical modifications to the desired compound in order to make reactions of that compound more convenient for purposes of preparing conjugates of the invention.

In the conjugate of Formula I,

D is a drug moiety having pendant to the backbone thereof a chemically reactive functional group by means of which the drug backbone is bonded to the protein peptide linker, said functional group selected from the group consisting of a primary or secondary amine, hydroxyl, sulfhydryl, carboxyl, aldehyde or a ketone.

Representative of said amino containing drugs are mitomycin-C, mitomycin-A, daunorubicin, doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, cytarabine and derivatives thereof.

Representative of said alcohol group containing drugs are etoposide, camptothecin, taxol, esperamicin, 1,8-dihydroxy-bicyclo[7.3.1] trideca-4-9-diene-2,6-diyne-13-one, (U.S. Pat. No. 5,198,560), podophyllotoxin, anguidine, vincristine, vinblastine, morpholine-doxorubicin, n-(5,5-diacetoxy-pentyl) doxorubicin, and derivatives thereof.

Representative of said sulfhydryl containing drugs are esperamicin and 6-mercaptopurine, and derivatives thereof.

Representative of said carboxyl containing drugs are methotrexate, camptothecin (ring-opened form of the lactone), butyric acid, retinoic acid, and derivatives thereof.

Representative of said aldehyde and ketone containing drugs are anguidine and anthracyclines such as doxorubicin, and derivatives thereof.

A highly preferred group of cytotoxic agents for use as drugs in the present invention include drugs of the following formulae:

THE MITOMYCIN GROUP OF FORMULA (1):

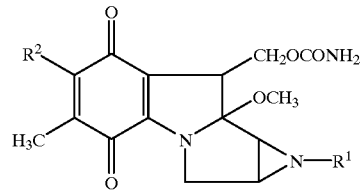

in which $R^1$ is hydrogen or methyl;

$R^2$ is —$NH_2$, —$OCH_3$, —$O(CH_2)_2OH$, —$NH(CH_2)_2SS(CH_2)_2NHAc$, —NHCH—C≡CH, —$NH(CH_2)_2SS(C_6H_4)NO_2$, —$O(CH_2)_2SS(CH_2)_2OH$, —N=CH—$NHOCH_3$, —$NH(C_6H_4)OH$, —$NH(CH_2)_2SS$ $(CH_2)_2NHCO(CH_2)_2CH(NH_2)COOH$

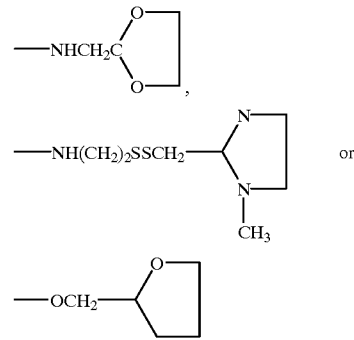

THE BLEOMYCIN GROUP OF FORMULA (2):

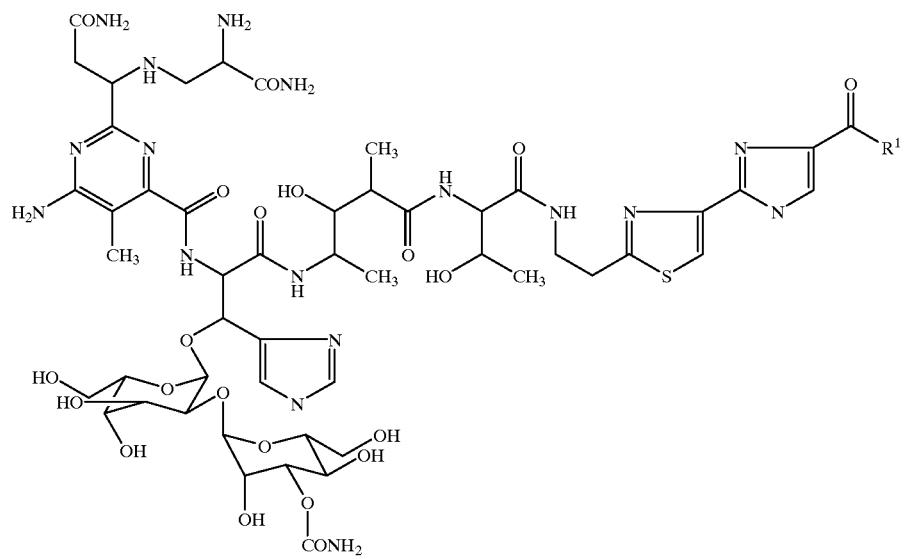

in which $R^1$ is hydroxy, amino, $C_1$–$C_3$ alkylamino, di($C_1$–$C_3$ alkyl) amino, $C_4$–$C_6$ polymethylene amino,

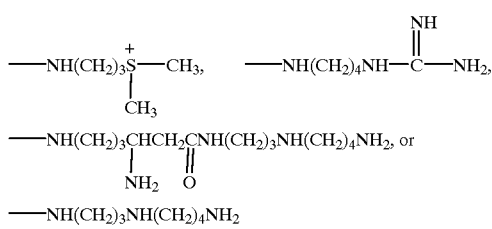

THE METHOTREXATE GROUP OF FORMULA (3):

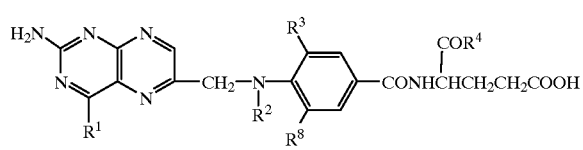

(3)

in which $R^1$ is amino or hydroxy;
$R^2$ is hydrogen or methyl;
$R^3$ is hydrogen, fluoro, chloro, bromo or iodo;
$R^4$ is hydroxy or a moiety which completes a salt of the carboxylic acid.

MELPHALAN OF FORMULA (4):

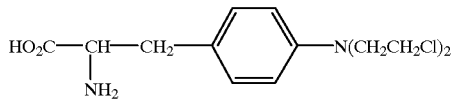

(4)

MERCAPTOPURINE OF FORMULA (5):

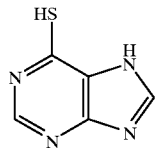

(5)

A CYTOSINE ARABINOSIDE OF FORMULA (6):

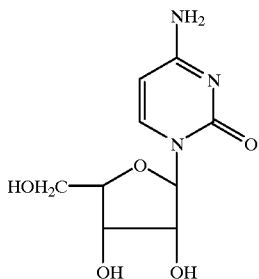

(6)

THE PODOPHYLLOTOXINS OF FORMULA (7):

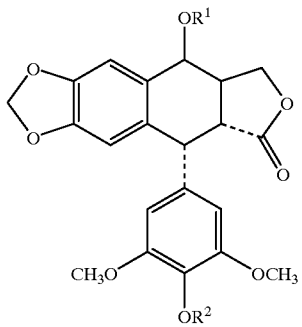

(7)

wherein
$R^2$ is hydrogen,
$R^1$ is hydrogen or

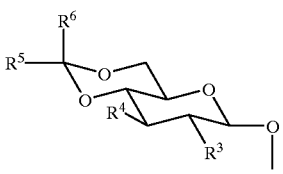

wherein
$R^3$ is $NH_2$, OH, $OCH_3$, $NH(C_1$–$C_3$ alkyl) or $N(C_1$–$C_3$ alkyl$)_2$
$R^4$ is OH, or $NH_2$,
$R^5$ is methyl or thienyl,
$R^6$ is hydrogen or methyl, or a phosphate salt thereof.

As used herein "$C_1$–$C_3$ alkyl" means a straight or branched carbon chain having from one to three carbon atoms; examples include methyl, ethyl, n-propyl and iso-propyl.

THE VINCA ALKALOID GROUP OF DRUGS OF FORMULA (8):

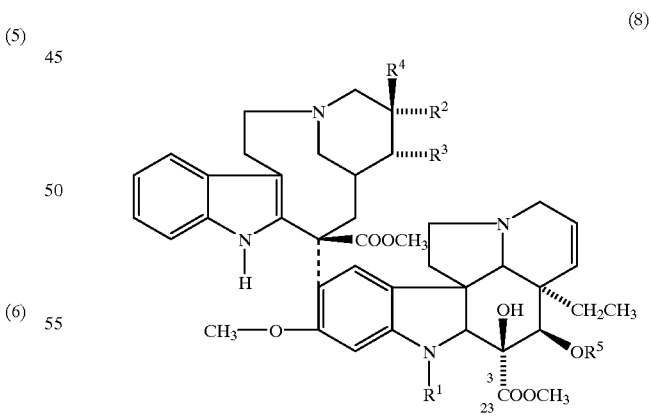

(8)

in which
$R^1$ is H, $CH_3$ or CHO;
when $R^2$ and $R^3$ are taken singly, $R^3$ is H, and one of $R^4$ and $R^2$ is ethyl and the other is H or OH;
when $R^2$ and $R^3$ are taken together with the carbons to which they are attached, they form an oxirane ring in which case $R^4$ is ethyl;

$R^5$ is hydrogen, $(C_1-C_3$ alkyl)—CO, or
chlorosubstituted $(C_1-C_3$ alkyl)—CO.

As used herein "$C_1-C_3$ alkyl" means a straight or branched carbon chain having from one to three carbon atoms; examples include methyl, ethyl, n-propyl and isopropyl.

DIFLUORONUCLEOSIDES OF FORMULA (9):

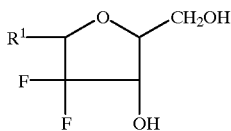
(9)

in which $R^1$ is a base of one of the formulae:

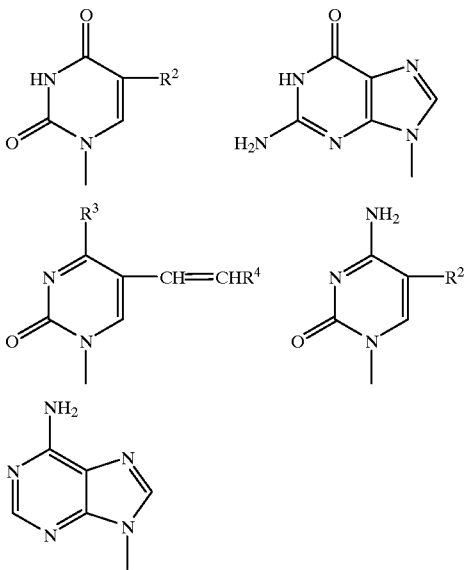

in which
$R^2$ is hydrogen, methyl, bromo, fluoro, chloro, or iodo;
$R^3$ is —OH or —NH$_2$;
$R^4$ is hydrogen, bromo, chloro, or iodo.

TAXOLS OF FORMULA (10):

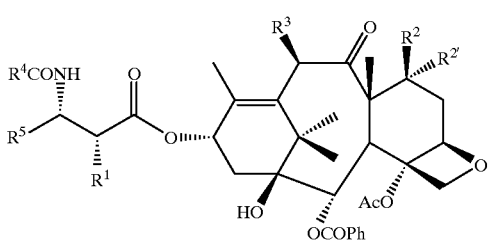
(10)

wherein
$R^1$ is hydroxy;
$R^2$ is hydrogen or hydroxy;
$R^{2'}$ is hydrogen or fluoro;
$R^3$ is hydrogen, hydroxy, or acetoxy;
$R^4$ is aryl, substituted aryl, $C_{1-6}$ alkyl, $C_{2-6}$ alkynyl or t-butoxy;

$R^5$ is $C_{1-6}$ alkyl, $C_{2-6}$ alkenyl, $C_{2-6}$ alkynyl, or —Z—$R^6$;
Z is a direct bond, $C_{1-6}$ alkyl or $C_{2-6}$ alkenyl;
$R^6$ is aryl, substituted aryl, $C_{3-6}$ cycloalkyl, thienyl or furyl.

As used herein, "alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. "Alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. "Alkynyl" means a straight or branched carbon chain having at least one carbon-carbon triple bond, and from two to six carbon atoms; examples include ethynyl, propynyl, butynyl, and hexynyl. "Aryl" means aromatic hydrocarbon having from six to ten carbon atoms; examples include phenyl and naphthyl. "Substituted aryl" means aryl substituted with at least one group selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, and amido.

ANGUIDINES OF FORMULA (11):

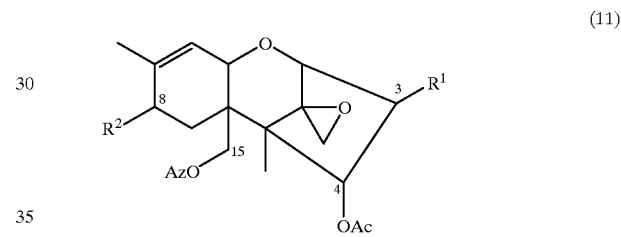
(11)

wherein
$R^1$ is OH or O
$R^2$ is H or O

Anguidine can be targeted at the C-3, C-4, C-8 or C-15 positions, as an ester or hydrazone.

THE ANTHRACYCLINES ANTIBIOTICS OF FORMULA (12):

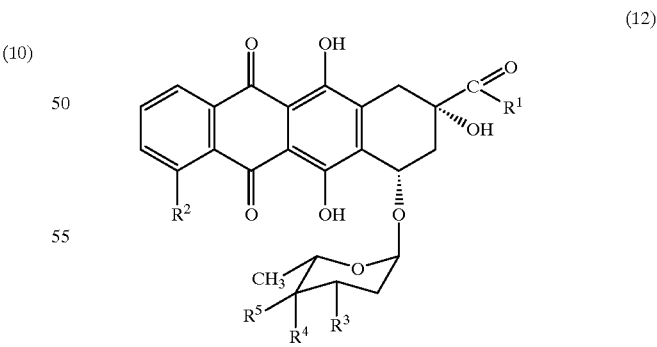
(12)

wherein
$R^1$ is —CH$_3$, —CH$_2$OH, —CH$_2$OCO(CH$_2$)$_3$CH$_3$ or —CH$_2$OCOCH(OC$_2$H$_5$)$_2$
$R^2$ is —OCH$_3$, —OH or —H
$R^3$ is —NH$_2$, —NHCOCF$_3$, 4-morpholinyl, 3-cyano-4-morpholinyl, 1-piperidinyl, 4-methoxy-1-piperidinyl, benzylamine, dibenzylamine, cyanomethylamine, 1-cyano-2-methoxyethyl amine, or NH—(CH$_2$)$_4$—CH(OAc)$_2$;

$R^4$ is —OH, —OTHP, or —H; and $R^5$ is —OH or —H provided that $R^5$ is not —OH when $R^4$ is —OH or —OTHP.

One skilled in the art understands that structural Formula (12) includes compounds which are drugs, or are derivatives of drugs, which have acquired in the art different generic or trivial names. Table I, which follows, represents a number of anthracycline drugs and their generic or trivial names and which are especially preferred for use in the present invention.

Of the compounds shown in Table I, the most highly preferred drug is Doxorubicin. Doxorubicin (also referred to herein as "DOX") is that anthracycline of Formula (1) in which $R_1$ is —CH$_2$OH, $R_3$ is —OCH$_3$, $R_4$ is —NH$_2$, $R_5$ —OH, and $R_6$ is —H.

the drug reagent is linked via the linker in the conjugate, can be any molecule that binds to, complexes with or reacts with the cell population sought to be therapeutically or otherwise biologically modified and, which possesses a free reactive sulfhydryl (—SH) group or can be modified to contain such a sulfhydryl group. The cell reactive molecule acts to deliver the therapeutically active drug moiety to the particular target cell population with which the ligand reacts. Such molecules include, but are not limited to, large molecular weight proteins such as, for example, antibodies, smaller molecular weight proteins, polypeptide or peptide ligands, and non-peptidyl ligands.

The non-immunoreactive protein, polypeptide, or peptide ligands which can be used to form the conjugates of this invention may include, but are not limited to, transferrin, epidermal growth factors ("EGF"), bombesin, gastrin, gastrin-releasing peptide, platelet-derived growth factor, IL-2, IL-6, tumor growth factors ("TGF"), such as TGF-α and TGF-β, vaccinia growth factor ("VGF"), insulin and

TABLE I

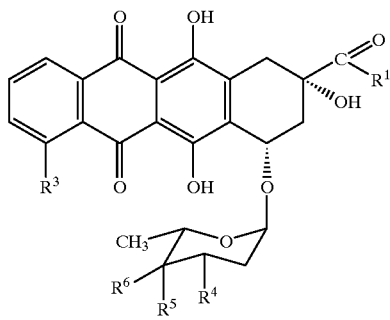

| Compound | $R^1$ | $R^3$ | $R^4$ | $R^5$ | $R^6$ |
|---|---|---|---|---|---|
| Daunorubicin[a] | CH$_3$ | OCH$_3$ | NH$_2$ | OH | H |
| Doxorubicin | CH$_2$OH | OCH$_3$ | NH$_2$ | OH | H |
| Detorubicin | CH$_2$OCOCH(OC$_2$H$_5$)$_2$ | OCH$_3$ | NH$_2$ | OH | H |
| Carminomycin | CH$_3$ | OH | NH$_2$ | OH | H |
| Idarubicin | CH$_3$ | H | NH$_2$ | OH | H |
| Epirubicin | CH$_2$OH | OCH$_3$ | NH$_2$ | H | OH |
| Esorubicin | CH$_2$OH | OCH$_3$ | NH$_2$ | H | H |
| THP | CH$_2$OH | OCH$_3$ | NH$_2$ | OTHP | H |
| AD-32 | CH$_2$OCO(CH$_2$)$_3$CH$_3$ | OCH$_3$ | NHCOCF$_3$ | OH | H |
| Morpholino-Dox | CH$_2$OH | OCH$_3$ | morpholino | OH | H |
| Cyano-morpholino-Dox | CH$_2$OH | OCH$_3$ | 3-cyano-morpholino | OH | H |
| DAPDox | CH$_2$OH | OCH$_3$ | —NH(CH$_2$)$_4$CH(OAc)$_2$ | OH | H |

[a] "Daunomycin" is an alternate name for daunorubicin

The most highly preferred drugs are the taxol, mitomycin C, and anthracycline antibiotic agents of Formula (12), described previously.

THE LIGAND

The "ligand" includes within its scope any molecule that specifically binds or reactively associates or complexes with a receptor or other receptive moiety associated with a given target cell population. This cell reactive molecule, to which insulin-like growth factors I and II. Non-peptidyl ligands may include, for example, carbohydrates, lectins, and apoprotein from low density lipoprotein.

The immunoreactive ligands comprise an antigen-recognizing immunoglobulin (also referred to as "antibody"), or an antigen-recognizing fragment thereof. Particularly preferred immunoglobulins are those immunoglobulins which can recognize a tumor-associated antigen. As used, "immunoglobulin" may refer to any recognized class or subclass of immunoglobulins such as IgG, IgA, IgM, IgD, or IgE. Preferred are those immunoglobulins which fall within the IgG class of immunoglobulins. The immunoglobulin can be derived from any species. Preferably, however, the immunoglobulin is of human, murine, or rabbit origin. Further, the immunoglobulin may be polyclonal or monoclonal, preferably monoclonal.

As noted, one skilled in the art will appreciate that the invention also encompasses the use of antigen recognizing immunoglobulin fragments. Such immunoglobulin fragments may include, for example, the Fab', F(ab')$_2$, F$_v$ or Fab fragments, or other antigen recognizing immunoglobulin fragments. Such immunoglobulin fragments can be prepared, for example, by proteolytic enzyme digestion, for example, by pepsin or papain digestion, reductive alkylation, or recombinant techniques. The materials and methods for preparing such immunoglobulin fragments are well-known to those skilled in the art. See generally, Parham, *J. Immunology,* 131, 2895 (1983); Lamoyi et al., *J. Immunological Methods,* 56, 235 (1983); Parham, id., 53, 133 (1982); and Matthew et al., id., 50, 239 (1982).

The immunoglobulin can be a "chimeric antibody" as that term is recognized in the art. Also, the immunoglobulin may be a "bifunctional" or "hybrid" antibody, that is, an antibody which may have one arm having a specificity for one antigenic site, such as a tumor associated antigen while the other arm recognizes a different target, for example, a hapten which is, or to which is bound, an agent lethal to the antigen-bearing tumor cell. Alternatively, the bifunctional antibody may be one in which each arm has specificity for a different epitope of a tumor associated antigen of the cell to be therapeutically or biologically modified. In any case, the hybrid antibodies have a dual specificity, preferably with one or more binding sites specific for the hapten of choice or one or more binding sites specific for a target antigen, for example, an antigen associated with a tumor, an infectious organism, or other disease state.

Biological bifunctional antibodies are described, for example, in European Patent Publication, EPA 0 105 360, to which those skilled in the art are referred. Such hybrid or bifunctional antibodies may be derived, as noted, either biologically, by cell fusion techniques, or chemically, especially with cross-linking agents or disulfide bridge-forming reagents, and may be comprised of whole antibodies and/or fragments thereof. Methods for obtaining such hybrid antibodies are disclosed, for example, in PCT application WO83/03679, published Oct. 27, 1983, and published European Application EPA 0 217 577, published Apr. 8, 1987, both of which are incorporated herein by reference. Particularly preferred bifunctional antibodies are those biologically prepared from a "polydoma" or "quadroma" or which are synthetically prepared with cross-linking agents such as bis-(maleimido)-methyl ether ("BMME"), or with other cross-linking agents familiar to those skilled in the art.

In addition the immunoglobin may be a single chain antibody ("SCA"). These may consist of single chain Fv fragments ("scFv") in which the variable light ("$V_L$") and variable heavy ("$V_H$") domains are linked by a peptide bridge or by disulfide bonds. Also, the immunoglobulin may consist of single $V_H$ domains (dAbs) which possess antigen-binding activity. See, e.g., G. Winter and C. Milstein, *Nature,* 349, 295 (1991); R. Glockshuber et al., *Biochemistry* 29, 1362 (1990); and, E. S. Ward et al., *Nature* 341, 544 (1989).

Especially preferred for use in the present invention are chimeric monoclonal antibodies, preferably those chimeric antibodies having specificity toward a tumor associated antigen. As used herein, the term "chimeric antibody" refers to a monoclonal antibody comprising a variable region, i.e. binding region, from one source or species and at least a portion of a constant region derived from a different source or species, usually prepared by recombinant DNA techniques. Chimeric antibodies comprising a murine variable region and a human constant region are especially preferred in certain applications of the invention, particularly human therapy, because such antibodies are readily prepared and may be less immunogenic than purely murine monoclonal antibodies. Such murine/human chimeric antibodies are the product of expressed immunoglobulin genes comprising DNA segments encoding murine immunoglobulin variable regions and DNA segments encoding human immunoglobulin constant regions. Other forms of chimeric antibodies encompassed by the invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L, et al., *Proc. Nat'l Acad. Sci.,* 81, 6851 (1984).

Encompassed by the term "chimeric antibody" is the concept of "humanized antibody", that is those antibodies in which the framework or "complementarity determining regions ("CDR") have been modified to comprise the CDR of an immunoglobulin of different specificity as compared to that of the parent immunoglobulin. In a preferred embodiment, a murine CDR is grafted into the framework region of a human antibody to prepare the "humanized antibody". See, e.g., L. Riechmann et al., *Nature* 332, 323 (1988); M. S. Neuberger et al., *Nature* 314, 268 (1985). Particularly preferred CDR'S correspond to those representing sequences recognizing the antigens noted above for the chimeric and bifunctional antibodies. The reader is referred to the teaching of EPA 0 239 400 (published Sep. 30, 1987), incorporated herein by reference, for its teaching of CDR modified antibodies.

One skilled in the art will recognize that a bifunctional-chimeric antibody can be prepared which would have the benefits of lower immunogenicity of the chimeric or humanized antibody, as well as the flexibility, especially for therapeutic treatment, of the bifunctional antibodies described above. Such bifunctional-chimeric antibodies can be synthesized, for instance, by chemical synthesis using cross-linking agents and/or recombinant methods of the type described above. In any event, the present invention should not be construed as limited in scope by any particular method of production of an antibody whether bifunctional, chimeric, bifunctional-chimeric, humanized, or an antigen-recognizing fragment or derivative thereof.

In addition, the invention encompasses within its scope immunoglobulins (as defined above) or immunoglobulin fragments to which are fused active proteins, for example, an enzyme of the type disclosed in Neuberger, et al., PCT application, WO86/01533, published Mar. 13, 1986. The disclosure of such products is incorporated herein by reference.

As noted, "bifunctional", "fused", "chimeric" (including humanized), and "bifunctional-chimeric" (including humanized) antibody constructions also include, within their individual contexts constructions comprising antigen recognizing fragments. As one skilled in the art will recognize, such fragments could be prepared by traditional enzymatic cleavage of intact bifunctional, chimeric, humanized, or chimeric-bifunctional antibodies. If, however, intact antibodies are not susceptible to such cleavage, because of the nature of the construction involved, the noted constructions can be prepared with immunoglobulin fragments used as the starting materials; or, if recombinant techniques are used, the DNA sequences, themselves, can be tailored to encode the desired "fragment" which, when expressed, can be combined in vivo or in vitro, by chemical or biological means, to prepare the final desired intact immunoglobulin "fragment". It is in this context, therefore, that the term "fragment" is used.

Furthermore, as noted above, the immunoglobulin (antibody), or fragment thereof, used in the present invention may be polyclonal or monoclonal in nature. Monoclonal antibodies are the preferred immunoglobulins, however. The preparation of such polyclonal or monoclonal antibodies now is well known to those skilled in the art who, of course, are fully capable of producing useful immunoglobulins which can be used in the invention. See, e.g., G. Kohler and C. Milstein, *Nature* 256, 495 (1975). In addition, hybridomas and/or monoclonal antibodies which are produced by such hybridomas and which are useful in the practice of the present invention are publicly available from sources such as the American Type Culture Collection ("ATCC") 12301 Parklawn Drive, Rockville, Md. 20852 or, commerically, for example, from Boehringer-Mannheim Biochemicals, P.O. Box 50816, Indianapolis, Ind. 46250.

Particularly preferred monoclonal antibodies for use in the present invention are those which recognize tumor associated antigens. Such monoclonal antibodies, are not to be so limited, however, and may include, for example, the following:

| Antigen Site Recognized | Monoclonal Antibodies | Reference |
| --- | --- | --- |
| Lung Tumors | KS1/4 | N. M. Varki, et al., Cancer Res. 44:681, 1984 |
|  | 534, F8; 604A9 | F. Cuttitta, et al., in: G. L. Wright (ed) Monoclonal Antibodies and Cancer, Marcel Dekker, Inc., NY., p. 161, 1984. |
| Squamous Lung | G1, LuCa2, LuCa3, LuCa4 | Kyoizumi et al., Cancer Res., 45:3274, 1985. |
| Small Cell Lung Cancer | TFS-2 | Okabe et al., Cancer Res. 45:1930, 1985. |

-continued

| Antigen Site Recognized | Monoclonal Antibodies | Reference |
| --- | --- | --- |
| Colon Cancer | 11.285.14 14.95.55 | G. Rowland, et al., Cancer Immunol.Immunother., 19:1, 1985 |
|  | NS-3a-22, NS-10 NS-19-9, NS-33a NS-52a, 17-1A | Z. Steplewski, et al., Cancer Res., 41:2723, 1981. |
| Carcinoembryonic | MoAb 35 or ZCE025 | Acolla, R. S. et al., Proc. Natl. Acad. Sci., (USA), 77:563, 1980. |
| Melanoma | 9.2.27 | T. F. Bumol and R. A. Reisfeld, Proc. Natl. Acad. Sci., (USA), 79:1245, 1982. |
| p97 | 96.5 | K. E. Hellstrom, et al., MonoclonalAntibodies and Cancer, loc. cit. p. 31. |
| Antigen T65 | T101 | Boehringer-Mannheim, P.O. Box 50816, Indianapolis, IN 46250 |
| Ferritin | Antiferrin | Boehringer-Mannheim, P.O. Box 50816, Indianapolis, IN 46250 |
|  | R24 | W. G. Dippold, et al., Proc. Natl. Acad. Sci. (USA), 77:6114, 1980 |
| Neuroblastoma | P1 153/3 | R. H. Kennet and F. Gilbert, Science, 203:1120, 1979. |
|  | MIN 1 | J. T. Kemshead in Monoclonal Antibodies and Cancer, loc. cit. p. 49. |
|  | UJ13A | Goldman et al., Pediatrics, 105:252, 1984. |
| Glioma | BF7, GE2, CG12 | N. de Tribolet, et al., in Monoclonal Antibodies and Cancer, loc. cit. p. 81 |
| Ganglioside | L6 | I. Hellstrom et al. Proc. Natl Acad. Sci. (U.S.A) 83:7059 (1986); U.S. Pat. Nos. 4,906,562, issued March 6, 1990 and 4,935,495, issued June 19, 1990. |
|  | Chimeric L6 | U.S. Ser. No. 07/923,244, (abandoned) filed Oct. 27, 1986, equivalent to PCT Patent Publication, WO 88/03145, published May 5, 1988. |
| Lewis Y | BR64 | U.S. Ser. Nos. 07/289,635 (abandoned) filed December 22, 1988, and U.S. Ser. No. 07/443,696 (now U.S. Pat. No. 5,242,824) Nov. 29, 1989, equivalent to European Patent Publication, EP A 0 375 562, published June 27, 1990, |
| fucosylated Lewis Y | BR96, Chimeric BR96 | U.S. Ser. Nos. 07/374,947 (abandoned) filed June 30, 1989, and U.S. Ser. No. 07/544,246 (abandoned) filed June 26, 1990, equi-valent to PCT Patent Publication, WO 91/00295, published January 10, 1991. |
| Breast Cancer | B6.2, B72.3 | D. Colcher, et al., in Monoclonal Antibodies and Cancer, loc. cit. p. 121. |
| Osteogenic Sarcoma | 791T/48, 791T/36 | M. J. Embleton, ibid, p. 181 |
| Leukemia | CALL 2 | C. T. Teng, et al., Lancet, 1:01, 1982 |
|  | anti-idiotype | R. A. Miller, et al., N. Eng. J. Med., 306:517, 1982 |
| Ovarian Cancer | OC 125 | R. C. Bast, et al., J. Clin. Invest., 68:1331, 1981. |

-continued

| Antigen Site Recognized | Monoclonal Antibodies | Reference |
|---|---|---|
| Prostate Cancer | D83.21, P6.2, Turp-27 | J. J. Starling, et al., in Monoclonal Antibodies and Cancer, loc. cit., p. 253 |
| Renal Cancer | A6H, D5D | P. H. Lange, et al., Surgery, 98:143, 1985. |

In the most preferred embodiment, the ligand containing conjugate is derived from chimeric antibody BR96, "ChiBR96", disclosed in U.S. Ser. No. 07/544,246, filed Jun. 26, 1990, and which is equivalent to PCT Published Application, WO 91/00295, published Jan. 10, 1991. ChiBR96 is an internalizing murine/human chimeric antibody and is reactive, as noted, with the fucosylated Lewis Y antigen expressed by human carcinoma cells such as those derived from breast, lung, colon, and ovarian carcinomas. The hybridoma expressing chimeric BR96 and identified as ChiBR96 was deposited on May 23, 1990, under the terms of the Budapest Treaty, with the American Type Culture Collection ("ATCC"), 12301 Parklawn Drive, Rockville, Md. 20852. Samples of this hybridoma are available under the accession number ATCC HB 10460. ChiBR96 is derived, in part, from its source parent, BR96. The hybridoma expressing BR96 was deposited, on Feb. 21, 1989, at the ATCC, under the terms of the Budapest Treaty, and is available under the accession number HB 10036. Other hybridomas deposited with and accepted under the provisions of the Budapest Treaty by the American Type Culture Collection, 12301 Parklawn Drive, Rockville, Md. 20852 include HB8677, deposited Dec. 6, 1984, which produces L6 antibody, HB9895, deposited Nov. 16, 1988, which produces BR64 antibody, and HB9240, deposited Nov. 14, 1986, and HB9241, deposited Oct. 24, 1986, which produce chimeric L6 antibody. With respect to all of the foregoing hybridomas, all restrictions upon public access to the deposits will be irrevocably removed upon the grant of a patent on this application, the deposits will be replaced if viable samples cannot be dispensed by the depository, and the deposits will be maintained in a public depository for a period of thirty years after the date of deposit, or five years after the last request for a sample or for the effective life of the patent, whichever is longer. The desired hybridoma is cultured and the resulting antibodies are isolated from the cell culture supernatant using standard techniques now well known in the art. See, e.g., "Monoclonal Hybridoma Antibodies: Techniques and Applications", Hurell (ed.) (CRC Press, 1982).

Thus, as used "immunoglobulin" or "antibody" encompasses within its meaning all of the immunoglobulin/antibody forms or constructions noted above.

Preparation of the Conjugates

The conjugates of the present invention may be constructed by attaching the drug moiety to the antibody through a linker made up of a peptide sequence which may be cleaved by the lysosomal proteases cathepsin B, C and D, and a self-immolating spacer.

A process for preparing the compound of the present invention is one wherein a solution of the antibody in a phosphate buffer or PBS was treated with a solution of dithiothreitol (DTT) at 25–45° C., for about 1–10 hours under $N_2$. The solution was then diafiltered against phosphate buffered saline (PBS) for ½ to 12 hours depending on the size of diafiltration cell and volume of solution under $N_2$, until the effluent is free of SH groups, then treated with the appropriate amount of peptide-PABC-drug [based on the number of SH groups in the Mab (determined by Ellman titration)] in distilled water, at 0±10° C. for 15 minutes to 8 hours. The solution was then dialyzed against PBS for about 24 hours, at room temperature, then filtered and the filtrate was shaken for 15 minutes to 8 hours at room temperature with Biobeads, followed by another filtration.

Schemes 1–11 show the synthesis of model compounds that were tested with cathepsin B in order to determine the optimal characteristics of the linker including the peptide sequence, self-immolating spacer, and attachment to antibody.

Scheme 12 shows the synthesis of the linker compound MC-Phe-Lys-PABC-DOX (50) which is conjugated to the antibody carrier. The NHS active ester of Fmoc-Phe (43) was coupled to $N^\epsilon$-Mtr-Lys (42) in an organic/aqueous solvent mixture to give the dipeptide Fmoc-Phe-$N^\epsilon$-Mtr-Lys (44). This in turn was coupled to p-aminobenzyl alcohol using EEDQ resulting in alcohol 45. The Fmoc group was removed with diethylamine, and the free N-terminal Phe was coupled to MC-NHS to give maleimidopeptide alcohol 47. Addition of bis-p-nitrophenyl carbonate provided the activated carbonate 48 and the p-nitrophenyl group was displaced by DOX in NMP at room temperature. The resulting substrate MC-Phe-$N^\epsilon$-Mtr-Lys-PABC-DOX (49) was deprotected in quantitative yield by treatment with dichloroacetic acid/anisole in $CH_2Cl_2$ for 1 hour to give 50.

Scheme 13 shows the synthesis of a MMC-containing linker compound MC-Phe-Lys-PABC-MMC (52) from activated carbonate 48. The aziridine nitrogen of MMC is not nucleophilic enough to directly displace the p-nitrophenol of 48 but, in the presence of a 10-fold excess of HOBt, some of the corresponding HOBt active ester forms, and is active enough to react with MMC. Chloroacetic acid is used instead of dichloroacetic acid for the deprotection of 51 because of acid sensitivity of MMC.

Scheme 14 shows the preparation of a taxol containing linker compound MC-Phe-Lys-PABC-7-taxol (55). Maleimidopeptide alcohol 47 was treated with 2'-Mtr-taxol-7-chloroformate (prepared from 53) to give MC-Phe-$N^\epsilon$-Mtr-Lys-PABC-7-Taxol (54). This was deprotected with chloroacetic acid to give 55.

Scheme 15 shows the synthesis of a citrulline containing linker compound MC-Val-Cit-PABC-DOX (62) which is carried out essentially as described above for 49 and requires no side chain deprotection.

Scheme 16 shows the preparation of a linker compound containing an added aminocaproyl spacer designed so as to move the site of enzymatic cleavage away from the bulky antibody. MC-NH-C-Phe-Lys-PABC-DOX (72) was prepared using procedures essentially identical to those used in the synthesis of 50 and 55.

Scheme 17 shows the synthesis of a MMC-containing linker compound MC-Phe-Lys-GABA-MMC (78) which incorporates a GABA spacer in place of PABC. This was prepared essentially as described for 52 above.

Scheme 18 shows the synthesis of a potential protease-active prodrug of cortisone, Z-Phe-Lys-Cortisone (81). This was prepared essentially as described for MC-Phe-Lys-PABC-DOX (50).

Scheme 19 shows the synthesis of a linker compound containing taxol-2'-ethyl carbonate, an active prodrug of taxol. Compounds of the present invention include BR96-succinimidocaproyl-phenylalanine-lysine-p-aminovenzyl-carbamoyloxy-doxorubicin, BR96-succinimidocaproyl-valine-lysine-p-aminobenzyl-carbamoyloxy-doxorubicin, BR96-succinimidocaproyl-valine-citrulline-p-aminobenzyl-carbamoyloxy-doxorubicin, BR96-succinimidocaproyl-phenylalanine-lysine-p-aminobenzyl-carbamoyloxy-2'-taxol, BR96-succinimidocaproyl-phenylalanine-lysine-p-amonobenzyl-carbamoyolxy-7-taxol, and BR96-succinimidocaproyl-phenylalanine-lysine-p-aminobenzyl-carbamoyolxy-motomycin-c.

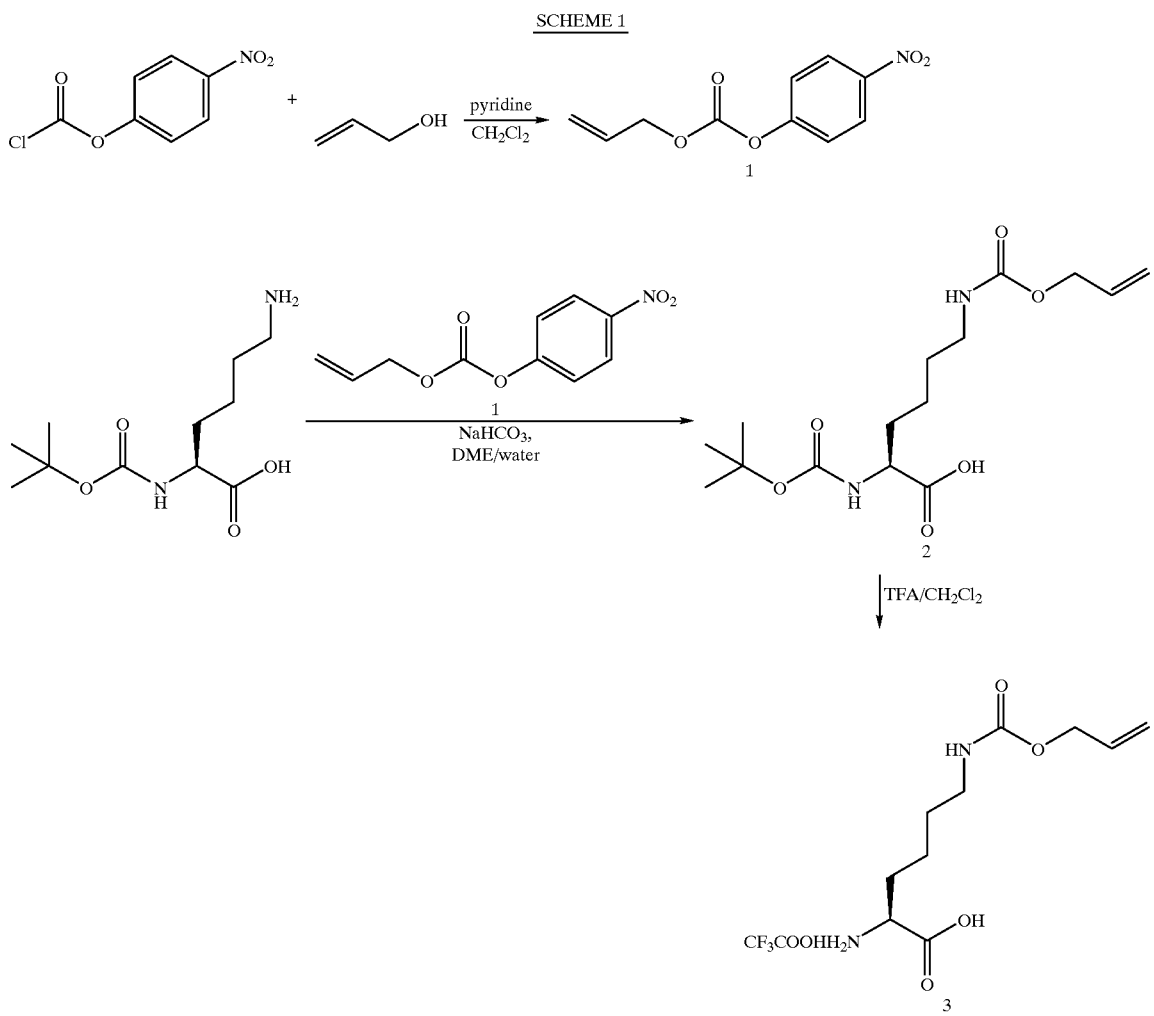

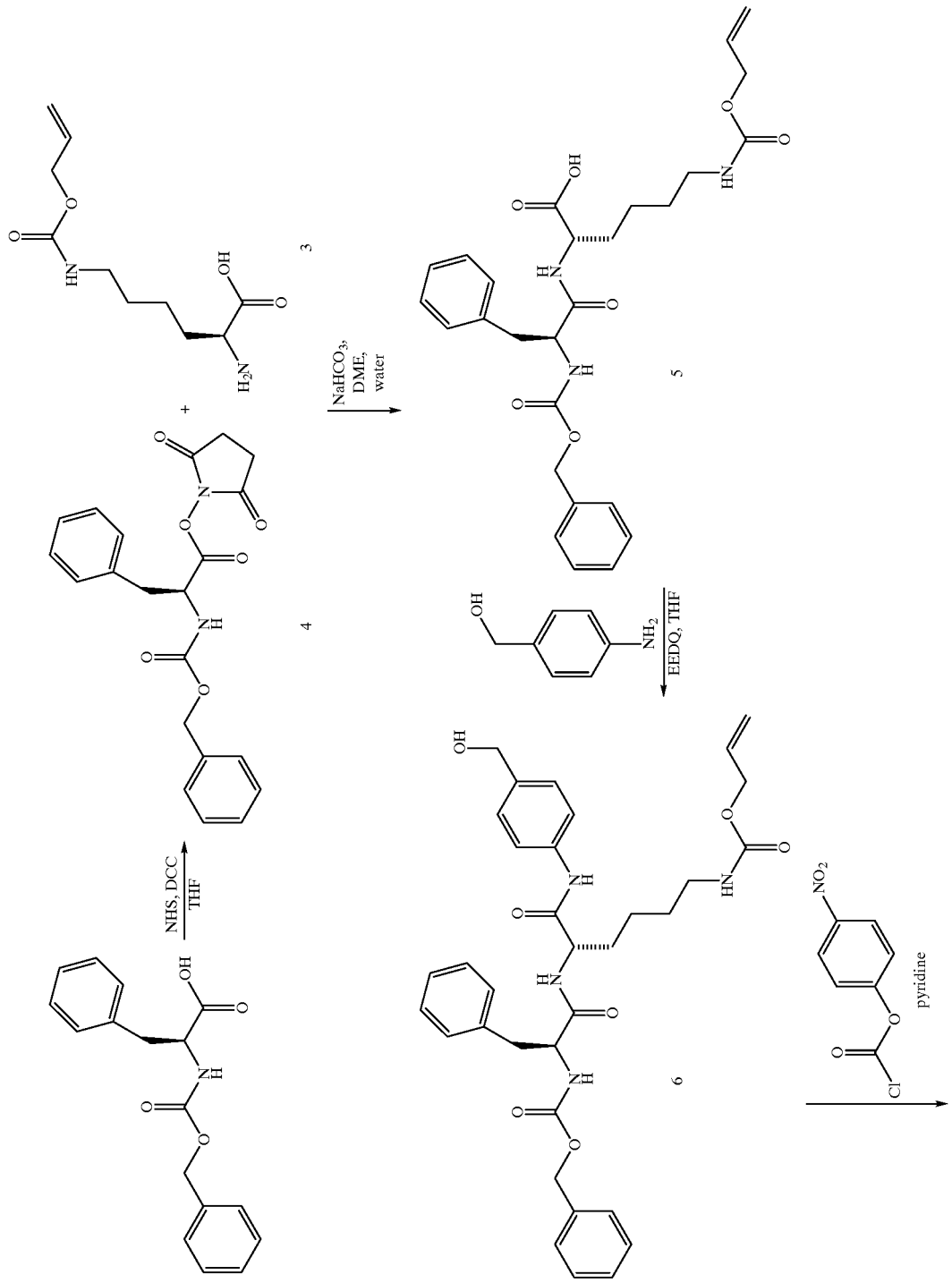
SCHEME 2

-continued
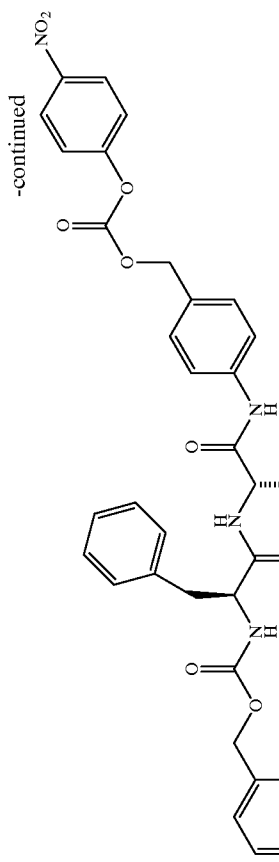
DOX-HCl,
Et₃N, NMP
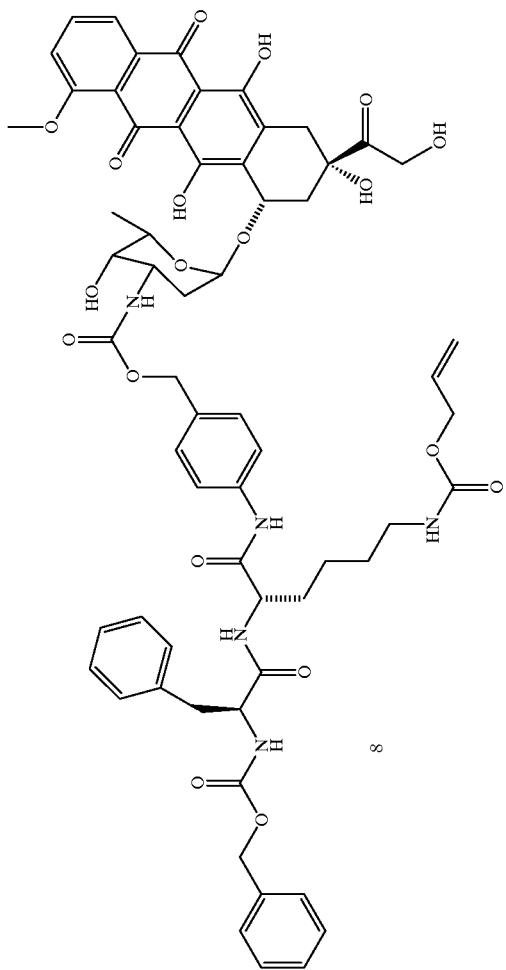

SCHEME 3
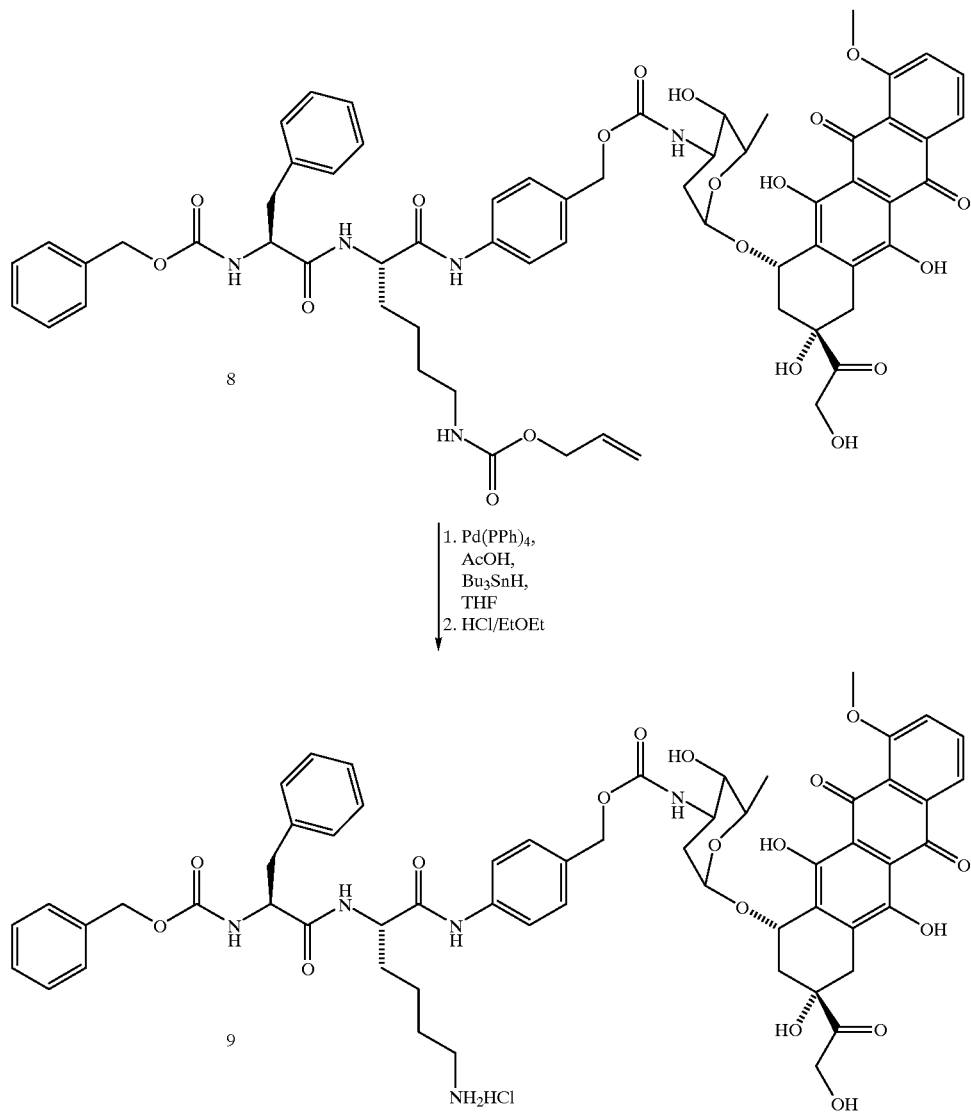

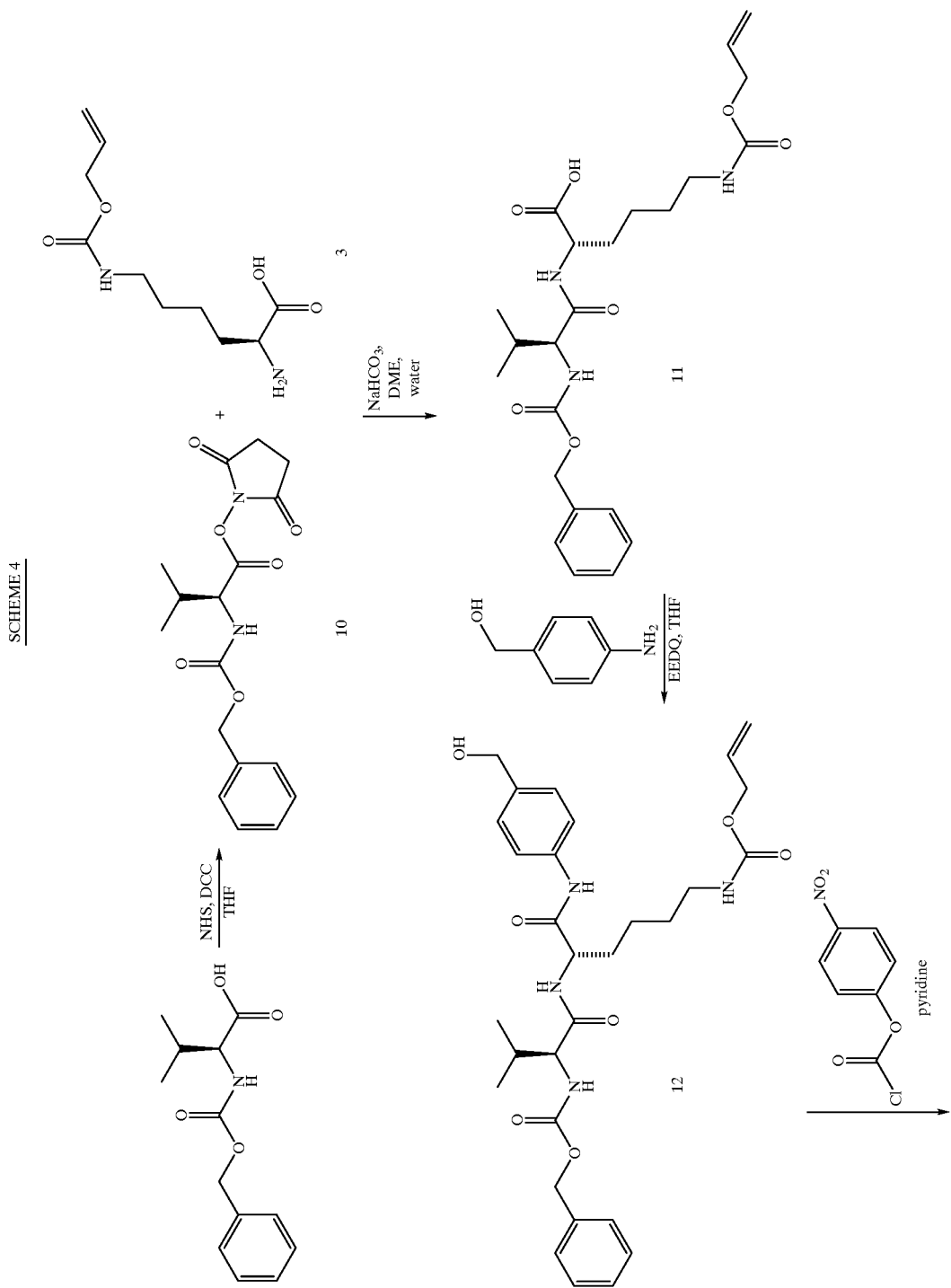

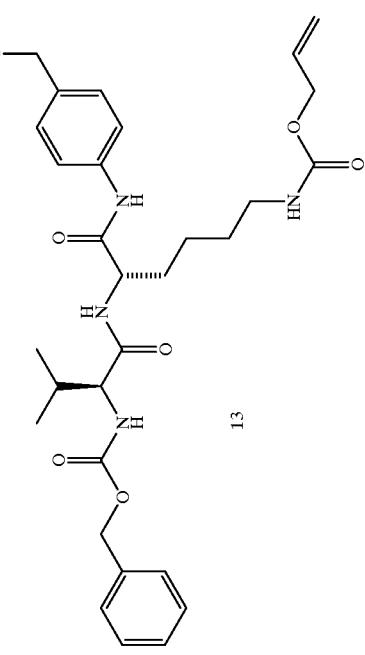
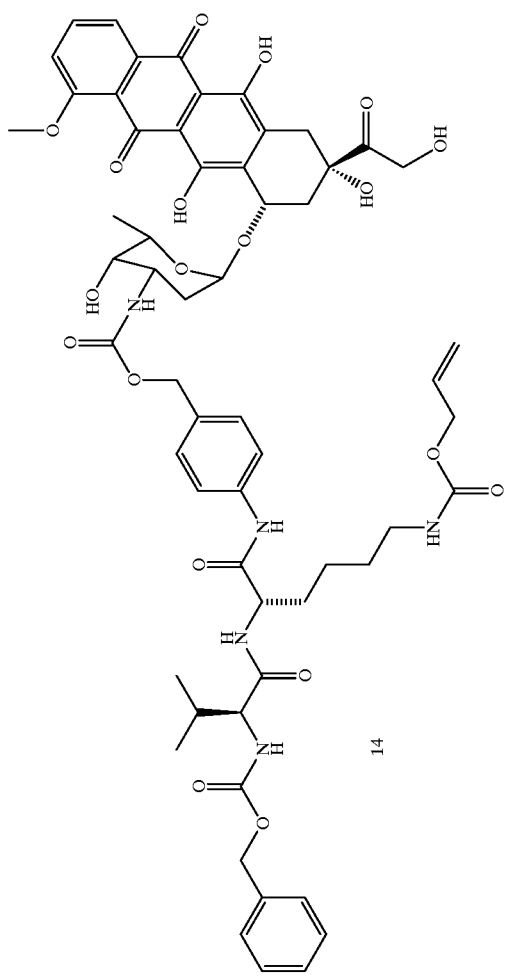

SCHEME 5
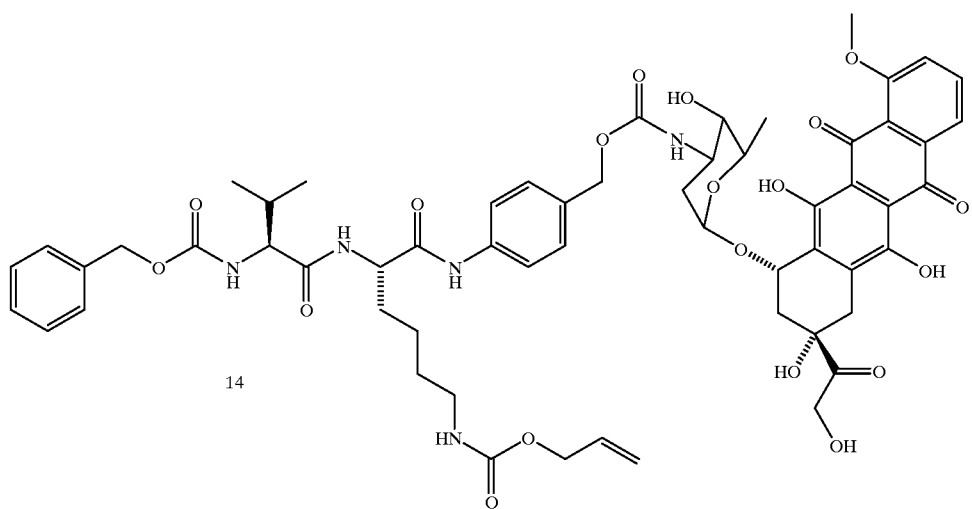
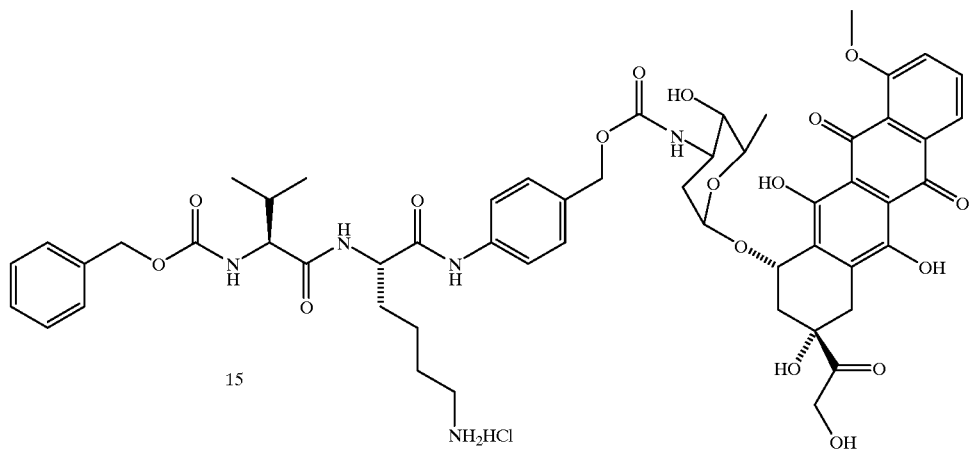
SCHEME 6
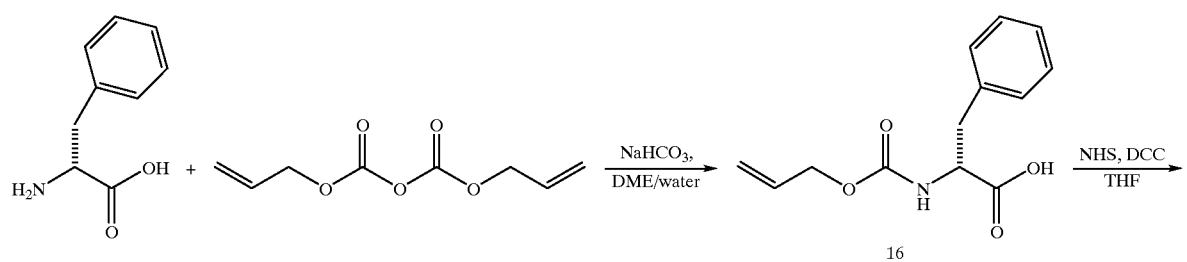

-continued
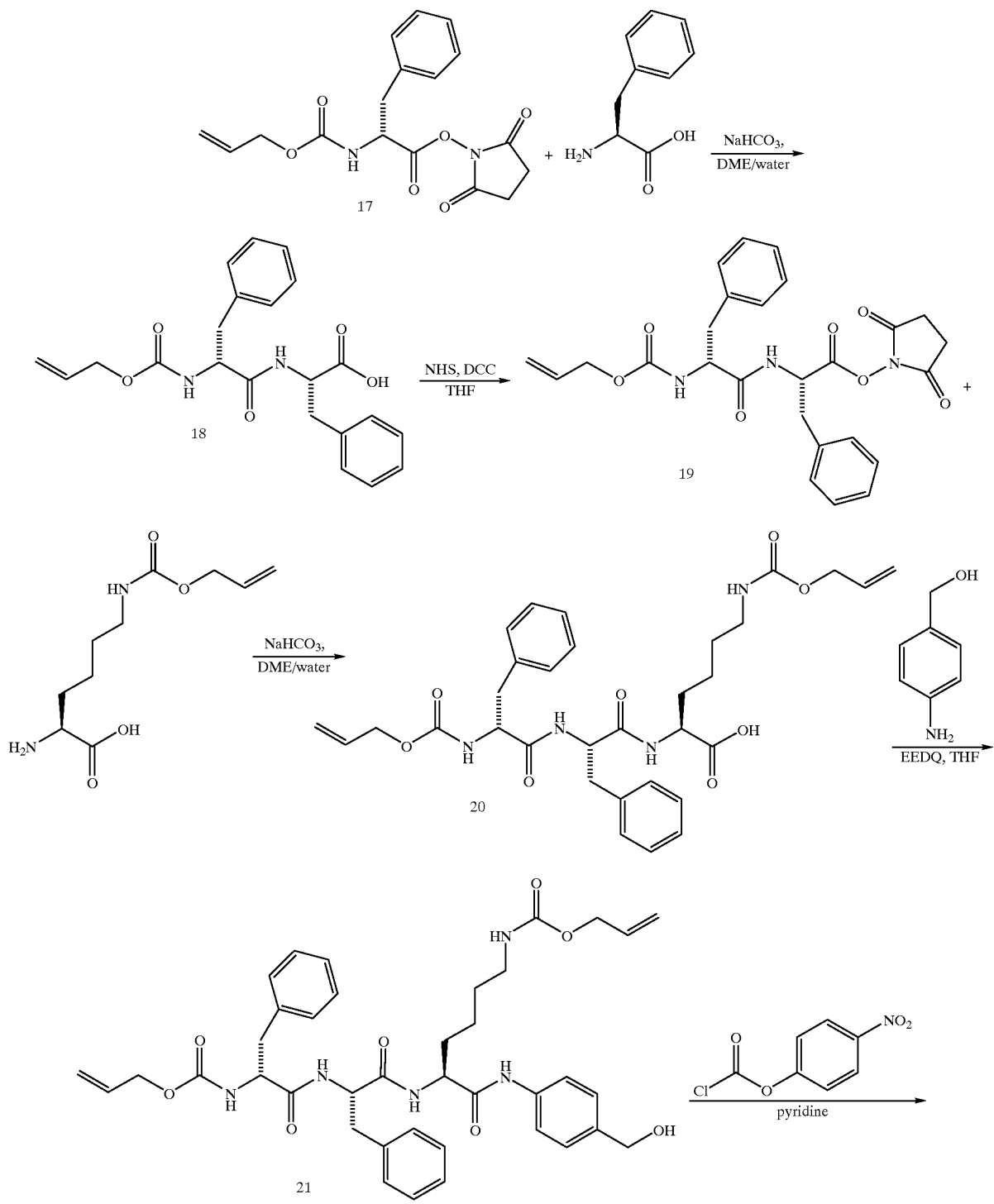

-continued
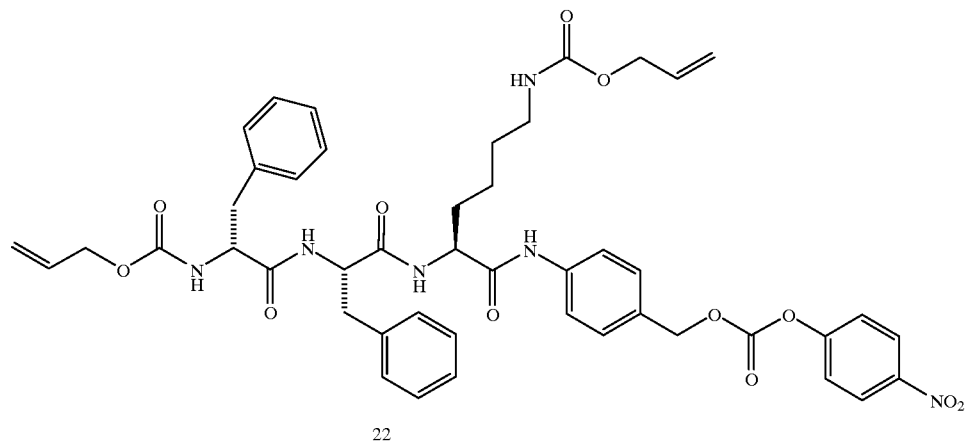
20
SCHEME 7
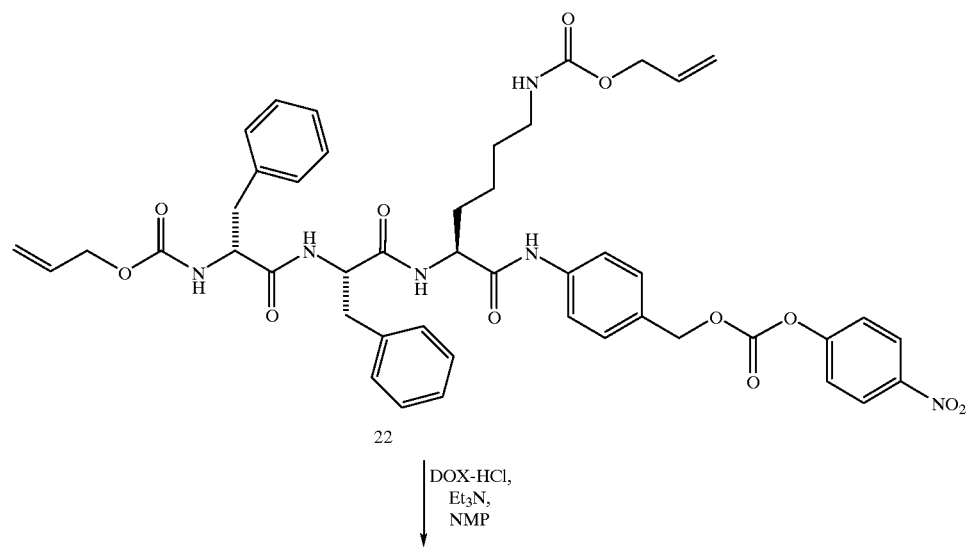
DOX-HCl,
Et₃N,
NMP

-continued
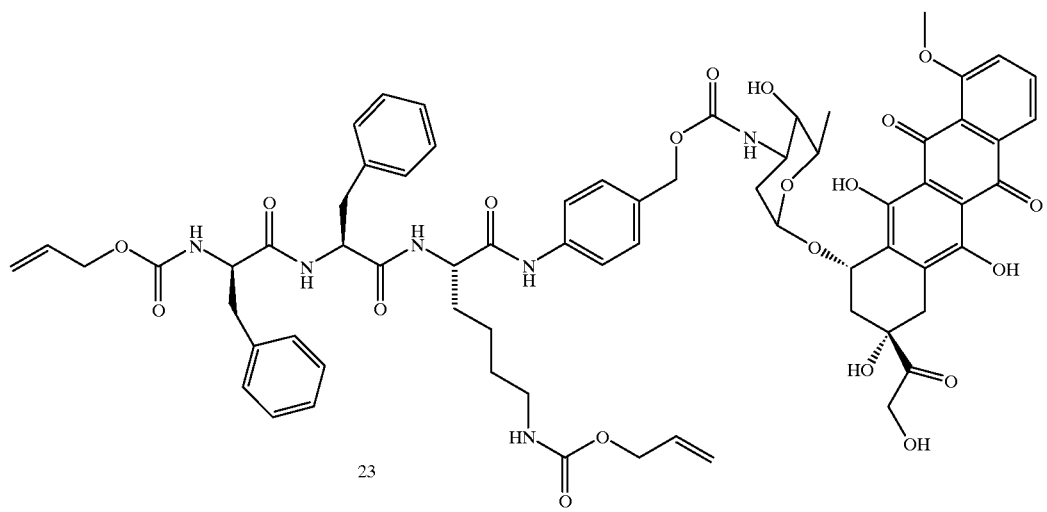
23
1. Pd(PPh$_3$)$_4$,
   AcOH,
   Et$_3$SiH,
   CH$_2$Cl$_2$/CH$_3$OH
2. HCl/EtOEt
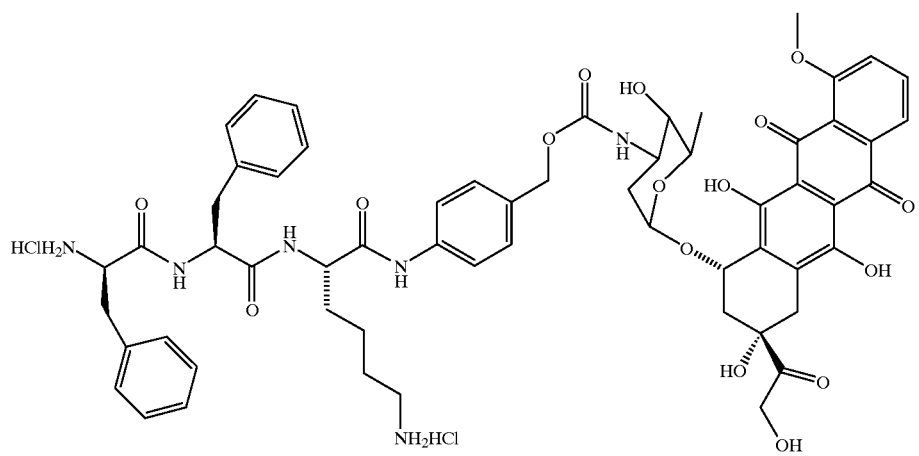
24
SCHEME 8
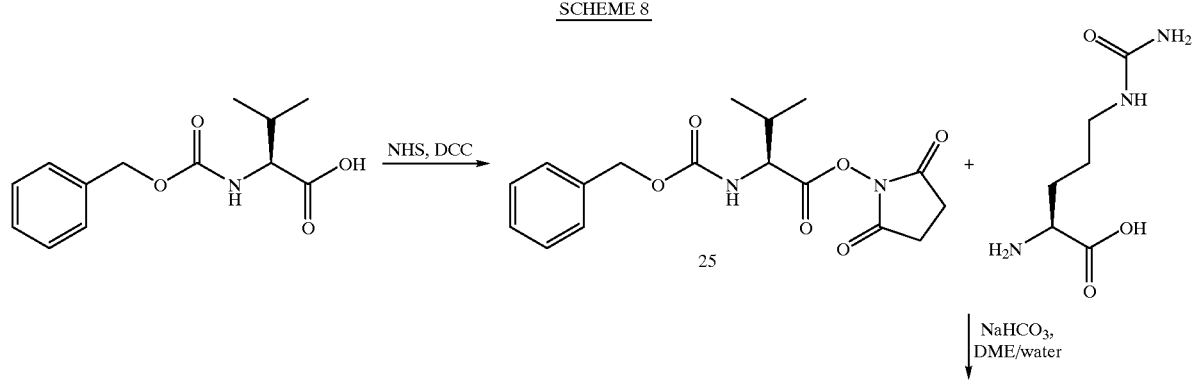
NaHCO$_3$,
DME/water

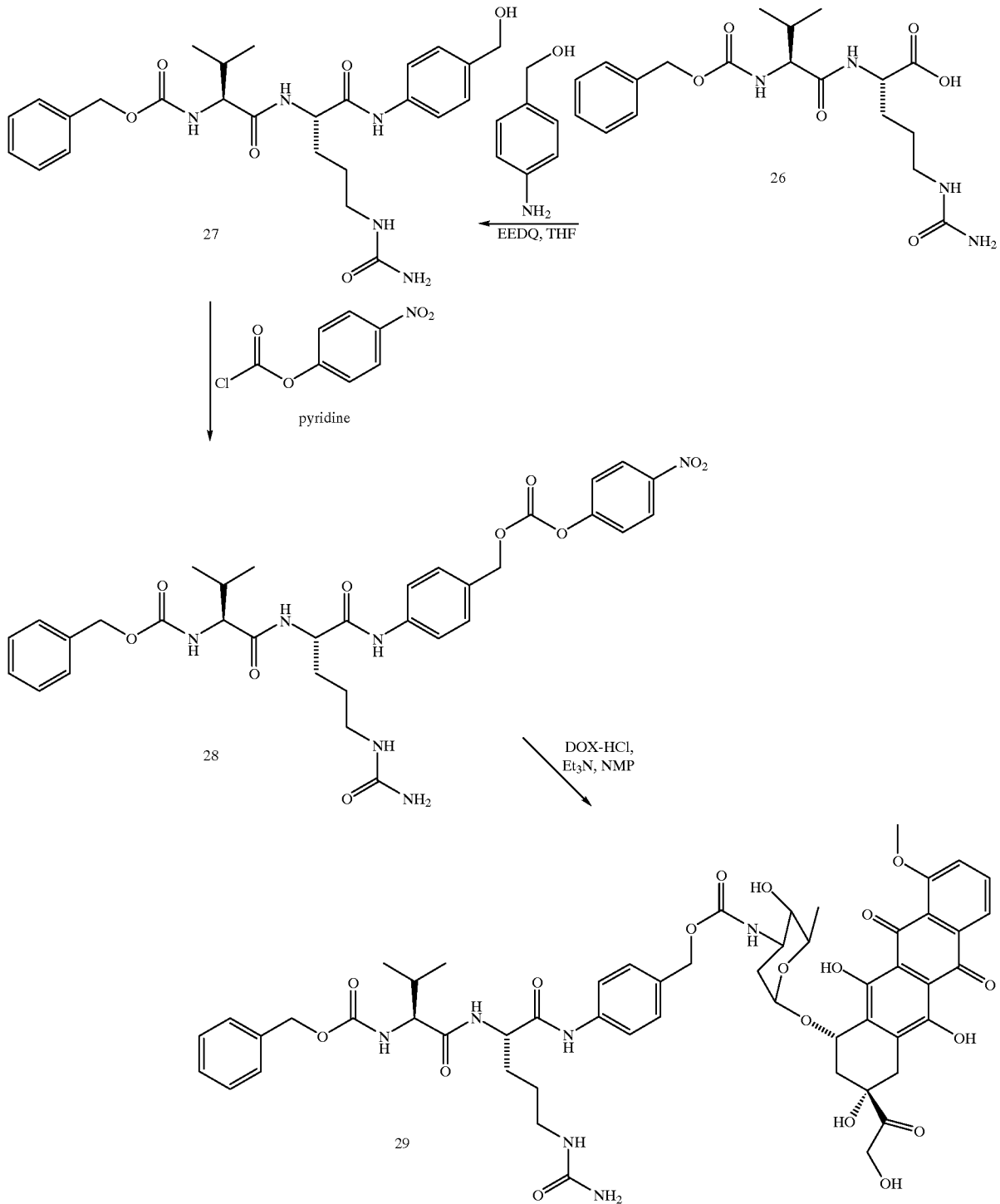

SCHEME 9
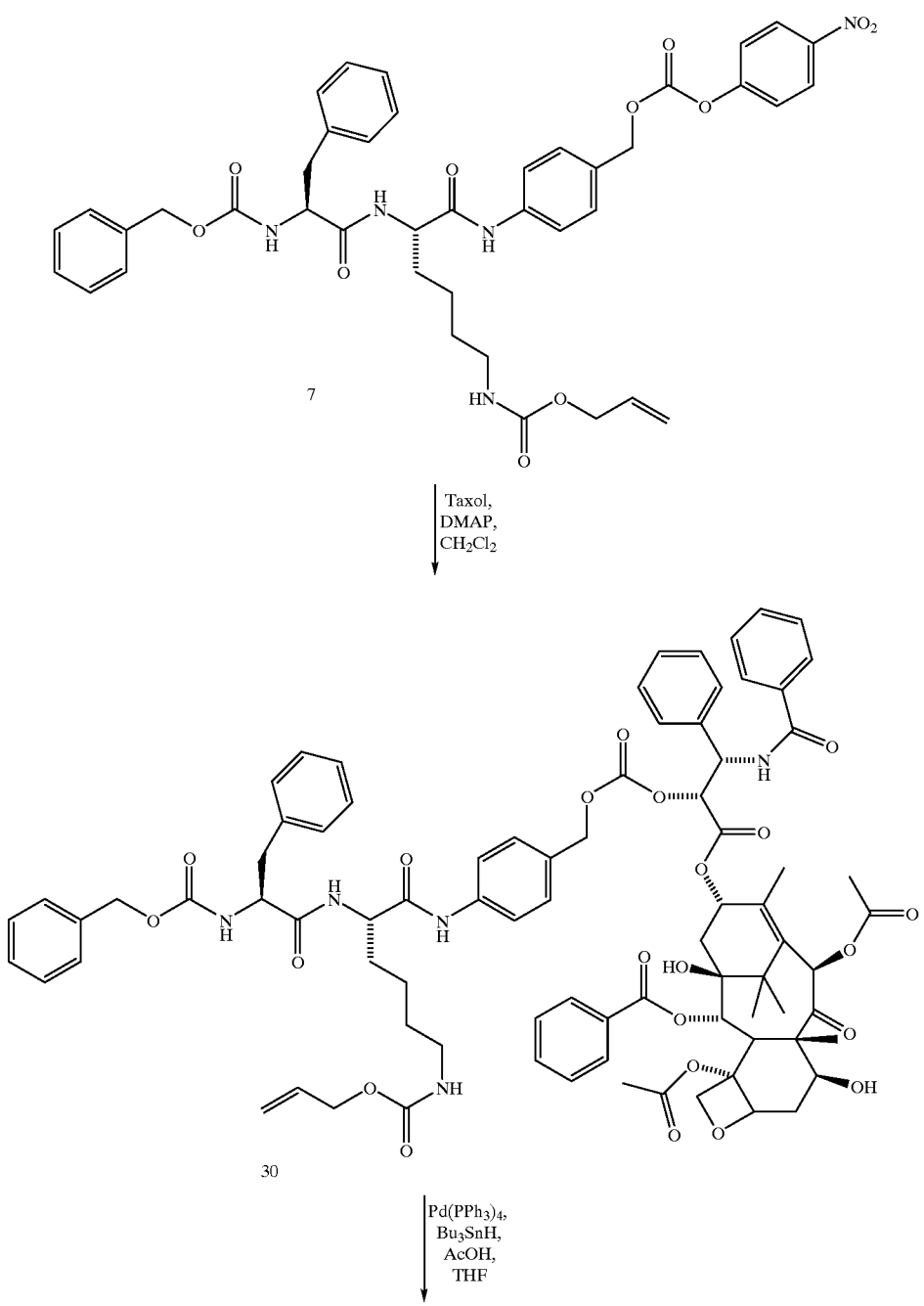

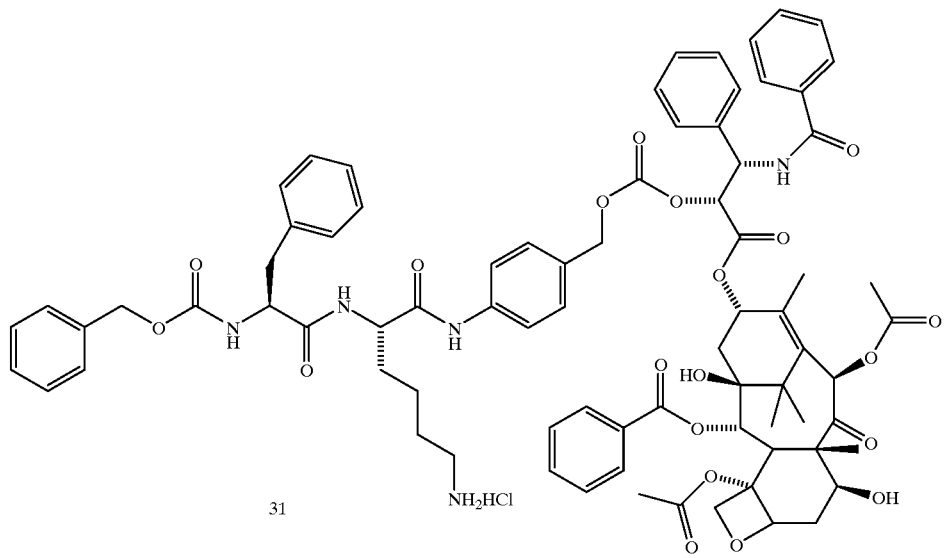
31
SCHEME 10
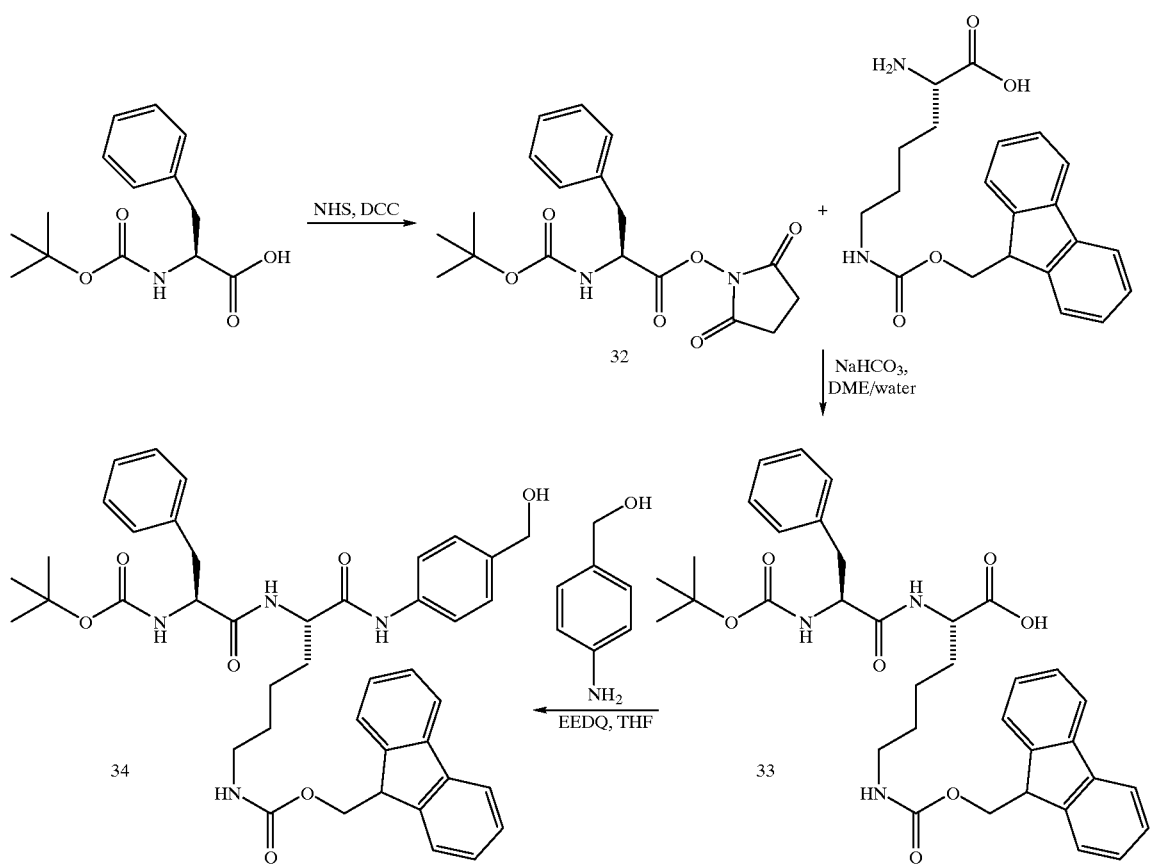

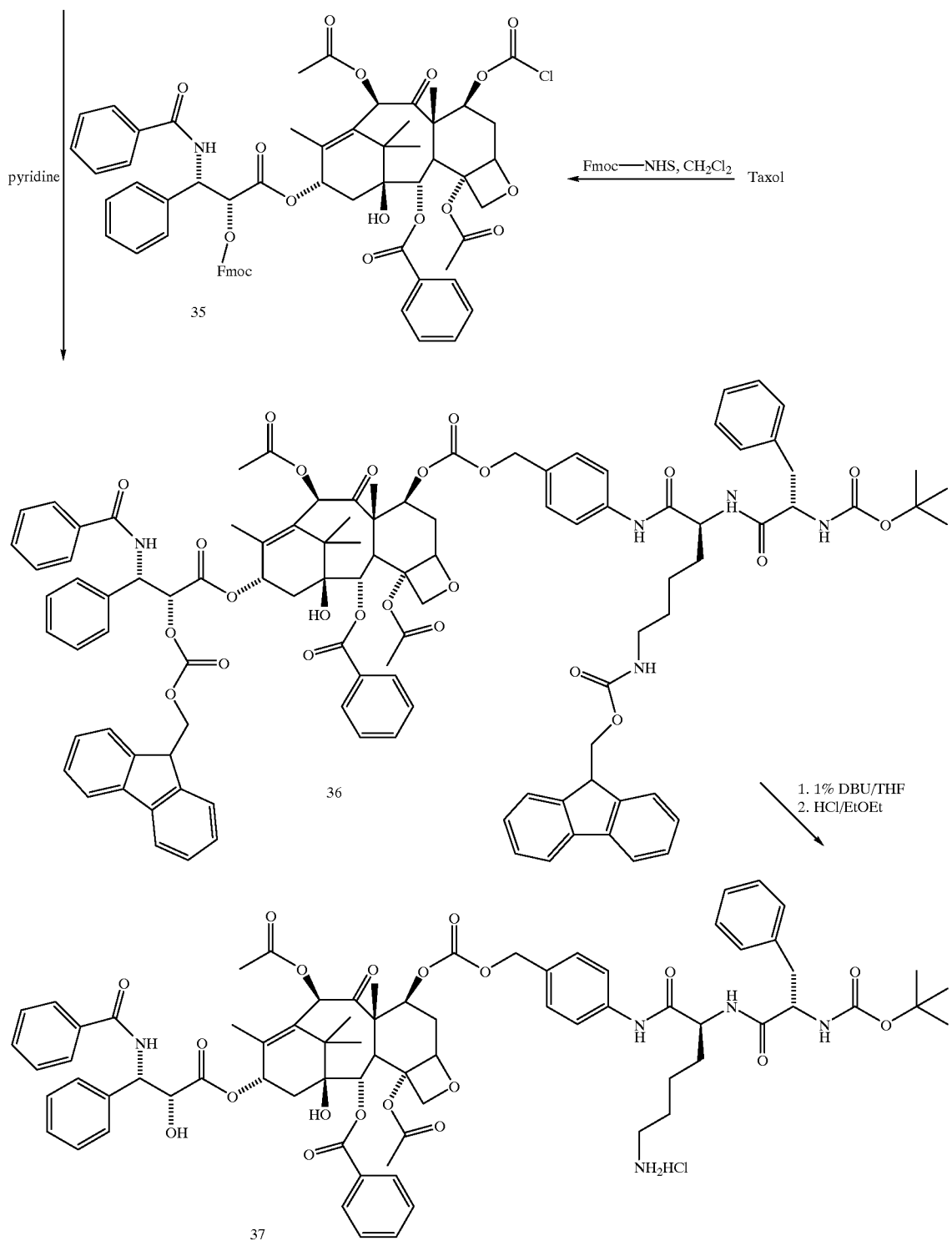

SCHEME 11
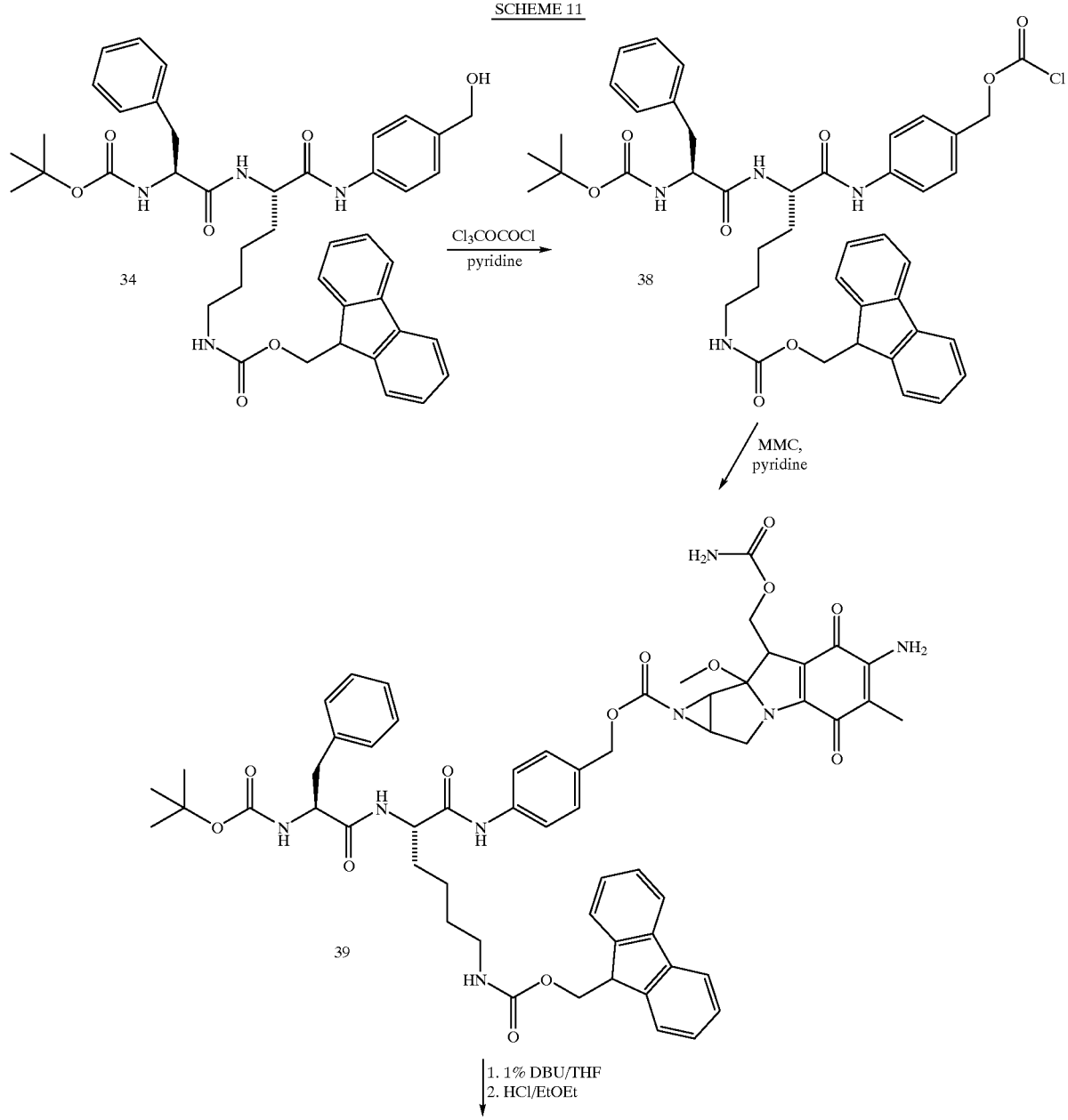

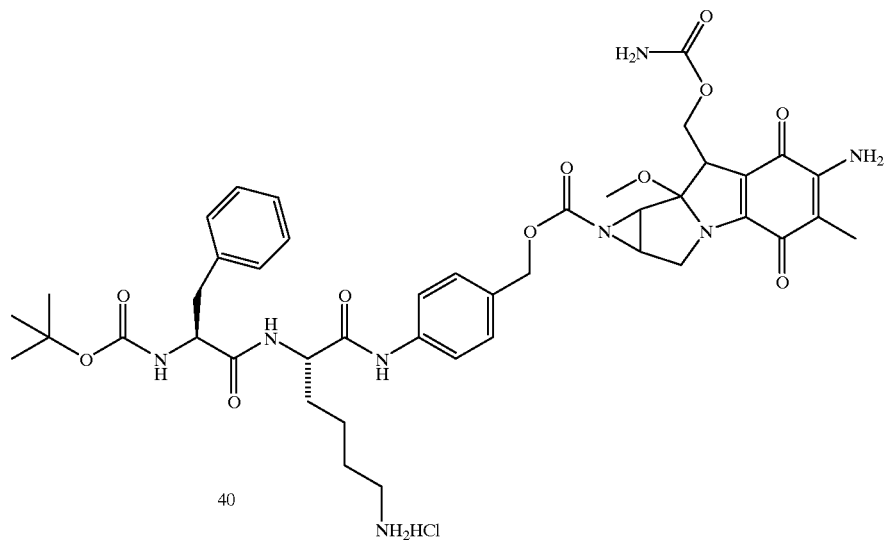
40

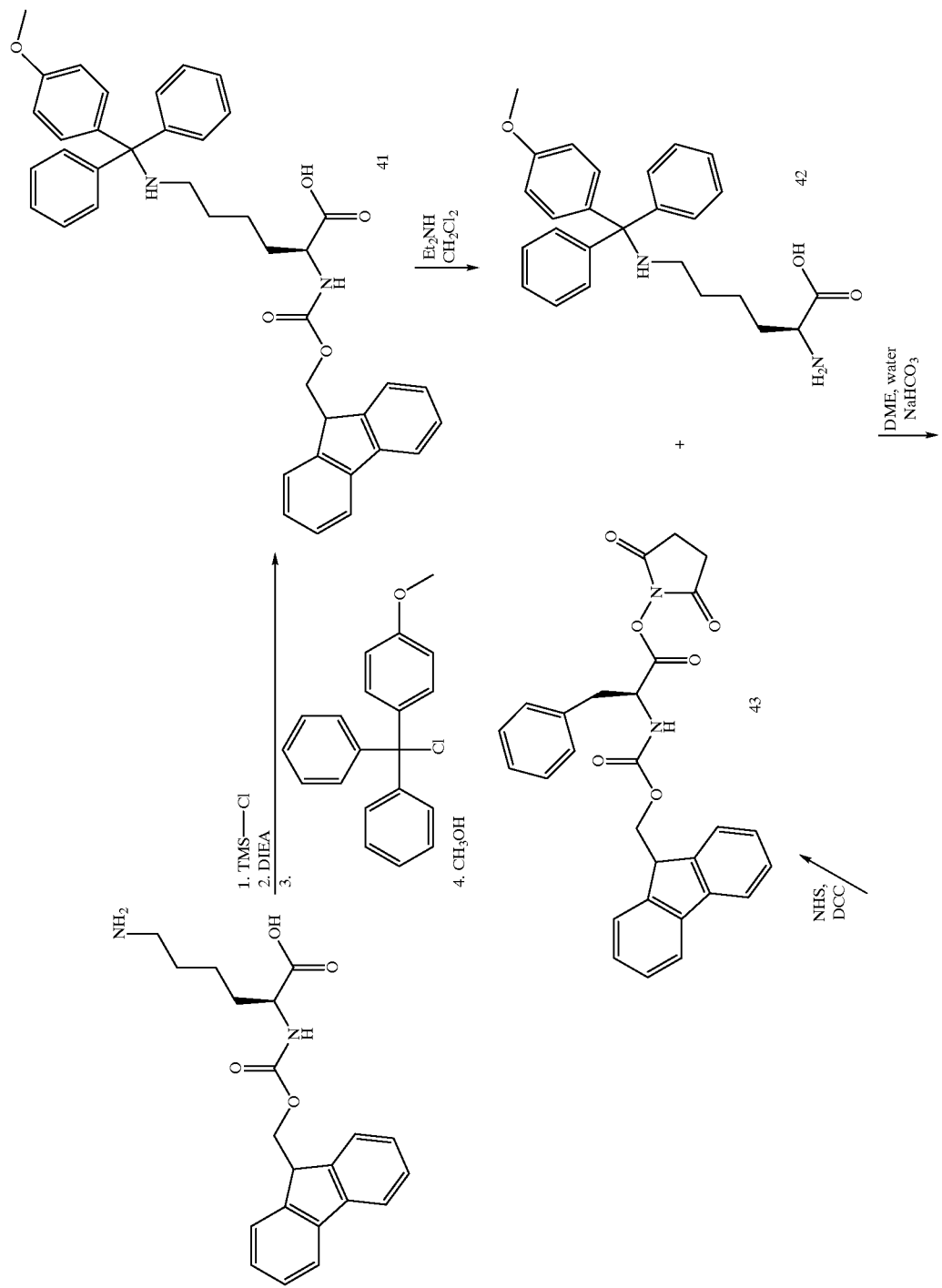
SCHEME 12

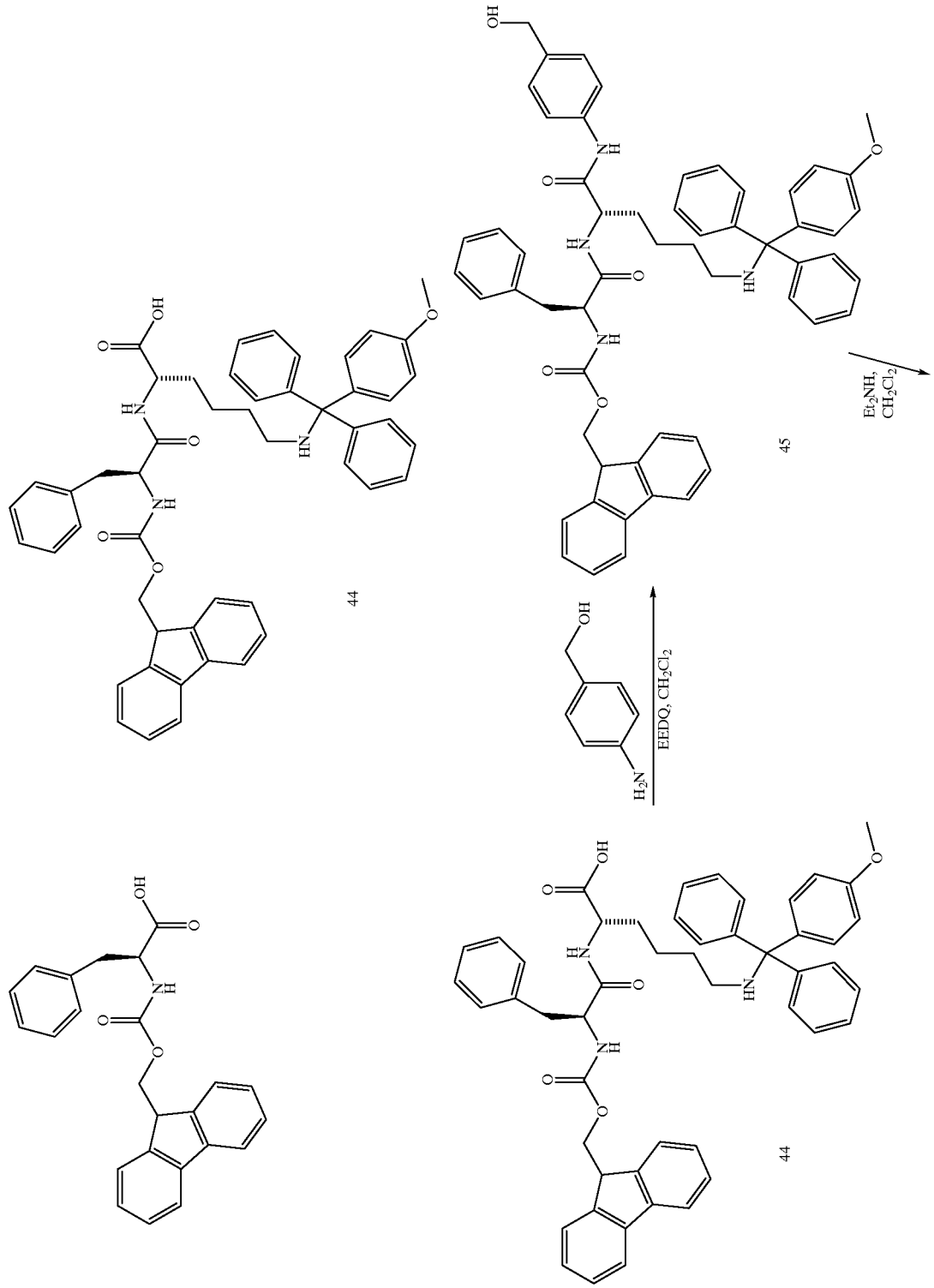

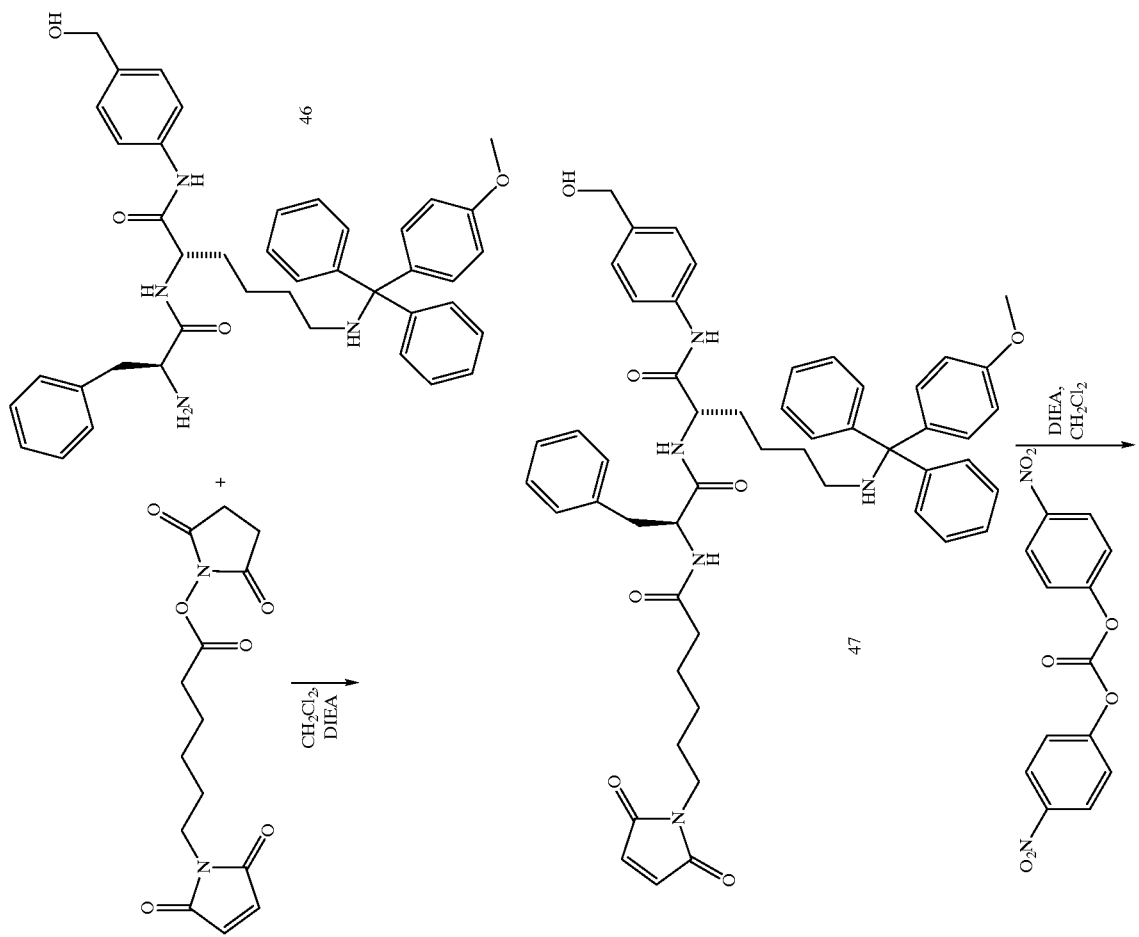

-continued
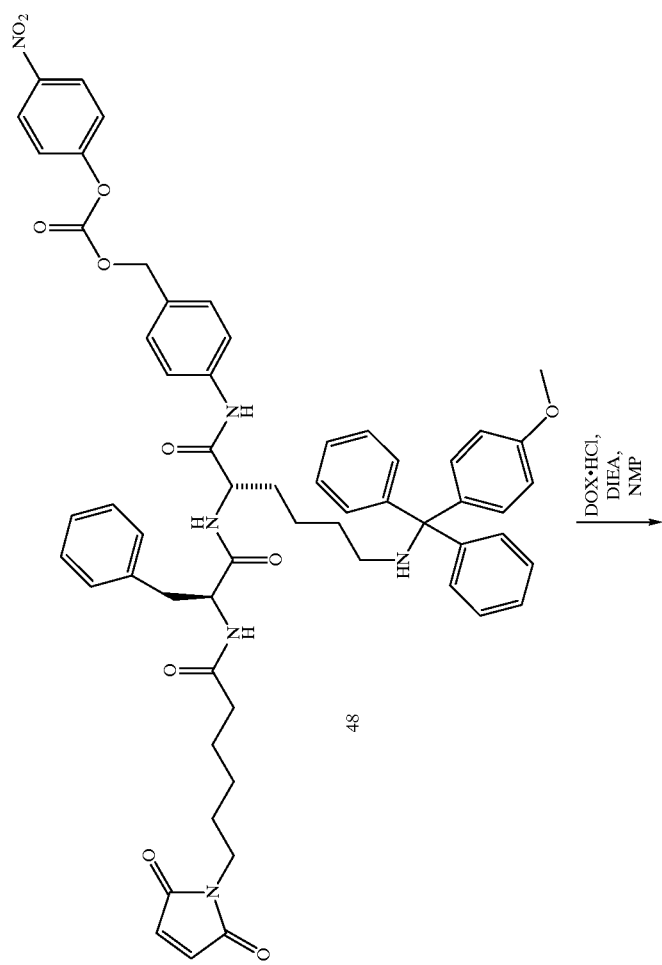
48

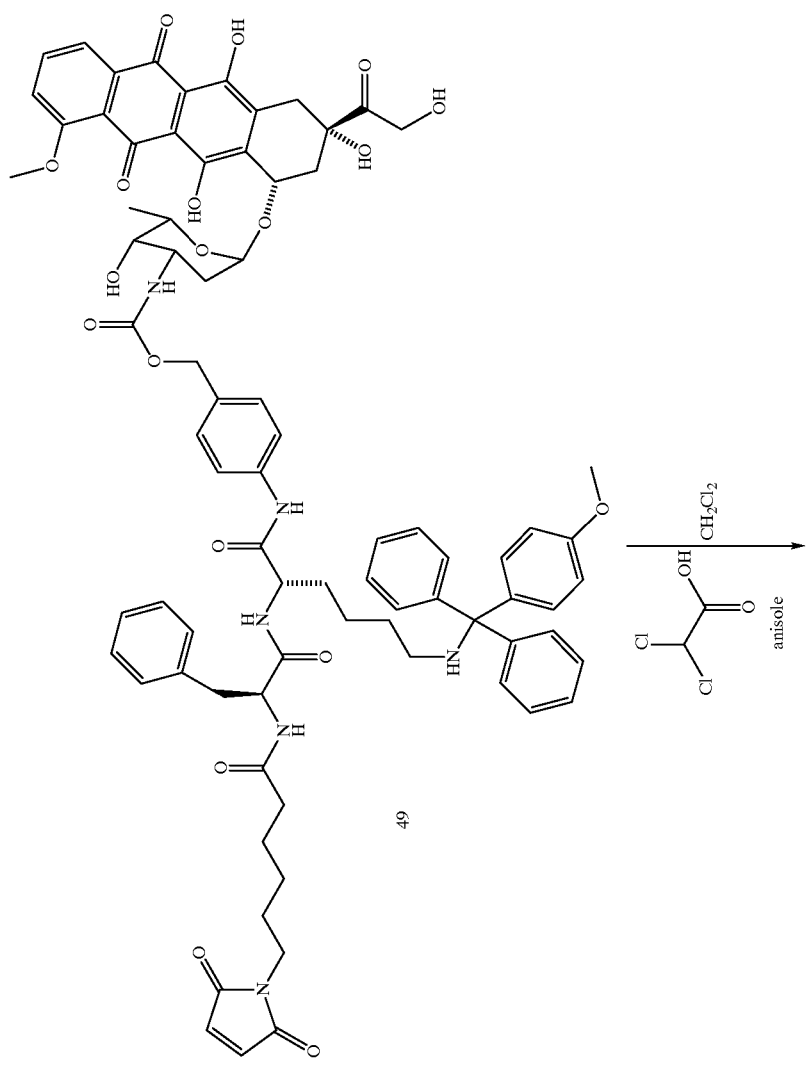

-continued
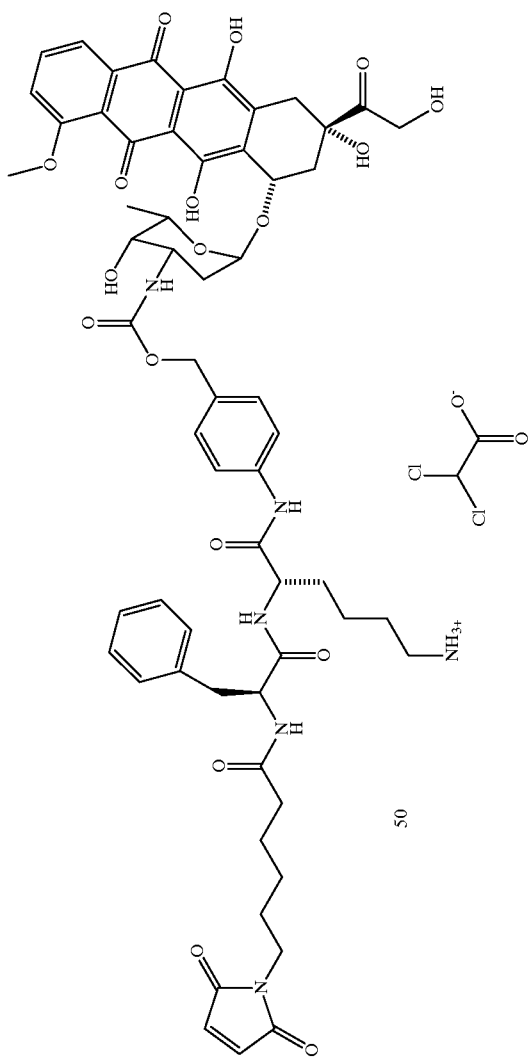
50

SCHEME 13
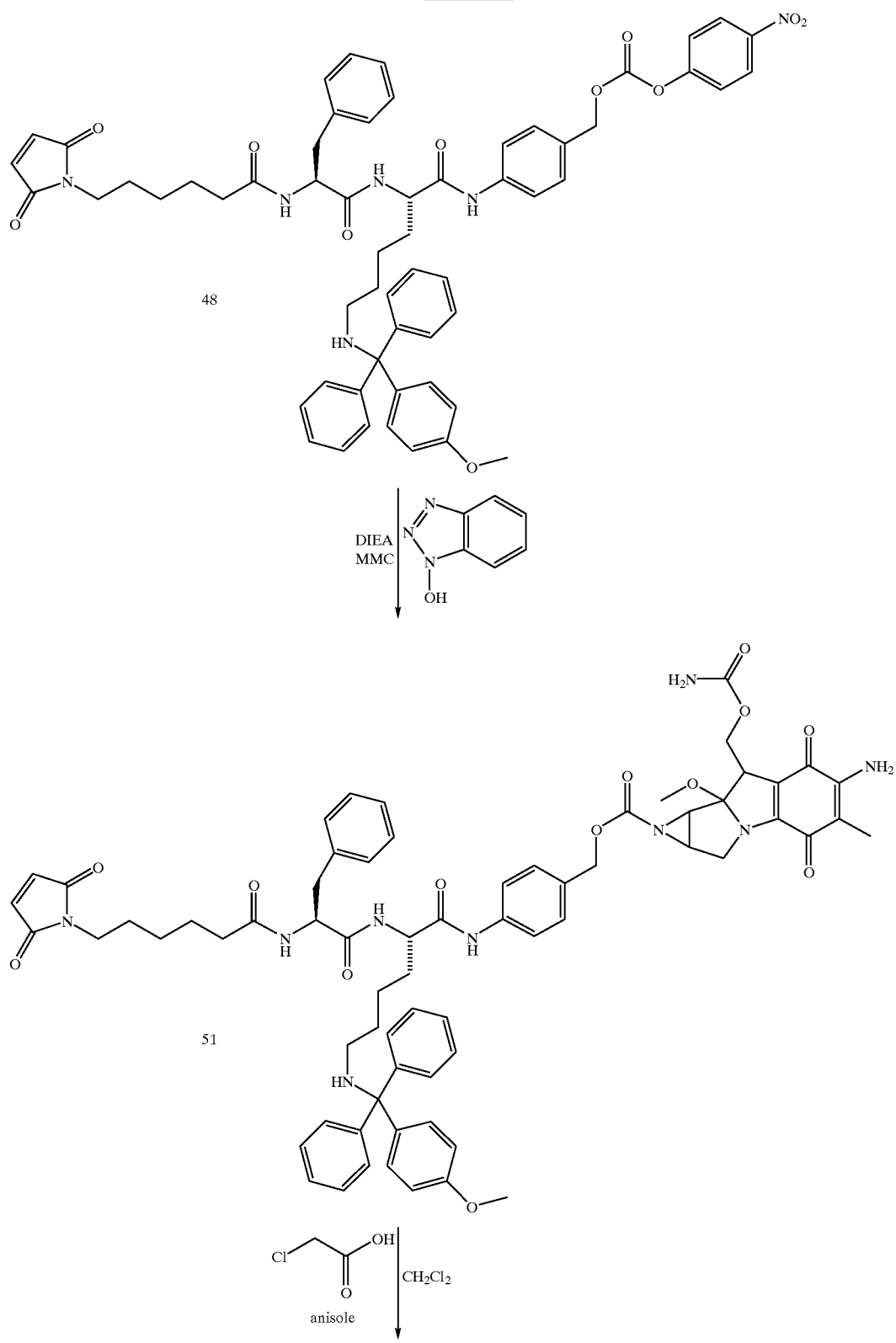

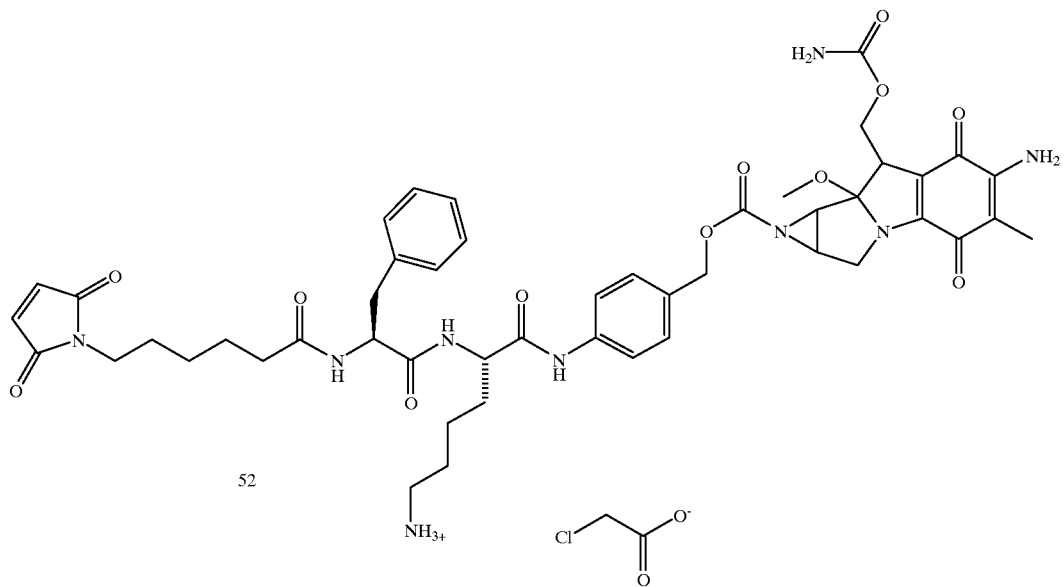
52

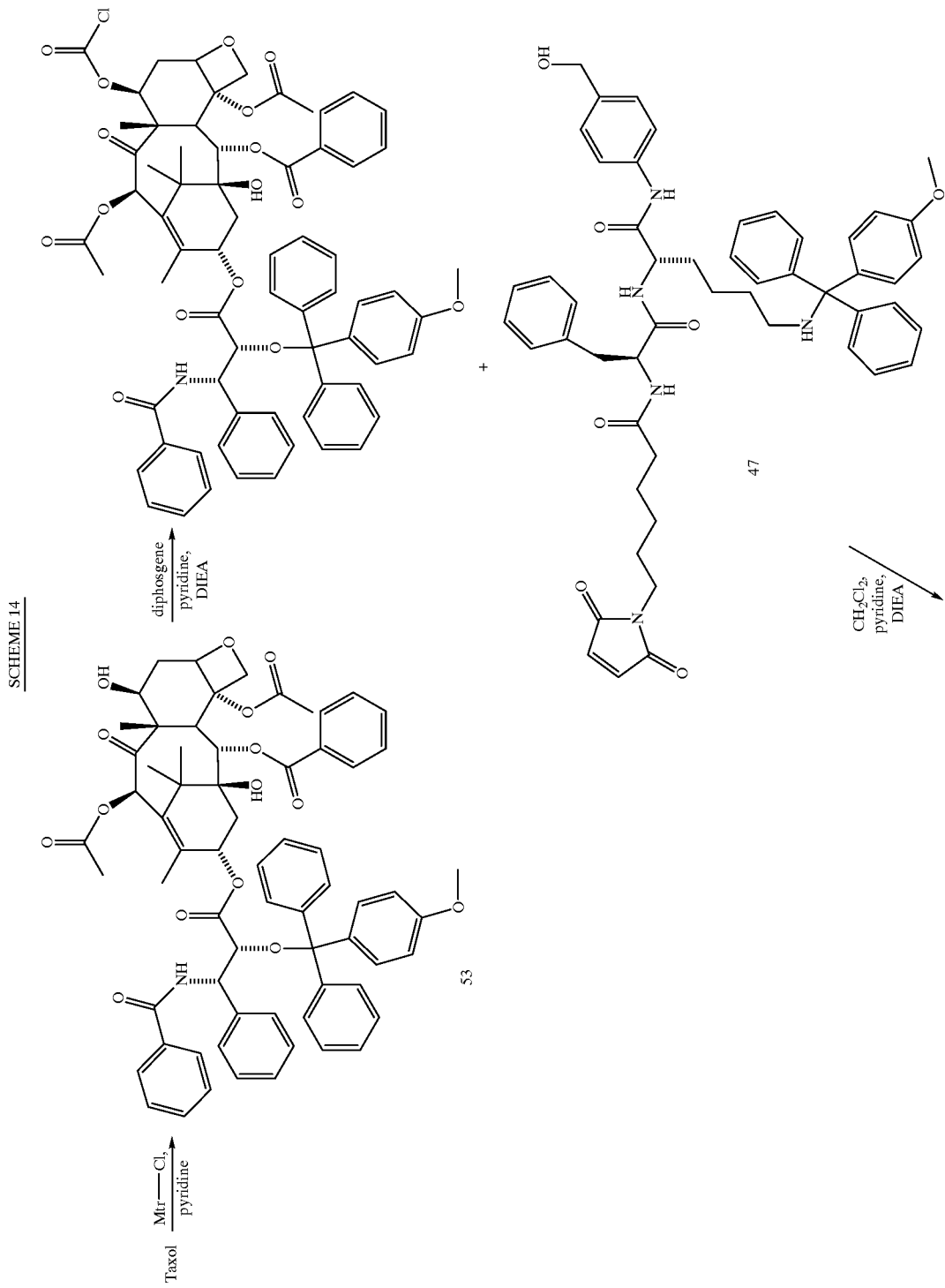
SCHEME 14

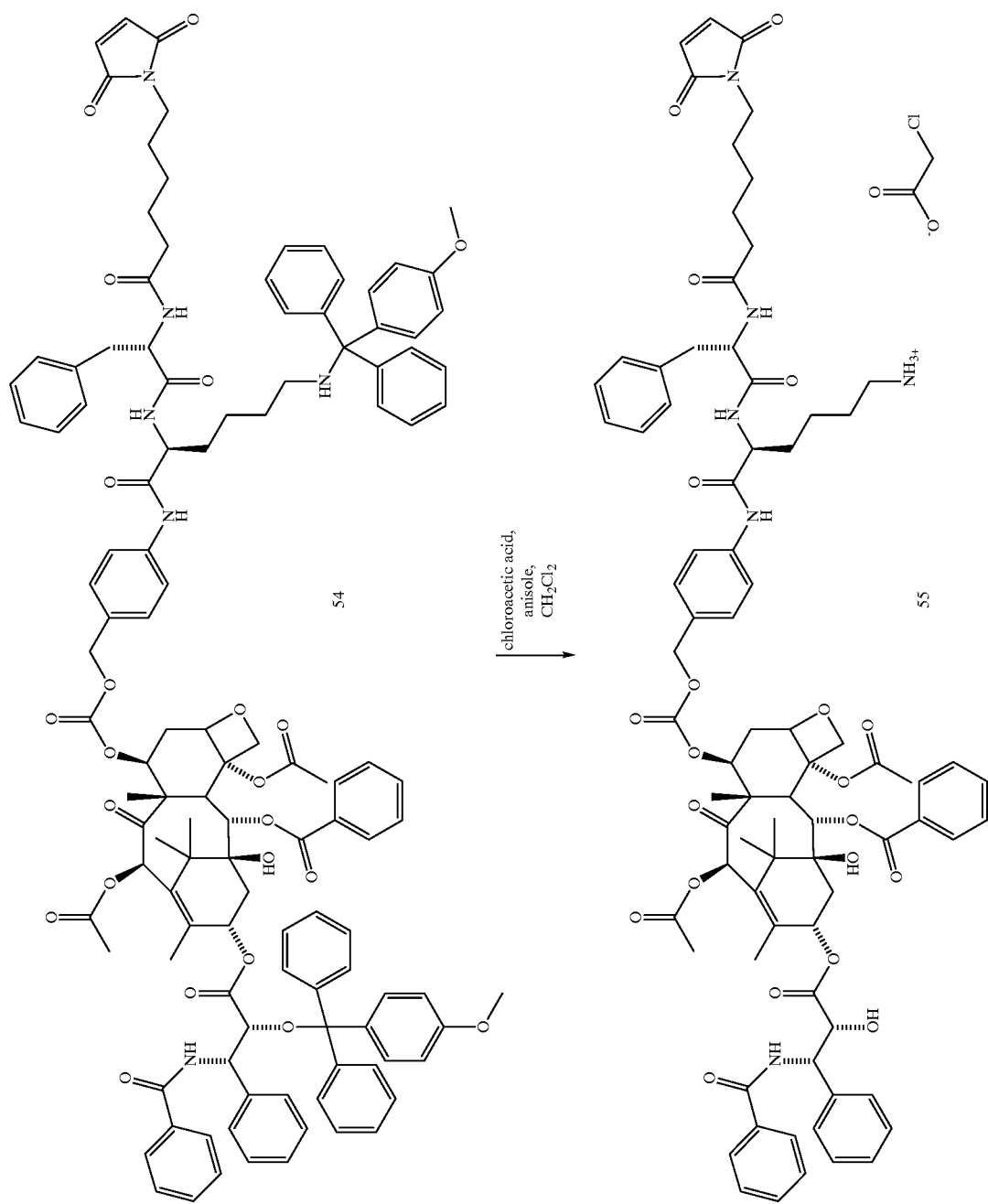

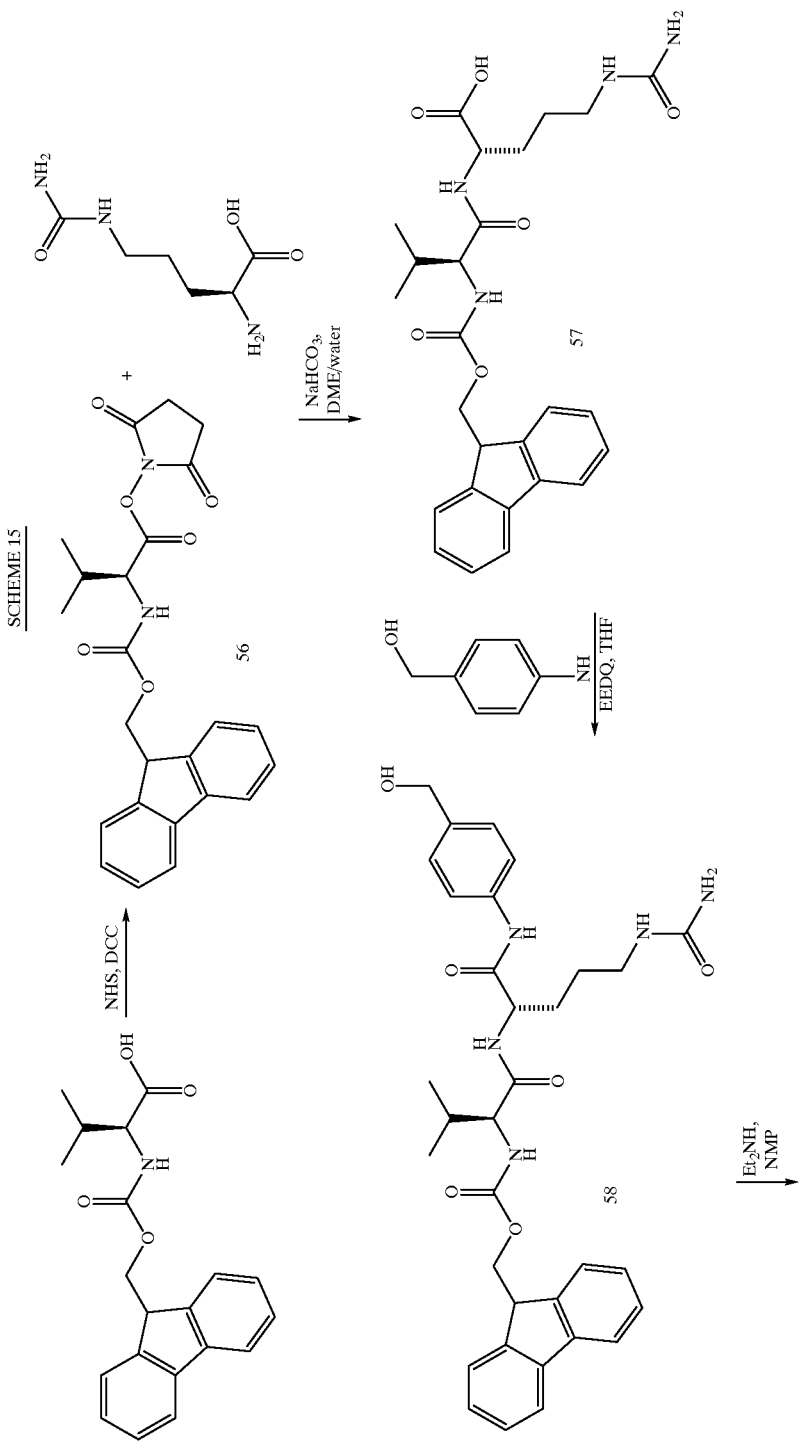

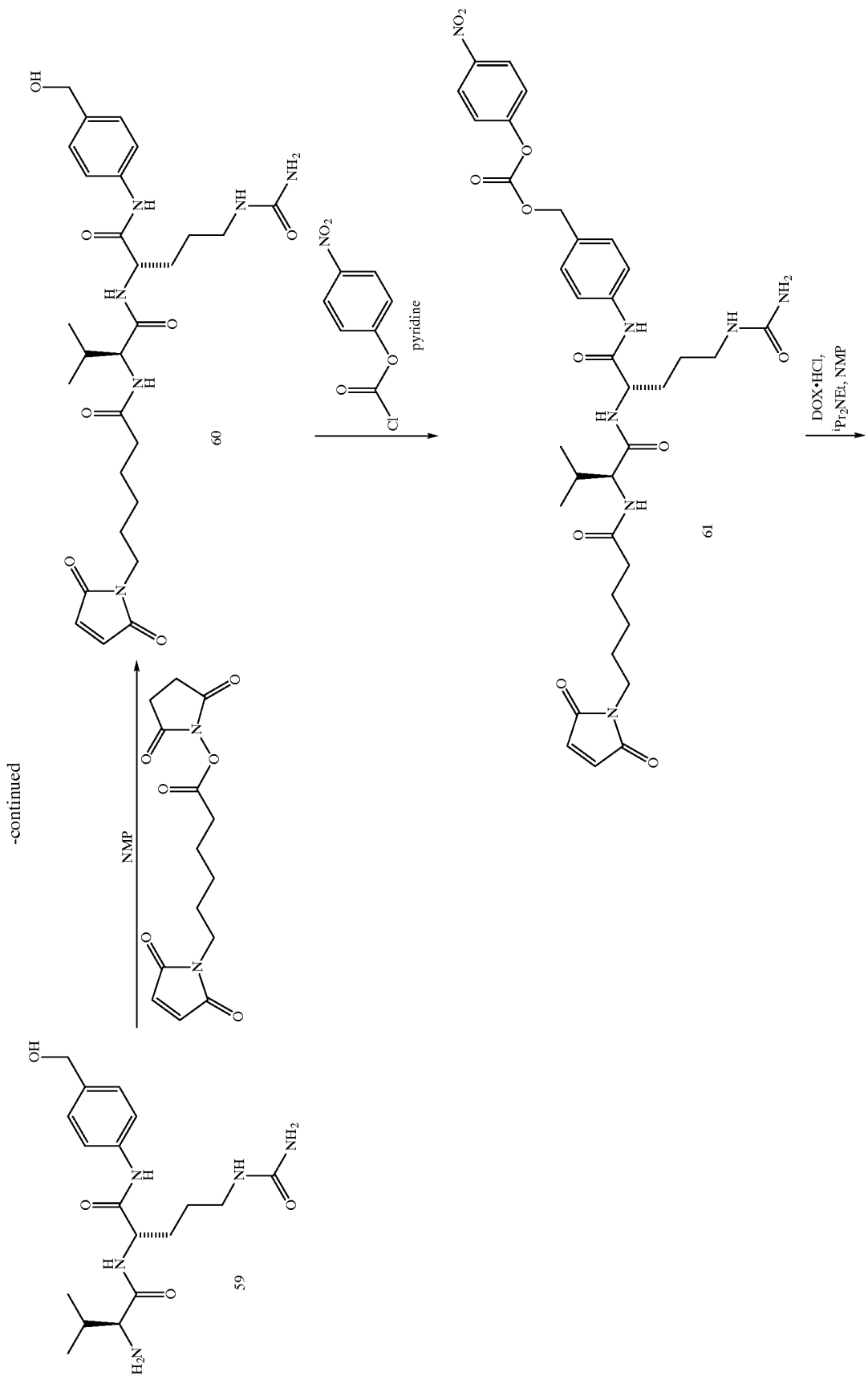

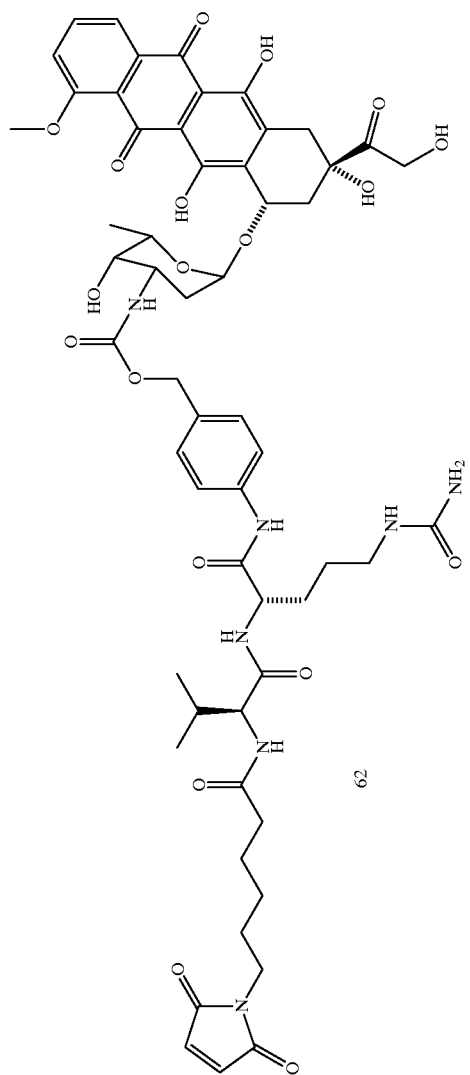
62
-continued

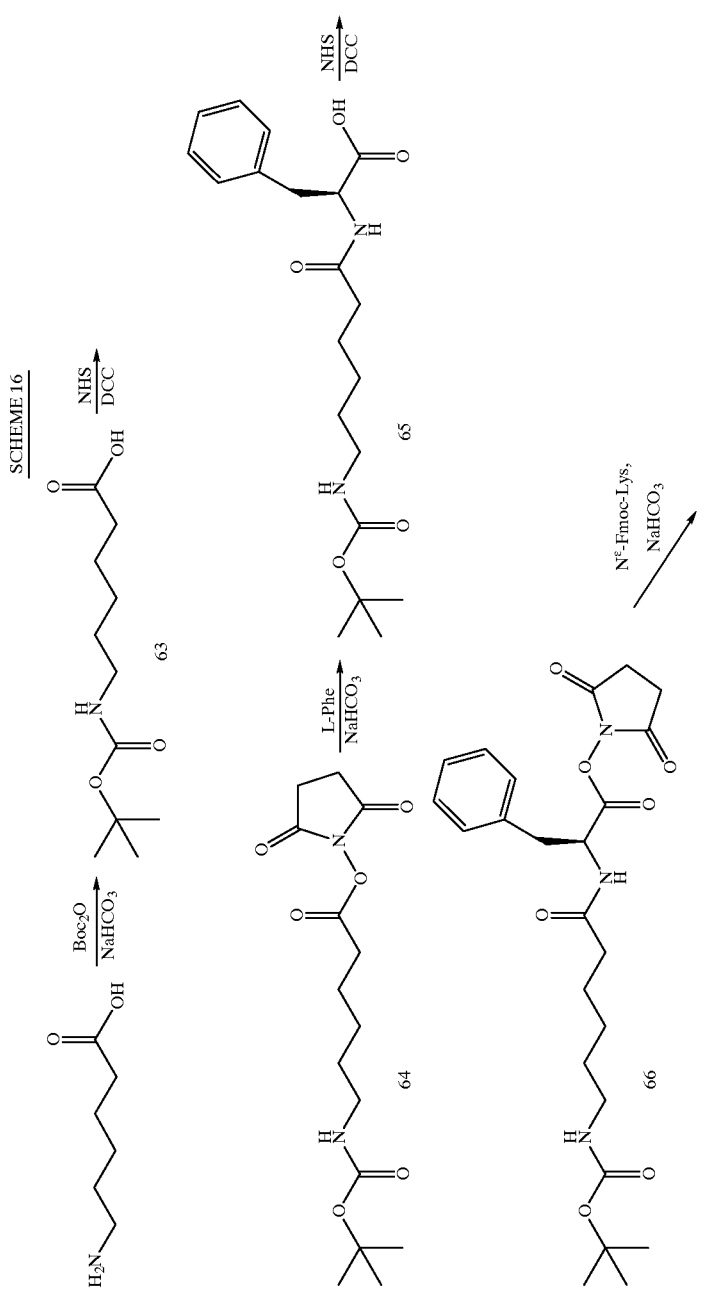

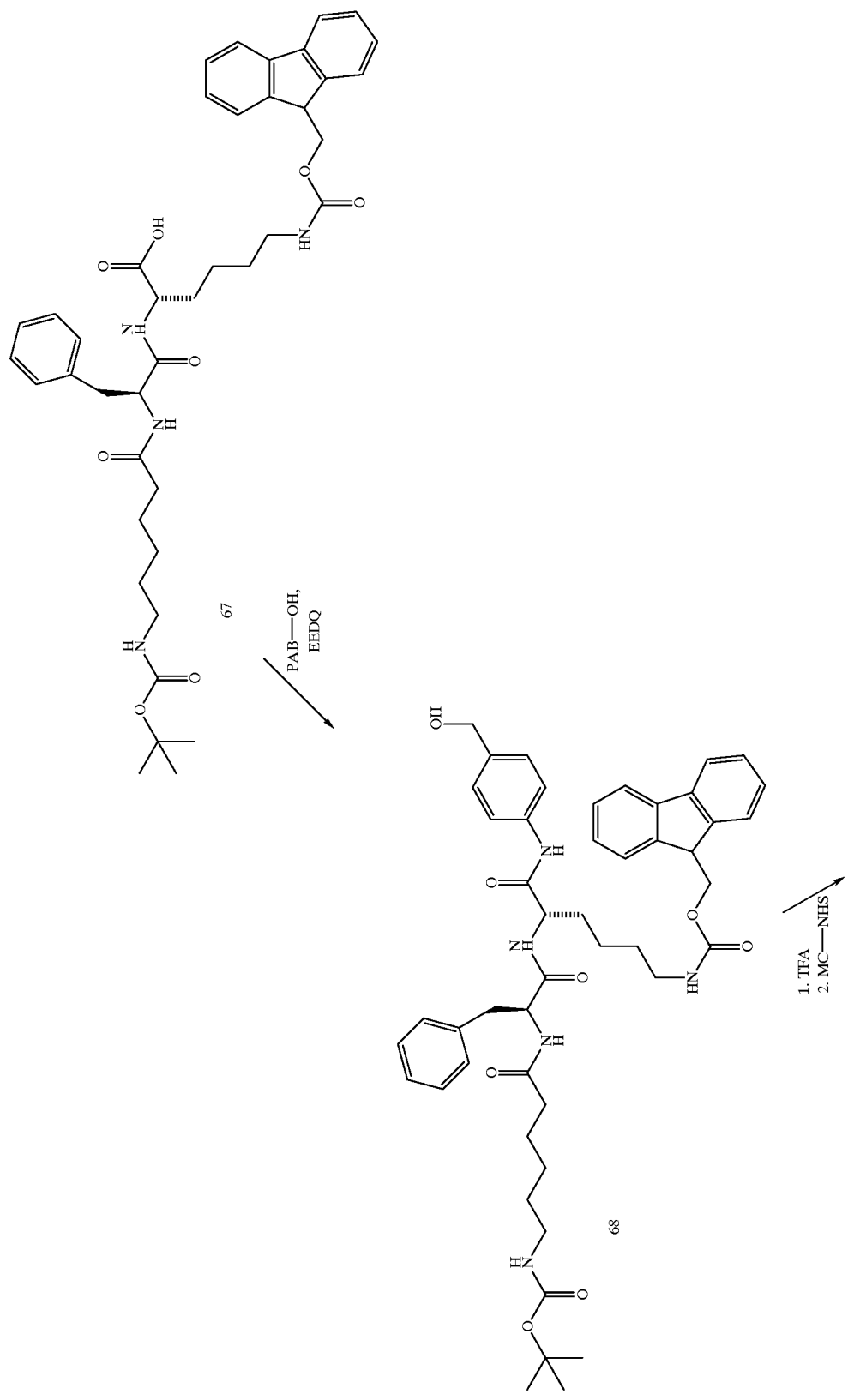

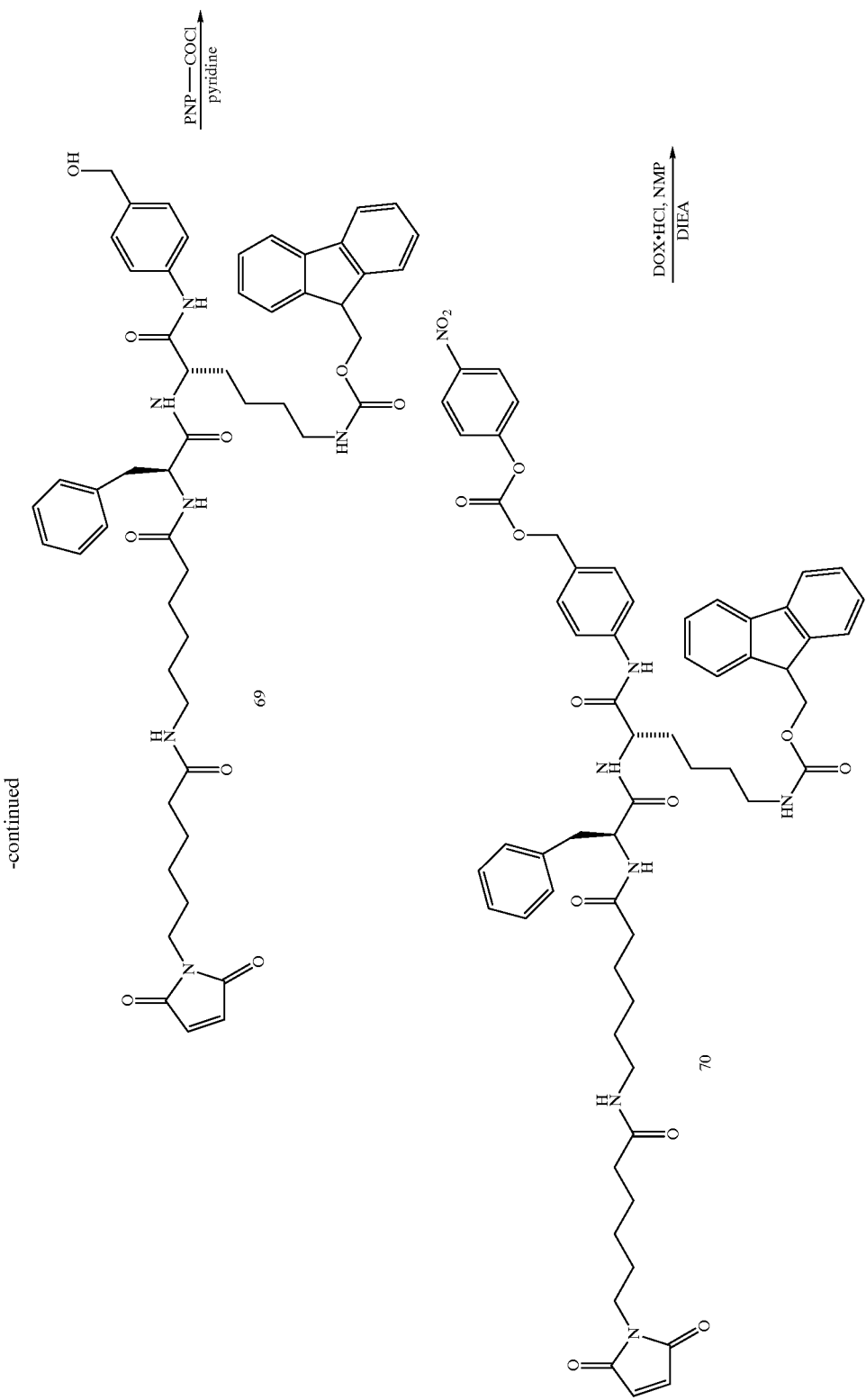

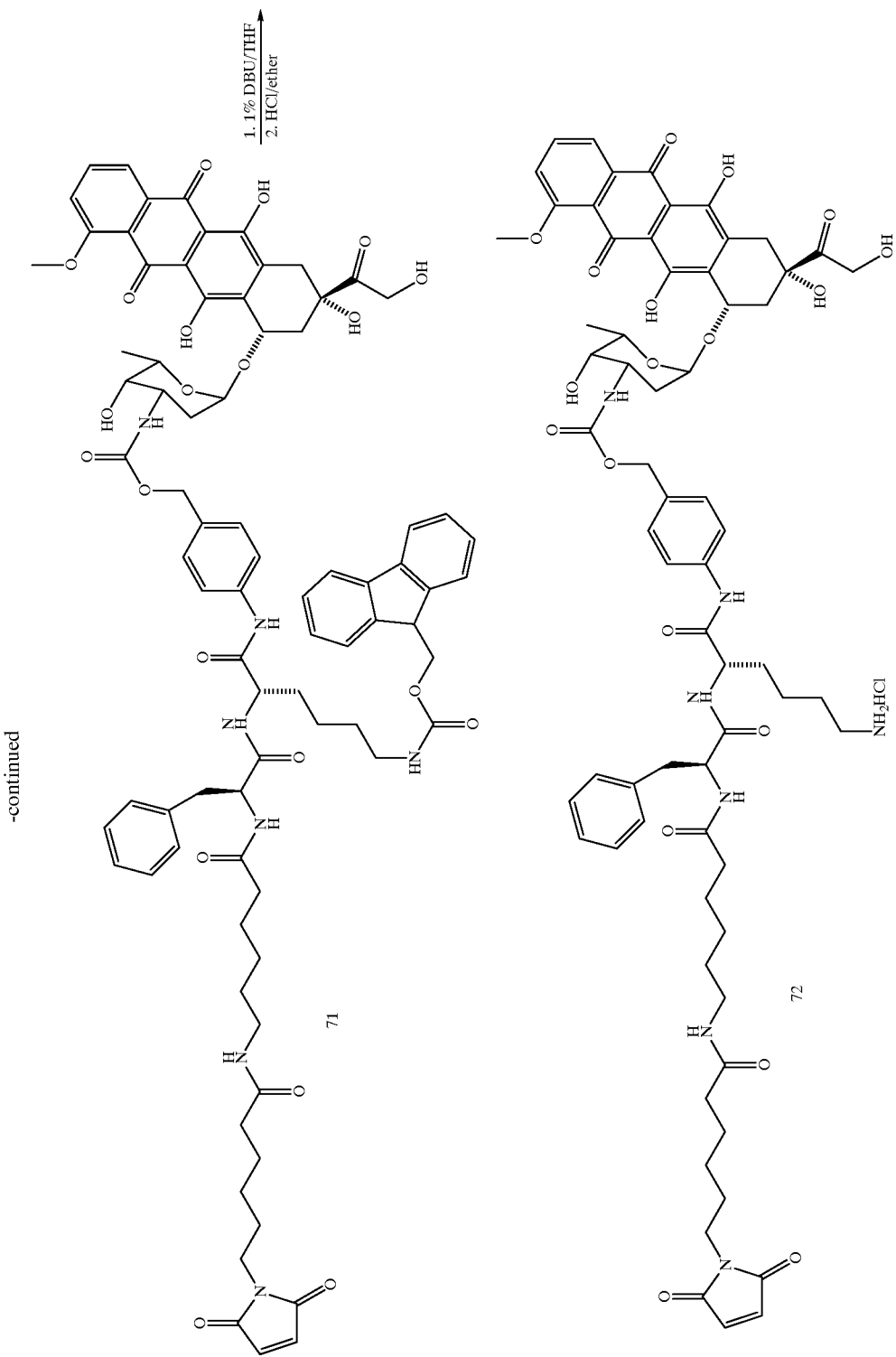

SCHEME 17
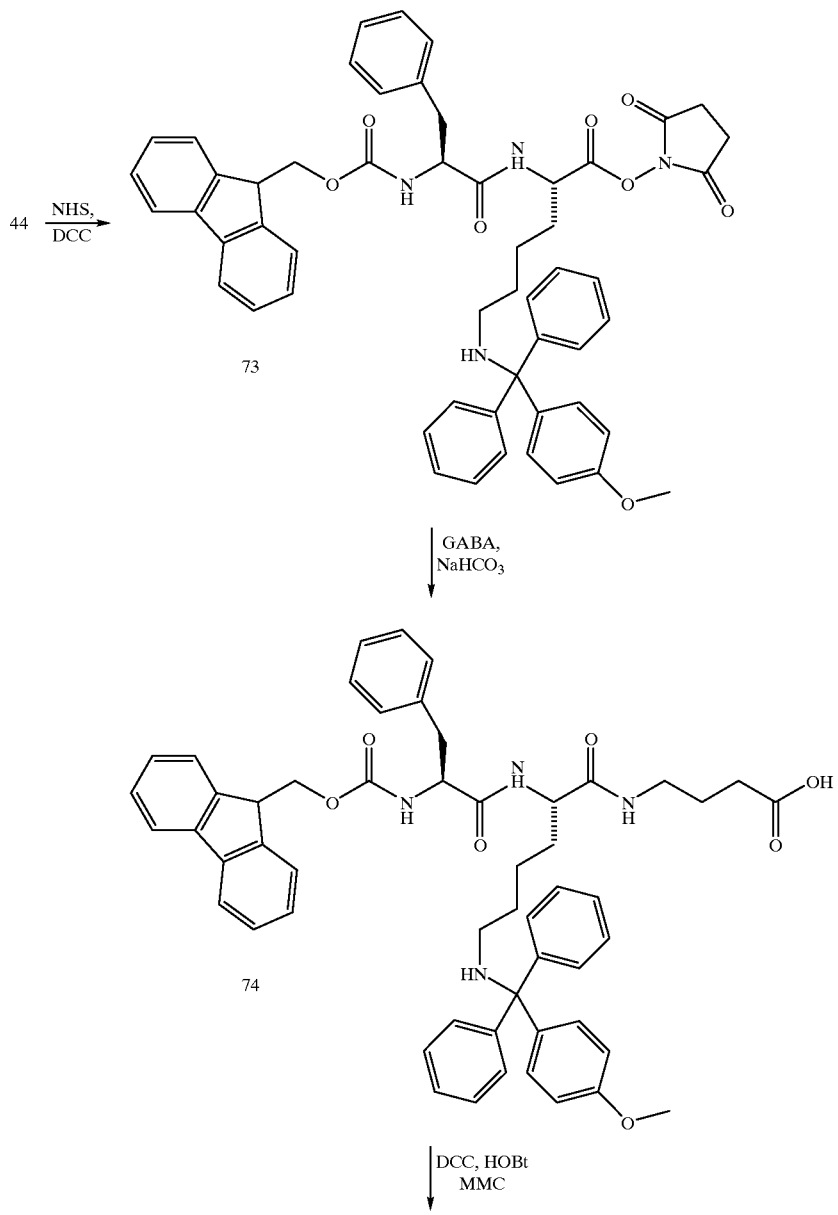

-continued
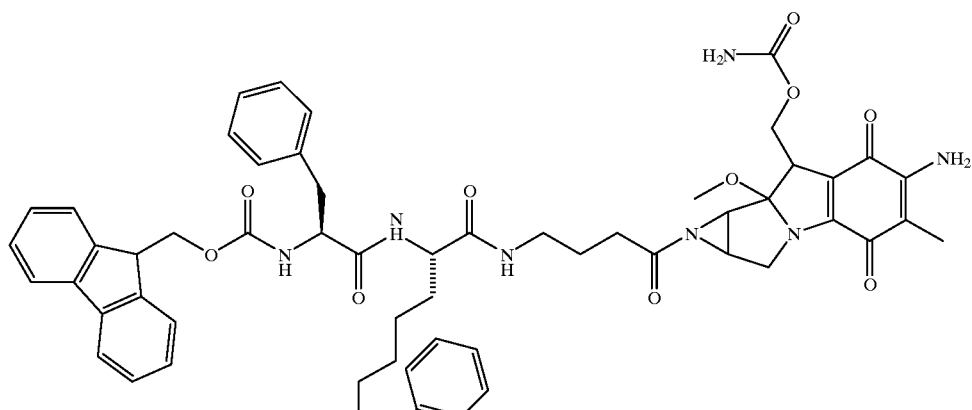
75
Et$_2$NH,
CH$_2$Cl$_2$
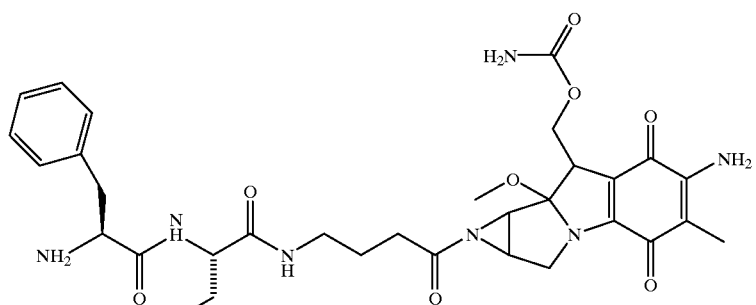
76
MC—NHS,
CH$_2$Cl$_2$ -continued
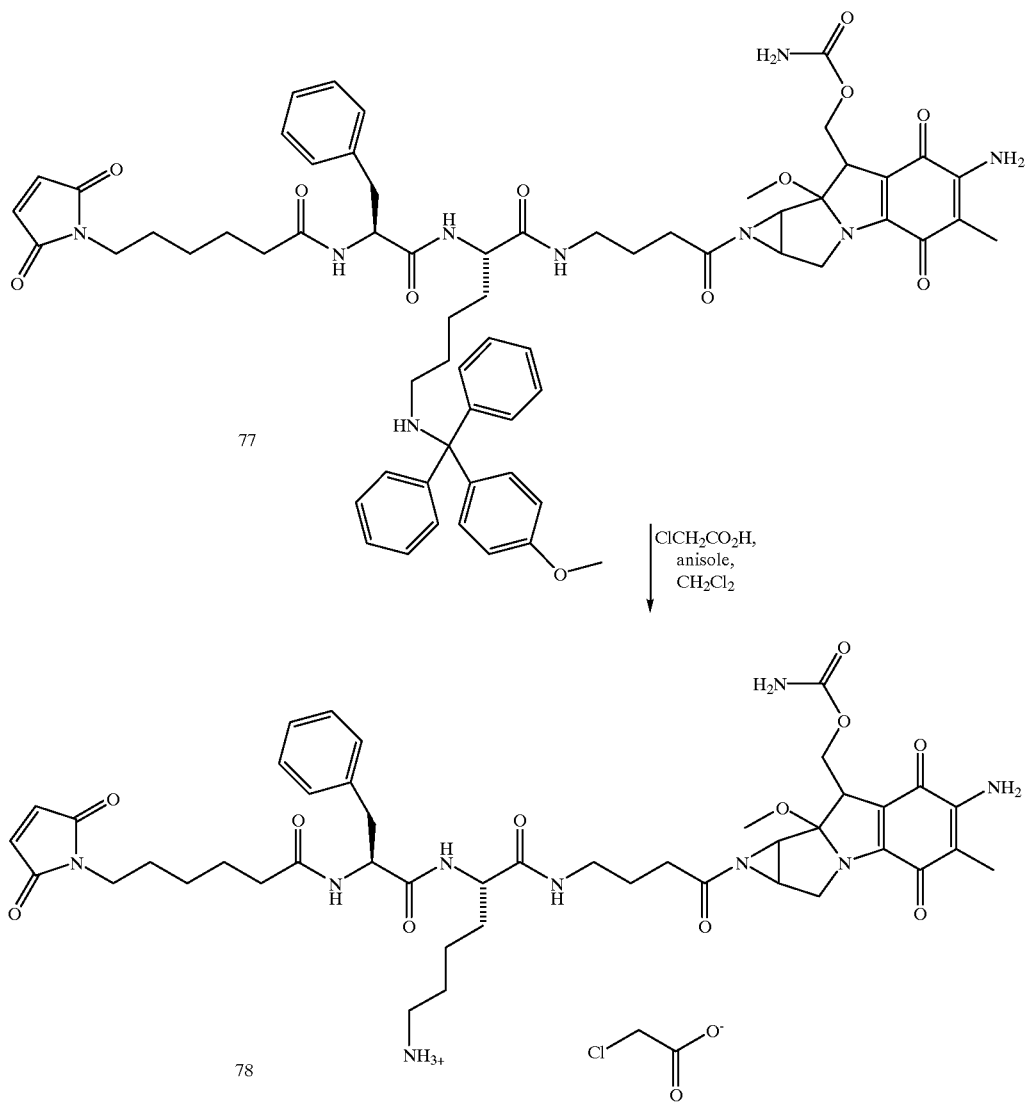
77
78
SCHEME 18
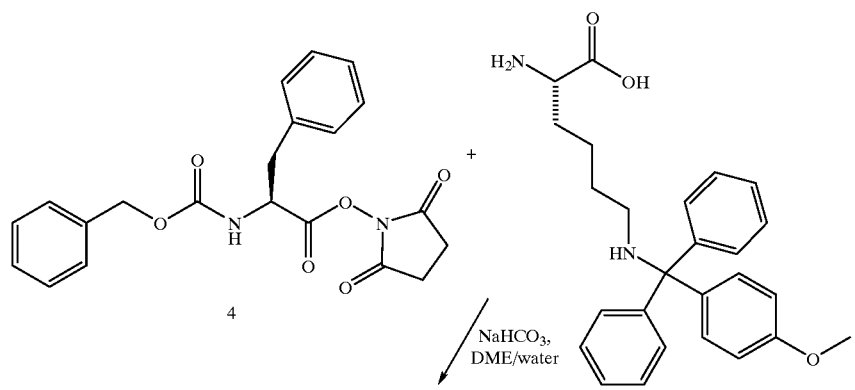
4

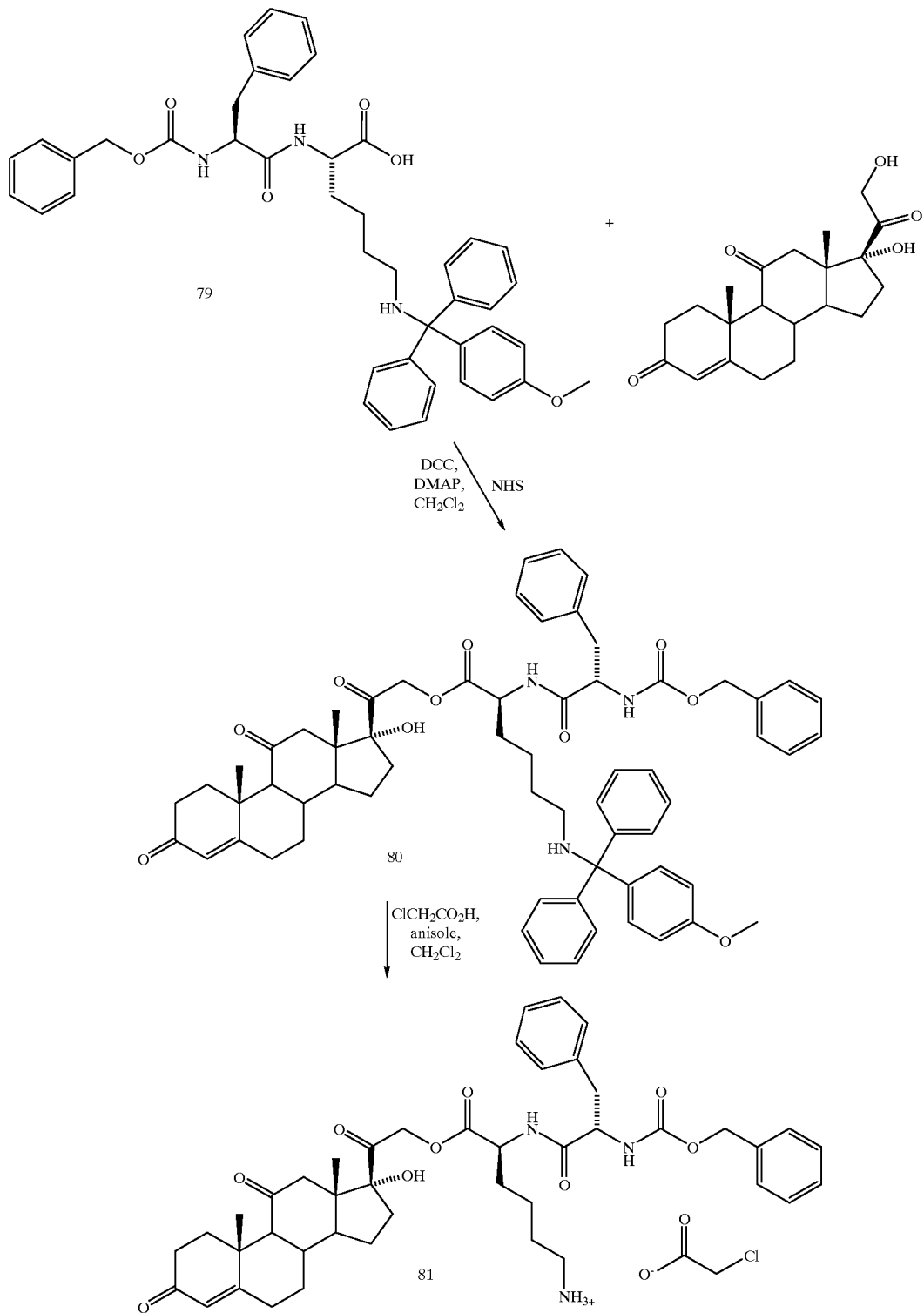

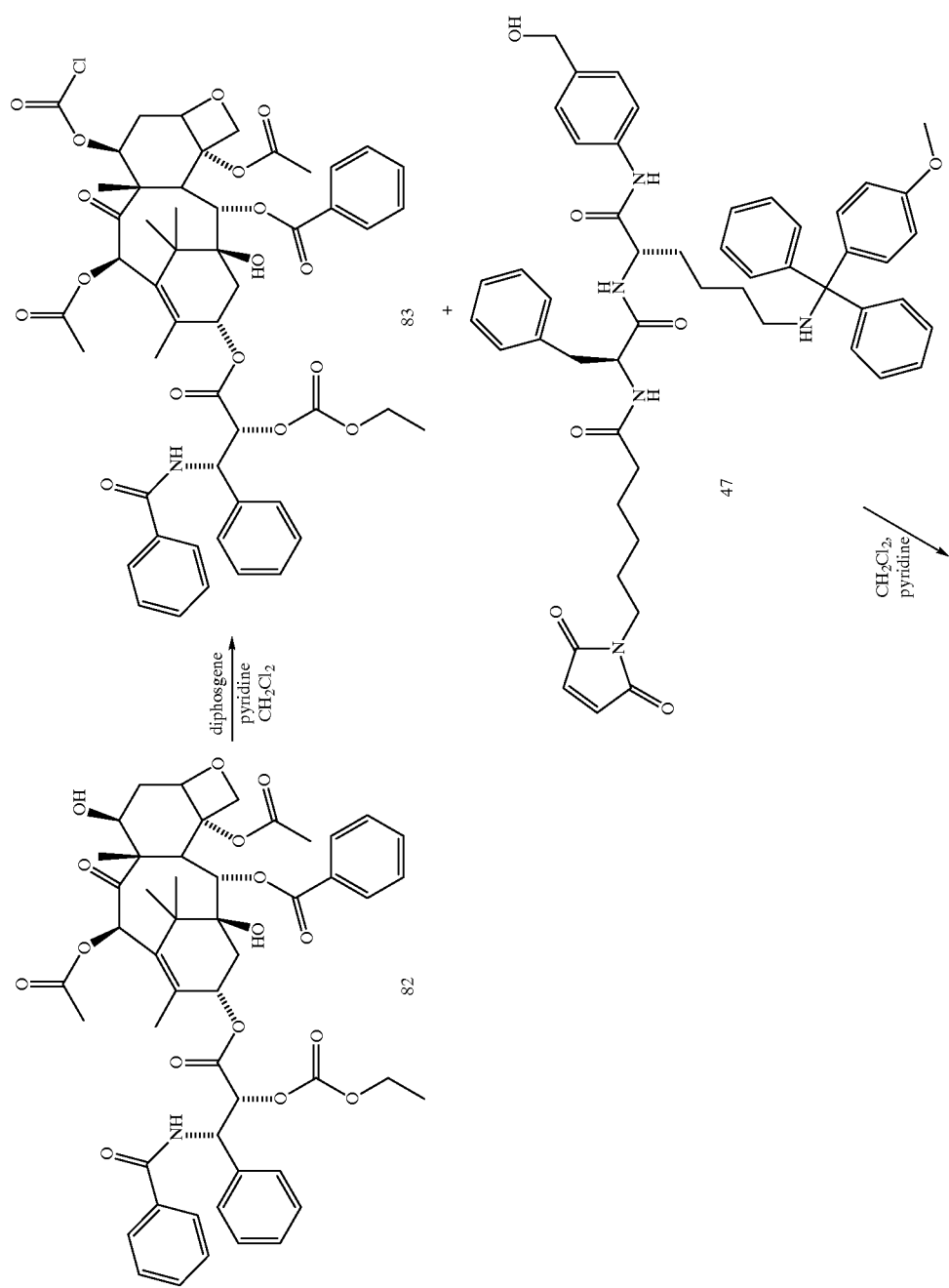
SCHEME 19

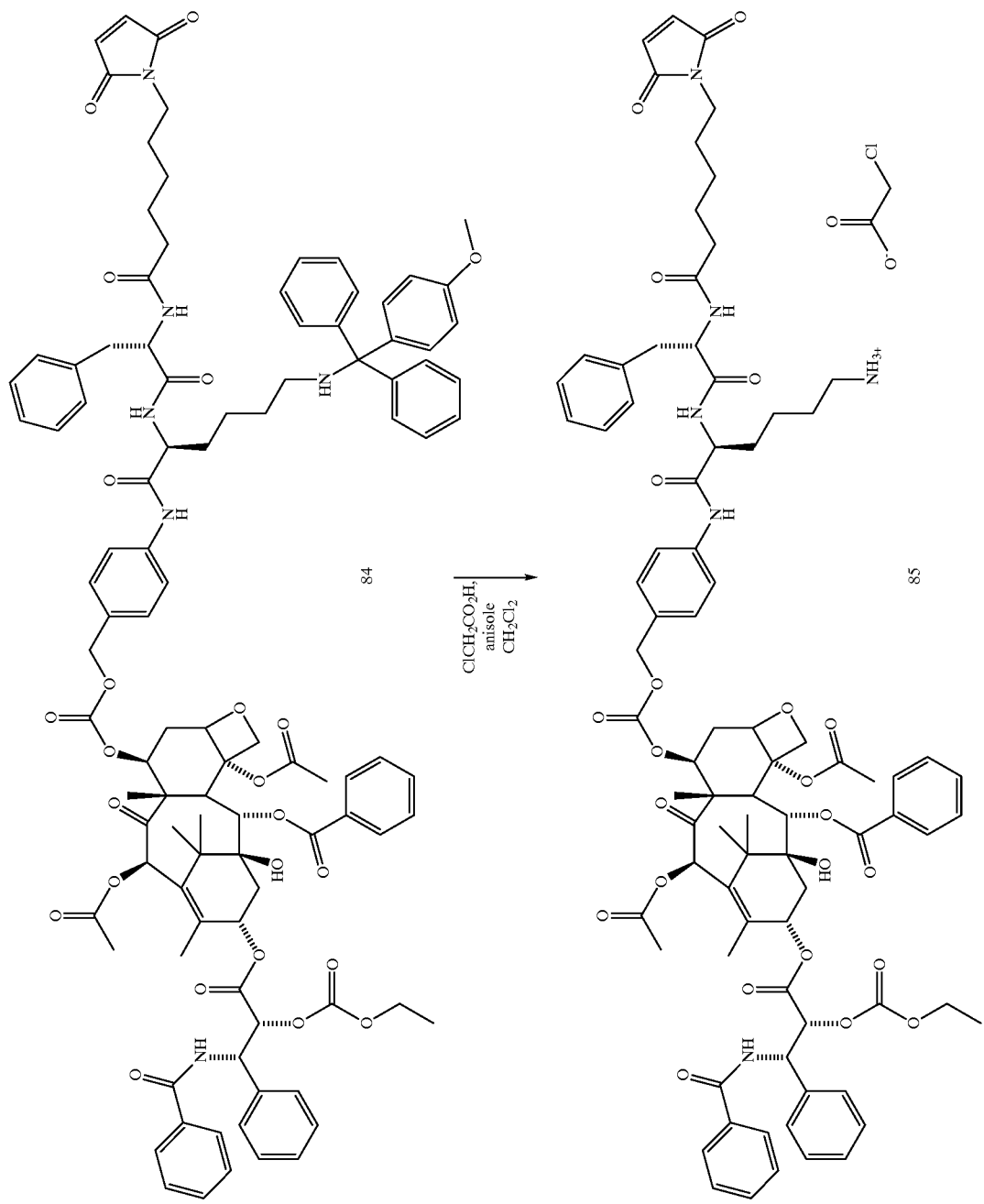

BIOLOGICAL ACTIVITY

Representative conjugates of the present invention were tested in both in vitro and in vivo systems to determine biological activity. In these tests, the potency of conjugates of cytotoxic drugs was determined by measuring the cytotoxicity of the conjugates against cells of human cancer origin. The following describes representative tests used and the results obtained. One skilled in the art will recognize that any tumor line expressing the desired antigen could be used in substitution of the specific tumor lines used in the following analyses.

TEST I

Cathepsin B Release of Free DOX

300 µl of the above conjugate solution was diluted to 1 ml with pH 5.0 acetate buffer (25 mM+1 mM EDTA) giving a final pH of 5.3. This solution was incubated at about 37° C. while 6 µl of cathepsin B solution (see 2 below) was incubated with 20 µl of activating solution (see 2 below) for about 15 minutes at room temperature. The enzyme solution was then treated with the pH 5.3 conjugate solution and the mixture incubated at about 37° C. 25 µl aliquots were removed periodically and diluted with 50 µl of cold methanol to precipitate the protein. The samples were centrifuged and the liquid injected into the HPLC (C-18 column; 80:20 methanol/pH 2.8 triethylammonium formate buffer; 1 ml/min.; 495 mn detection wavelength). Peak areas were calibrated by injection of known concentration of DOX. The half-life of release of free DOX was determined to be about 3 hours with 93% of the theoretical release of DOX accounted for (some free DOX is likely to precipitate out with the protein).

TEST II

Human Plasma Stability

300 µl of conjugate solution was diluted to 1 ml with freshly drawn human plasma and the mixture was incubated at about 37° C. 25 µl aliquots were removed periodically and diluted with 50 µl of cold methanol. The samples were centrifuged and the liquid injected into the HPLC (conditions as above). Separate plasma samples were incubated with 1% and 2% theoretical release of free DOX for several minutes and treated in the same way. Free DOX was successfully detected and quantified at these levels. No free DOX was detected from the conjugate in plasma over 7.5 hours. (half-life>375 hrs.).

TEST III

Cathepsin B Unmasking of Z-Phe-Lys-PABC-DOX

Bovin spleen cathepsin B (Sigma, EC 3.4.22.1, MW ca. 40,000) (10 units) was dissolved in 1 ml pH 5.0 acetate buffer (25 mM acetate+1 mM EDTA), giving a solution roughly 13.7 M. 6 µl of the enzyme solution was incubated with 12 µl of an activating solution (30 mM dithiothreitol and 15 mM EDTA) for about 15 minutes at room temperature. To this was added 2 ml of pH 5.0 acetate buffer (25 mM acetate with 1 mM EDTA) which had been incubated at about 37° C., followed by 8 µl of a 10 mM solution of Z-Phe-Lys-PABC-DOX in methanol ([Substrate]=40 µM, [Cathepsin B]=ca. 41 nM). The mixture was incubated at about 37° C., and aliquots were periodically removed and injected into the HPLC (C-18 column; 80:20 methanol/pH 2.8 triethylammonium formate (50 mM) buffer; 1 ml/min.; 495 mn detection wavelength). The half-life of release of free DOX was determined to be 7–9 minutes.

TEST IV

Human plasma stability

4 µl of a 10 mM solution of Z-Phe-Lys-PABC-DOX was dissolved in 1 ml of freshly drawn human plasma. Aliquots (50 µl) were periodically removed and diluted with cold methanol (100 µl). The samples were centrifuged and the resulting liquid injected into the HPLC (conditions as above). Enough DOX was added to a separate sample of plasma to give a theoretical release of 1% from the substrate. This was successfully detected using the same methods. No free DOX was detected from Z-Phe-Lys-PABC-DOX in plasma over 7 hours (half-life>350 hrs.)

TEST V

Materials and Methods

Human Tumor Cell Lines.

L2987 is a lung adenocarcinoma line obtained from I. Hellstrom (Bristol-Myers Squibb, Seattle, Wash.). The HCT116 colorectal tumor line was obtained from M. Brattain (Baylor Inst., Tex.). A2780 is an ovarian carcinoma line obtained from K. Scanlon (National Cancer Institute).

Binding Assays.

Binding assays were performed by indirect immunofluorescence. Briefly, target cells were harvested in logarithmic phase using trypsin/EDTA (GIBCO, Grand Island, N.Y.) in PBS. The cells were washed twice in PBS containing 1% bovine serum albumin (BSA, Sigma Chemical Co., St. Louis, Mo.) and resuspended to $1 \times 10^7$/ml in PBS containing 1% BSA and 0.1% $NaN_3$ Cells (0.1 ml) were mixed with various antibodies (0.1 ml at 40 ug MAb/ml) and incubated for about 45 minutes at about 4° C. The cell were washed 2× in and resuspended in 0.1 ml of an appropriate concentration of rabbit anti-human IgG (Cappel Laboratories, Cochranville, Pa., Fab'2 fragment). Cells were incubated for about 30 minutes at about 4° C., washed 2× and kept on ice until analyzed on a Coulter EPICS 753 fluorescence-activated cell sorter. Data are expressed as fluorescence intensity (FI): the mean channel number of specific minus control antibody.

In vitro cytotoxicity assays.

Monolayer cultures of human carcinoma cells were harvested using trypsin-EDTA (GIBCO, Grand Island, N.Y.), and the cells counted and resuspended to $1 \times 10^5$/ml in RPMI-1640 containing 10% heat inactivated fetal calf serum (RPMI-10% FCS). Cells (0.1 ml/well) were added to each well of 96 well microtiter plates and incubated overnight at about 37° C. in a humidified atmosphere of 5% $CO_2$. Media was removed from the plates and serial dilutions of DOX or MAb-DOX conjugates added to the walls. All dilutions were performed in quadruplicate. Cells were exposed to DOX or MAb-DOX conjugates for about 2 hours at about 37° C. in a humidified atmosphere of 5% $CO_2$. Plates were then centrifuged (200×g, 5 min.), the drug or conjugate removed, and the cells washed 3× with RPMI-10% FCS. The cells were cultured in RPMI-10% FCS (37° C., 5% $CO_2$) for an additional 48 hours. At this time the cells were pulsed for about 2 hours with 1.0 uCi/well of $^3$H-thymidine (New England Nuclear, Boston, Mass.). The cells were harvested onto glass fibre mats (Skatron Instruments, Inc., Sterling, Va.), dried, and filter bound $^3$H radioactivity determined (β-Plate scintillation counter, Pharmacia LKB Biotechnology, Piscataway, N.J.). Inhibition of $^3$H-thymidine uptake was determined by comparing the mean CPM for treated samples with that of the mean CPM of the untreated control.

Results

Binding Assays:

The L2987, A2780 and HCT116 human carcinoma lines were evaluated for the expression of the BR96 antigen using direct immunofluorescence. As shown in FIG. 1, the L2987 lung line (A) expressed the greatest density of the BR96 antigen (FI=172.8), the A2780 ovarian line (B) expressed BR96 at a lower density (FI=103.2), and the HCT116 colon line (C) did not express significant amounts of the BR96 antigen (FI=0).

Figure 2B:
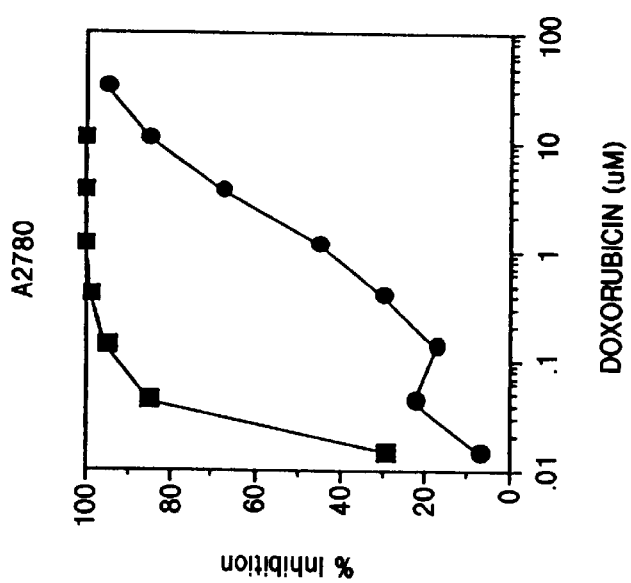
FIG. 2B shows the potency of the BR96-doxorubicin conjugate and the unconjugated doxorubicin in the A2780 ovarian line.
Figure 2C:
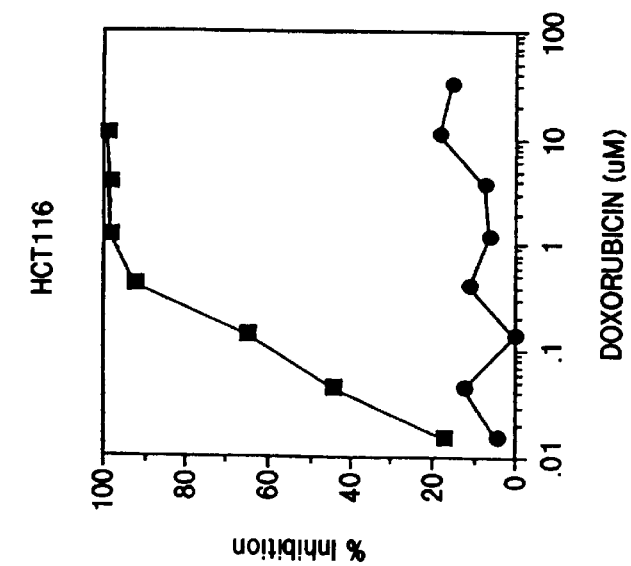
FIG. 2C shows the potency of the BR96-doxorubicin conjugate and the unconjugated doxorubicin in the HCT116 colon line.

Cytoxicity of BR96-DOX peptide linked conjugate:

The in vitro potency of the BR96-DOX peptide immunoconjugate was evaluated in parallel against the L2987, A2780, and HCT116 human carcinoma lines. As described above these cells express various densities of the BR96 antigen (L2987>A2780>>HCT116). Unconjugated doxorubicin was also evaluated. As shown in FIG. 2, the potency of the BR96-DOX conjugate was equivalent to that of unconjugated DOX against the L2987 lung line (A). The BR96-DOX conjugate was approximately 50 fold less potent than unconjugated DOX against the A2780 ovarian line (B). The BR96-DOX conjugate was not active against the antigen-negative HCT116 line (C). However, as shown this line was sensitive to unconjugated DOX. These data demonstrate the direct relationship between the in vitro potency of the BR96-DOX conjugate and the epitope density of the BR96 antigen. In summary the BR96-DOX conjugate demonstrates antigen-specific cytotoxicity in vitro and the potency of the conjugate is related to the density of BR96 antigen expressed by various cell lines.

TEST VI

The BR96-PEP-DOX conjugate (MR=4.41) was evaluated in vivo (Table 1) against L2987 human lung carcinoma xenografts. Therapy was initiated 14 days after tumor implant when the tumors were approximately 75 mm 3 in size.

The BR96-PEP-DOX conjugate was active and tolerated at doses of 1.25–20 mg/kg equivalent DOX/injection. Higher doses were not evaluated in this first experiment. As shown in Table 1 the BR96-PEP-DOX conjugate was significantly more active than optimized DOX at doses of ≧2.5 mg/kg equivalent DOX/injection. The activity of the BR96-PEP-DOX conjugate administered at 1.25 mg/kg was similar to that of unconjugated DOX administered at 8 mg/kg. These data suggest that the in vivo potency of the BR96-PEP-DOX conjugates is similar to that of BMS-182248. The peptide-DOX conjugates will be evaluated for antigen-specific antitumor activity as soon as a non-binding (IgG-PEP-DOX) conjugate can be prepared.

TABLE 1

Antitumor activity of BR96-DOX peptide conjugates against established L2987 human tumor xenografts

| Treatment DOX | Dose/Injection (mg/kg) | BR96 | Log Cell Kill | % Tumor Regressions Complete | Partial | Number of Mice |
|---|---|---|---|---|---|---|
| DOX | 8 | — | 2.4 | 10 | 0 | 10 |
|  | 6 | — | 1.5 | 0 | 0 | 10 |
|  |  |  |  |  |  | 10 |
| BR96-DOX | 20 | 1250 | >7 | 100 | 0 | 9 |
|  | 10 | 625 | >7 | 89 | 11 | 10 |
|  | 5 | 312 | >7 | 100 | 0 | 10 |
|  | 2.5 | 156 | >7 | 90 | 10 | 10 |
|  | 1.25 | 78 | 2.4 | 10 | 10 | 10 |
|  | 0.63 | 39 | 0.3 | 0 | 0 | 10 |
|  | 0.31 | 20 | 0.2 | 0 | 0 | 10 |

As a result of the above tests it can be seen that the compounds of the present invention are highly effective antitumor agents. They kill tumor cells in vitro via a specific targeting mechanism, in which the attached MAb BR96 is the targeting moiety, as shown by the fact that cells which express high levels of the antigen recognized by the MAb are efficiently killed; cells with less antigen are less efficiently killed; and cells without the antigen are not killed. Since all three cell types are sensitive to DOX, these results must arise from release of DOX after differential binding to the cells, not from differential toxicity of DOX to the various cell lines. The mechanism of the present invention is supported by the finding that Cathepsin B, a lysosomal protease, releases free DOX rapidly from both the peptide linker and the complete immunoconjugate. Since adventitious proteases in human blood do not release DOX from either the peptide linker or the complete immunoconjugate, it can be inferred that the immunoconjugate will reach tumor cells in human intact, without releasing free DOX enroute. Finally, in vivo experiments in tumor-bearing mice show that the immunoconjugate of the present invention produces remissions of antigen-positive tumors, with greater potency and less toxicity to the host than free DOX.

Thus, in an embodiment of the present invention, there is provided a method for the treatment of a neoplastic disease which comprises administering to a warm-blooded animal in need thereof, a therapeutically effective or biological function modifying amount of a conjugate of Formula (I). As can be appreciated, the particular conjugate used will depend on the disease state to be treated or the biological system to be modified. In particular, one skilled in the art will be able to select a particular ligand and drug to prepare a conjugate of Formula (I) which has specificity for the treatment of the disease or is able to modify the biological function desired.

A particularly preferred conjugate for this purpose is an immunoconjugate in which the drug moiety is doxorubicin and the ligand portion is selected from the group consisting of BR96, chimeric BR96, and the antigen-recognizing fragments thereof. The most preferred ligand for this embodiment is chimeric BR96, and the antigen-recognizing fragments thereof.

In a further embodiment, there is provided a process for preparing a compound of Formula (I), as previously defined.

The conjugates of the invention are administered to the patient in the form of a pharmaceutical formulation which comprises a conjugate of Formula (I) and a pharmaceutically acceptable carrier, excipient or diluent therefor. As used, "pharmaceutically acceptable" refers to those agents which are useful in the treatment or diagnosis of a warm-blooded animal including, for example, a human, equine, porcine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See, e.g. Remington's Pharmaceutical Sciences, 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The formulations may contain preservatives such as phenethyl alcohol, methyl and propyl parabens, thimerosal, and the like. If desired, the formulation can include 0.05 to about 0.20 percent by weight of an antioxidant such as sodium metabisulfite or sodium bisulfite.

For intravenous administration, the formulation preferably will be prepared so that the amount administered to the patient will be from about 1 to about 250 g of the desired conjugate. Preferably, the amount administered will be in the range of about 4 g to about 25 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

All publications cited in this specification are indicative of the level of skill of those in the art to which this application pertains. Each publication is individually incorporated herein by reference in the location where it is cited.

One skilled in the art will appreciate that although specific reagents and reaction conditions are outlined in the following Preparations and Examples, modifications can be made which are meant to be encompassed by the spirit and scope of the invention. The following Preparations and Examples, therefore, are provided to further illustrate the invention.

EXAMPLE 1

Preparation of Allyl-p-Nitrophenyl Carbonate (1)

Allyl alcohol (0.5 ml, 7.35 mmoles) in $CH_2Cl_2$ (3 ml) at room temperature was treated with p-nitrophenyl chloroformate (1.482 g, 1 equiv.). To this was added pyridine (0.6 ml, 1 equiv.) in $CH_2Cl_2$ (2 ml), dropwise over 10 minutes. After about 5 hours at room temperature the mixture was washed with 15% citric acid, water and brine, dried, and evaporated to give a thick, pale yellow oil. This was chromatographed on silica, eluting with 10–50% EtOAc/hexane, to give the product as an off-white, crystalline solid (1.542 g, 94%). $^1$H-NMR (CDCl$_3$): δ 4.78 (2H, d, CH$_2$—O), 5.40 (2H, q, vinyl CH$_2$), 5.99 (1H, m, vinyl CH), 7.37 and 8.26 (4H, 2xd, Ph); MS (DCI): 224 (MH)$^+$;

Anal. calc. for $C_{10}H_9NO_5$: C-53.82, H-4.06, N-6.28; Found: C-53.73, H-4.03, N-6.23.

EXAMPLE 2

Preparation of N$^α$-Boc-N$^ε$-Alloc-Lys (2)

A solution of Boc-Lys (8.4414 g, 34.27 mmoles) and NaHCO$_3$ (2.88 g, 1 equiv.) in water (50 ml) was added to allyl-p-nitrophenyl carbonate (1) (7.649 g, 1 equiv.) in DME (50 ml) at room temperature The mixture was stirred overnight at room temperature Water (80 ml) was then added and the mixture was extracted with ether (3×50 ml). The aqueous layer was acidified to pH 2 with 10% citric acid and then extracted with EtOAc (3×80 ml). The combined organic components were washed with water and brine, dried, and evaporated to give a white solid. This was treated with ether (100 ml) and the resulting mixture was sonicated for about 15 minutes to dissolve p-nitrophenol and then the solid (10.303 g, 91%) was collected by filtration and washed repeatedly with ether. $^1$H-NMR (CDCl$_3$/CD$_3$OD): δ 1.41 (9H, s, t-Bu), 1.49 and 1.70 (6H, m, Lys CH$_2$), 3.13 (2H, m, Lys N—CH$_2$), 4.25 (1H, m, CH), 4.52 (2H, d, allyl O—CH$_2$), 5.24 (2H, q, vinyl CH$_2$), 5.87 (1H, m, vinyl CH); MS (DCI): 331 (MH$^+$), 275 (MH$^+$—C$_4$H$_8$).

EXAMPLE 3

Preparation of N$^ε$-Alloc-Lys-TFA (3)

N$^α$-Boc-N$^ε$-alloc-Lys 2 (9.94 g, 30 mmoles) in $CH_2Cl_2$ (50 ml) was treated with TFA (19 ml) at room temperature The mixture was sonicated briefly and then stirred for about 1 hour. The solvents were evaporated at about 40° C. and the resulting yellow gum was triturated with ether (75 ml), giving a white solid (8.58 g, 83%. $^1$H-NMR (D$_2$O): δ 1.46 and 1.87 (4H and 2H resp., m, Lys CH$_2$), 3.11 (2H, m, N—CH$_2$), 3.80 (1H, t, Lys CH), 4.51 (2H, br s, allyl O—CH$_2$), 5.22 (2H, q, vinyl CH$_2$), 5.90 (1H, m, vinyl CH); MS (DCI): 231 (MH)$^+$;

Anal. calc. for $C_{12}H_{19}N_2O_6F_3$: C-41.86, H-5.56, N-8.14; Found: C-42.30, H-5.52, N-8.29.

EXAMPLE 4

Preparation of Z-Phe-NHS (4)

Z-Phe (11.03 g, 36.85 mmoles), and NHS (4.45 g, 1.1 equiv.) in THF (50 ml) at about 0° C. were treated with DCC (7.98 g, 1.05 equiv.). After a few minutes a heavy white precipitate appeared. The mixture was allowed to warm to room temperature and was stirred for about 16 hours. The solid DCU by-product was filtered off and the filtrate was evaporated. The resulting thick, colorless oil was dissolved in $CH_2Cl_2$ (80 ml). The mixture was allowed to stand for an hour and was then filtered to remove more DCU. The filtrate was evaporated and the resulting colorless glass was dried in vacuo for about 3 hours, giving a foamy solid (14.023 g, 96%) that was used without further purification. $^1$H-NMR (CDCl$_3$/CD$_3$OD): δ2.88 (4H, s, NHS CH$_2$), 3.27 (2H, m, Phe CH$_2$), 4.70 (1H, m, Phe CH), 5.13 (2H, s, Z CH$_2$), 7.27 (10H, m, Ph).

EXAMPLE 5

Preparation of Z-Phe-N$^ε$-Alloc-Lys (5)

Z-Phe-NHS (4) (2.783 g, 7.021 mmoles) in DME (30 ml) at room temperature was treated with a solution of N$^ε$-alloc-Lys-TFA (2.54 g, 1.05 equiv.) and NaHCO$_3$ (1.24 g, 2.1 equiv.) in water (30 ml). The mixture was stirred vigorously at room temperature for 2 days. A small amount of DCU was removed by filtration and the filtrate was diluted with water (50 ml) and then acidified to pH 3 with 15% citric acid. The resulting mixture was extracted with EtOAc (3×80 ml) and the combined organic layers were washed with water and brine, dried, and evaporated to give a glassy solid. This was treated with ether (150 ml), sonicated, and heated in a water bath (50° C.). Upon cooling, the white solid product (2.79 g, 78%) was collected by filtration and washed with ether. $^1$H-NMR (CDCl$_3$/CD$_3$OD): δ 1.25, 1.43, 1.74 and 1.81 (6H, m, Lys CH$_2$), 3.00 (2H, m, Phe CH$_2$), 3.08 (2H, m, N—CH$_2$), 4.43 (2H, m, CO—CH), 4.48 (2H, d, allylic O—CH$_2$), 5.02 (2H, m, Z CH$_2$), 5.20 (2H, q, vinyl CH$_2$), 5.84 (1H, m, vinyl CH), 7.22 (10H, m, Ph); MS (FAB): 512 (MH)$^+$, 534 (M+Na)$^+$, 556 (M+K)$^+$;

Anal. calc. for C$_{27}$H$_{33}$N$_3$O$_7$: C-63.39, H-6.50, N-8.21; Found: C-62.98, H-6.48, N-8.21.

EXAMPLE 6

Preparation of Z-Phe-N$^ε$-Alloc-Lys-PAB-OH (6)

Z-Phe-N$^ε$-alloc-Lys (5) (524.7 mg, 1.026 mmoles) and p-aminobenzyl alcohol (133 mg, 1.05 equiv.) in THF (10 ml) at room temperature were treated with EEDQ (266.3 mg, 1.05 equiv.). The mixture was stirred at room temperature for about 16 hours. The mixture was evaporated to dryness at about 30° C. and the residue triturated with ether (15 ml). The resulting white solid product (591.6 mg, 94%) was collected by filtration and washed with ether. $^1$H-NMR (CDCl$_3$/CD$_3$OD): δ 1.25, 1.42, 1.59 and 1.77 (6H, m, Lys CH$_2$), 2.97 (2H, m, Phe CH$_2$), 3.06 (2H, m, N—CH$_2$), 4.37 (2H, m, Phe and Lys CH), 4.46 (2H, d, allyl O—CH$_2$), 4.55 (2H, s, Ph—C$\underline{H}$—OH), 4.98 (2H, m, Z CH$_2$), 5.18 (2H, q, vinyl CH$_2$), 5.81 (1H, m, vinyl CH) 7.08 and 7.43 (4H, 2×d, PAB Ph), 7.11 and 7.23 (10H, m, Z and Phe Ph); MS (FAB): 617 (MH)$^+$, 639 (M+Na)$^+$, 655 (M+K)$^+$;

Anal. Calc. for C$_{34}$H$_{40}$N$_4$O$_7$: C-66.22, H-6.54, N-9.08, Found: C-65.72, H-6.43, N-8.92.

EXAMPLE 7

Preparation of Z-Phe-N$^ε$-Alloc-Lys-PABC-PNP (7)

Z-Phe-N$^ε$-alloc-Lys-PAB-OH (6) (269.6 mg, 437.2 μmoles) in dry THF (8 ml) at room temperature was treated with p-nitrophenyl chloroformate (106 mg, 1.2 equiv.) and pyridine (42.5 μl, 1.2 equiv.). After about 6 hours TLC (silica; 25:1 CH$_2$Cl$_2$/CH$_3$OH) indicated completion. EtOAc (25 ml) and 10% citric acid (25 ml) were added. The organic layer was washed with water and brine, dried, and evaporated to give a yellow solid which was chromatographed on silica, eluting with 30:1 CH$_2$Cl$_2$/CH$_3$OH, to give the product as an off-white solid (297.4 mg, 87%). $^1$H-NMR (CDCl$_3$/CD$_3$OD): δ 1.24, 1.42, 1.59 and 1.78 (6H, m, Lys CH$_2$), 2.97 (2H, m, N—CH$_2$), 3.04 (2H, m, Phe CH$_2$), 4.38 (2H, m, Phe and Lys CH), 4.46 (2H, d, allyl O—CH$_2$), 5.01 (2H, s, Z CH$_2$), 5.17 (2H, q, vinyl CH$_2$), 5.21 (2H, s, PAB CH$_2$—O), 5.37 and 5.80 (each 1H, m, Phe and Lys NH), 5.83 (1H, m, vinyl CH), 7.11 and 7.56 (4H, 2×d, PAB Ph), 7.13 and 7.25 (10H, m, Phe and Z Ph), 7.35 and 8.10 (each 2H, d, PNP Ph), 9.23 (1H, br s, PAB NH); MS (FAB): 782 (MH$^+$), 804 (M+Na)$^+$, 820 (M+K)$^+$;

Anal. calc. for C$_{41}$H$_{43}$N$_5$O$_{11}$: C-62.99, H-5.54, N-8.96; Found: C-62.75, H-5.49, N-8.86.

EXAMPLE 8

Preparation of Z-Phe-N$^ε$-Alloc-Lys-PABC-DOX (8)

Z-Phe-N$^ε$-alloc-Lys-PABC-PNP (7) (337.2 mg, 431.3 μmoles) and DOX-HCl (275.2 mg, 1.1 equiv.) in NMP (8 ml) at room temperature were treated with triethylamine (66 μl, 1.1 equiv.). The mixture was allowed to stand in the dark for about 2 days. The mixture was then diluted with 10% i-Pr—OH/EtOAc (100 ml) and washed with water (3×100 ml) and brine, dried, and evaporated to give an orange solid. This was chromatographed on silica, eluting with 1) 25:1 and 2) 15:1 CH$_2$Cl$_2$/CH$_3$OH, to give the product as an orange solid (496.3 mg, 97%). $^1$H-NMR (CDCl$_3$/CD$_3$OD): δ 1.18 (3H, d, sugar CH$_3$), 1.22, 1.38, 1.56 and 1.77 (6H, m, Lys CH$_2$), 1.74 (2H, m, D-ring—CH$_2$), 2.23 (2H, m, D-ring CH$_2$), 2.95 (2H, m, sugar CH$_2$)), 3.02 (2H, m, N—CH$_2$), 3.53 (1H, s, sugar HO—C$\underline{H}$), 3.80 (1H, m, sugar HN—CH), 3.99 (3H, s, OCH$_3$), 4.06 (1H, m, sugar CH$_3$—C$\underline{H}$), 4.39 (2H, m, Phe and Lys CH), 4.43 (2H, d, allyl O—CH$_2$), 4.70 (2H, s, PAB CH$_2$—O), 4.89 (2H, m, Z CH$_2$), 4.92 (1H, m, anomeric CH), 4.96 (2H, d, CO—C$\underline{H}_2$—OH), 5.15 (2H, q, vinyl CH$_2$), 5.11, 5.39 (each 1H, s, OH), 5.41 (1H, br, DOX Ph—CH), 5.60 and 5.92 (each 1H, m, amide NH), 5.79 (1H, m, vinyl CH), 7.08 and 7.23 (10H, m, Phe and Z Ph), 7.13 and 7.40 (4H, 2×d, PAB Ph), 7.50, 7.68 and 7.90 (each 1H, m, DOX Ph), 9.15 (1H, br s, PAB NH); MS (FAB): 1209 (M+Na)$^+$, 1224 (M+K)$^+$; HRMS (FAB): Accurate mass calc. for C$_{62}$H$_{67}$N$_5$O$_{19}$: 1186.4509; found: 1186.4463.

EXAMPLE 9

Preparation of Z-Phe-Lys-PABC-DOX-HCl (9)

Z-Phe-N$^ε$-alloc-Lys-PABC-DOX (8) (34.9 mg, 29.4 μmoles) and (PPh$_3$)$_2$PdCl$_2$ (0.6 mg, 3%) in dry THF (1 ml) under argon at room temperature were treated with acetic acid (3.5 μl, 2 equiv.) and then with Bu$_3$SnH (10 μl, 1.2 equiv.). The reaction was stirred at room temperature for about 1.5 hours and then treated with 1M HCl in ether (60 μl, 2 equiv.). The mixture was stored in the freezer for about 1 hour and then the crude orange solid was collected by filtration and washed repeatedly with ether. The solid was washed through the glass frit with 5:1 CH$_2$Cl$_2$/CH$_3$OH and then the filtrate was evaporated. The residue was sonicated in methanol (5 ml) to dissolve as much as possible and then filtered to remove an insoluble red by-product. The filtrate was evaporated to give an orange-red solid (25.1 mg, 75%). $^1$H-NMR (CDCl$_3$/CD$_3$OD): δ 1.18 (2H, d, sugar CH$_3$), 1.34, 1.65 and 1.73 (6H, m, Lys CH$_2$), 2.14 (2H, m, sugar CH$_2$), 2.81 (2H, m, C$\underline{H}_2$—NH$_{3+}$), 3.76 (1H, m, sugar HO—C$\underline{H}$), 3.98 (3H, s, OCH$_3$), 4.05 (1H, m, HN—C$\underline{H}$), 4.38 and 4.45 (each 1H, m, Phe and Lys CH), 4.67 (2H, s, CO—C$\underline{H}_2$—OH), 4.85 (1H, m, anomeric CH), 7.04 and 7.20 (10H, m, Z and Phe Ph), 7.14 and 7.43 (4H, m, PAB Ph), 7.30, 7.69 and 7.92 (each 1H, m, DOX Ph); HPLC (C-18, 15 cm column, 8:2 MeOH/50 mM Et$_3$N—HCO$_2$H buffer (pH 2.8), 1 ml/min., 495 nm): single peak, retention time 7.1–7.2 min.; MS (FAB): 1102 (MH$^+$), 1124 (M+Na)$^+$; HRMS (FAB): Accurate mass calc. for C$_{58}$H$_{64}$N$_5$O$_{17}$: 1102.4297, found: 1102.4260.

EXAMPLE 10

Preparation of Z-Val-NHS (10)

Z-Val (699.4 mg, 2.78 mmoles) and NHS (352.4 mg, 1.1 equiv.) in THF (20 ml) at about 0° C. were treated with DCC (632 mg, 1.1 equiv.). The reaction was worked up as described above for Z-Phe-NHS (4) to give the product as a glassy solid which was carried on to the next step without purification. $^1$H-NMR δ 1.03 (6H, 2×d, Val CH$_3$), 2.31 (1H, m, Val CH$_3$—C$\underline{H}$), 2.82 (4H, s, NHS CH$_2$), 4.65 (1H, AB Q, Val CO—CH), 5.12 (2H, s, Z CH$_2$), 5.30 (1H, d, NH), 7.34 (5H, m, Ph).

EXAMPLE 11

Preparation of Z-Val-N$^ε$-Alloc-Lys (11)

Z-Val—NHS (10) (about 2.78 mmoles) in DME (30 ml) was added to a solution of N$^ε$-alloc-Lys-TFA (3) (958.3 mg, 1 equiv.) and NaHCO$_3$ (468 mg, 2 equiv.) in water (20 ml). The reaction was worked up as described above for Z-Phe-N$^\epsilon$-alloc-Lys (5) to give the product as a white solid (1.2855g, quant.). $^1$H-NMR (CDCl$_3$/CD$_3$OD): δ0.89 (6H, 2×d, Val CH$_3$), 1.30, 1.42, 1.62 and 1.81 (6H, m, Lys CH$_2$), 2.03 (1H, m, Val CH$_3$—CH), 3.07 (2H, m, Lys N—CH$_2$), 3.92 (1H, AB q, Lys CH), 4.42 (1H, m, Val CO—CH), 4.49 (2H, d, allyl O—CH$_2$), 5.06 (2H, s, Z CH$_2$), 5.19 (2H, q, vinyl CH$_2$), 5.82 (1H, m, vinyl CH), 7.28 (5H, m, Ph); MS (FAB): 949 (MH$^+$), 971 (M+Na)$^+$, 987 (M+K)$^+$;

Anal. Calc. for C$_{23}$H$_{33}$N$_3$O$_7$: C-59.60, H-7.18, N-9.07; Found: C-59.94, H-7.31, N-8.90.

EXAMPLE 12

Preparation of Z-Val-N$^\epsilon$-Alloc-Lys-PAB-OH (12)

Z-Val-Ne-alloc-Lys (11) (587.9 mg, 1.27 mmoles) and p-aminobenzyl alcohol (172 mg, 1.1 equiv.) in THF (20 ml) at room temperature were treated with EEDQ (345 mg, 1.1 equiv.). The mixture was stirred at room temperature for 16 hrs. Workup as described above for Z-Phe-N$^\epsilon$-alloc-Lys-PAB-OH (6) gave the product as a white solid (591.0 mg, 82%). $^1$H-NMR (CDCl$_3$/CD$_3$OD): δ 0.86 (6H, m, Val CH$_3$), 1.24–1.67 (6H, m, Lys CH$_2$), 2.03 (m, 1H, Val CH$_3$—CH), 3.08 (2H, m, Lys N—CH$_2$), 4.00 (1H, m, Lys CH), 4.47 (3H, m, Val CO—CH and allyl O—CH$_2$), 4.57 (2H, s, PAB—CH$_2$—OH), 5.05 (2H, s, Z CH$_2$), 5.19 (2H, q vinyl CH$_2$), 5.81 (1H, m, vinyl CH), 7.26 and 7.43 (4H, m, PAB Ph), 7.30 (5H, s, Z Ph); MS (FAB): 569 (MH)$^+$, 591 (M+Na)$^+$, 607 (M+K)$^+$;

Anal. Calc. for C$_{30}$H$_{40}$N$_4$O$_7$-½ H$_2$O: C-62.38, H-7.15, N-9.70; Found: C-62.40, H-7.22, N-9.79.

EXAMPLE 13

Preparation of Z-Val-N$^\epsilon$-Alloc-Lys-PABC-PNP (13)

Z-Val-Ne-alloc-Lys-PAB-OH (12) (297.4 mg, 523 μmoles) and p-nitrophenyl chloroformate (264 mg, 2.5 equiv.) in CH2Cl2 (15 ml) at room temperature were treated with pyridine (106 μl, 2.5 equiv.). The mixture was stirred at room temperature for about 16 hours. Workup as described above for Z-Phe-Ne-alloc-Lys-PABC-PNP (7) gave the product as a white solid (271.0 mg, 71%). $^1$H-NMR (CDCl$_3$/CD$_3$OD): δ0.91 (6H, m, Val CH$_3$), 1.33–1.87 (6H, Lys CH$_2$), 2.02 (1H, m, Val CH$_3$—CH), 3.08 (2H, m, Lys N—CH$_2$), 3.95 (1H, m, Lys CH), 4.41 (1H, m, Val CO—CH), 4.48 (2H, d, allyl O—CH$_2$), 5.06 (2H, s, Z CH$_2$), 5.17 (2H, q, vinyl CH$_2$), 5.20 (2H, s, PAB CH$_2$), 5.82 (1H, m, vinyl CH), 7.23 and 7.58 (4H, m, PAB Ph), 7.30 (5H, m, Z Ph), 7.38 and 8.31 (4H, m, PNP Ph); MS (FAB): 734 (MH$^+$), 756 (M+Na)$^+$, 772 (M+K)$^+$; Accurate mass calc. for C$_{37}$H$_{44}$N$_5$O$_{11}$: 734.3037; found: 734.3036.

EXAMPLE 14

Preparation of Z-Val-N$^\epsilon$-Alloc-Lys-PABC-DOX (14)

Z-Val-N$^\epsilon$-alloc-Lys-PABC-PNP (13) (260.0 mg, 354 μmoles) and DOX-HCl (216 mg, 1.05 equiv.) in NMP (12 ml) at room temperature were treated with triethylamine (52 μl). The mixture was allowed to stand in the dark for 2 days. Workup as described above for Z-Phe-N$^\epsilon$-alloc-Lys-PABC-DOX (8) gave the product as an orange solid (278.0 mg, 69%). $^1$H-NMR (CDCl$_3$/CD$_3$OD): δ 0.83 (6H, m, Val CH$_3$), 1.18 (3H, d, sugar CH$_3$), 1.29, 1.41, 1.63 and 1.79 (6H, m, Lys CH$_2$), 1.72 (2H, m, D-ring CH$_2$), 1.98 (1H, m, Val CH$_3$—CH), 2.14 (2H, D-ring CH$_2$), 3.03 (2H, q, sugar CH$_2$), 3.02 (2H, m, Lys N—CH$_2$), 3.52 (1H, m, sugar HO—CH), 3.76 (1H, m, sugar N—CH), 3.94 (1H, m, Lys CH), 3.99 (3H, s, O—CH$_3$), 4.39 (1H, m, Val CO—CH), 4.42 (2H, d, allyl O—CH$_2$), 4.69 (2H, s, PAB CH$_2$), 4.88 (2H, m, Z CH$_2$), 5.01 (2H, d, CO—CH$_2$—OH), 5.14 (2H, q, vinyl CH$_2$), 5.18 (1H, m, anomeric CH), 5.41 (1H, br, DOX Ph—CH), 5.80 (1H, m, vinyl CH), 7.13 and 7.40 (4H, PAB Ph), 7.26 (5H, s, Z Ph), 7.32, 7.70 and 7.93 (each 1H, m, DOX Ph), 9.25 (1H, br, PAB NH); MS (FAB) 1160 (M+Na)$^+$, 1176 (M+K)$^+$; Accurate mass calc. for C$_{58}$H$_{67}$N$_5$O$_{19}$: 1160.4328; found: 1160.4358.

EXAMPLE 15

Preparation of Z-Val-Lys-PABC-DOX-HCl (15)

Z-Val-N$^\epsilon$-alloc-Lys-PABC-DOX (14) (84.3 mg, 74.06 μmoles) in THF (2 ml) under argon at room temperature was treated with Pd(PPh$_3$)$_4$ (220 μl of a solution of Pd$_2$dba$_3$ (4.7 mg, 5.13 μmoles) and PPh$_3$ (13.5 mg, 10 equiv.) in THF (1 ml) under argon), acetic acid (11 μl, 2.5 equiv.) and tributyltin hydride (30 μl, 1.5 equiv.). The mixture was stirred at room temperature in the dark for about 1 hour during which time an orange solid began to form. The mixture was diluted with ether (2 ml) followed by 1M HCl in ether (1 ml) and then more ether (25 ml). The resulting suspension was sonicated briefly and then filtered. The orange solid was washed repeatedly with ether and then dissolved in 5:1 CH$_2$Cl$_2$/CH$_3$OH. To this was added celite (about 2 g) and the solvents were evaporated. The resulting solid was dry-loaded atop a celite column (from a slurry in 100:1 CH$_2$Cl$_2$/CH$_3$OH). The column was eluted with 1) 100:1 and 2) 10:1 CH$_2$Cl$_2$/CH$_3$OH, to give the product as an orange solid (58.5 mg, 72.4%). $^1$H-NMR (selected peaks)(CDCl$_3$/CD$_3$OD): 6 (loss of allyl peaks) 0.83 (6H, m, Val CH$_3$), 1.20 (3H, d, sugar CH$_3$), 2.02 (1H, m, Val CH$_3$—CH), 4.01 (3H, s, O—CH$_3$), 7.10–7.57 (9H, m, Ph), 7.32, 7.72 and 7.91 (each 1H, m, DOX Ph); HPLC (C-18, 15 cm column, 8:2 MeOH/50 mM Et$_3$N—HCO$_2$H buffer (pH 2.8), 1 ml/min., 495 nm): single peak, retention time 6.1–6.4 min.; MS (FAB)1054 (MH)$^+$; Accurate mass calc. for C$_{54}$H$_{64}$N$_5$O$_{17}$: 1054.4297; found: 1054.4283.

EXAMPLE 16

Preparation of Alloc-D-Phe (16)

D-Phe (2.0203 g, 12.29 mmoles) and NaHCO$_3$ (1.08 g, 1.05 equiv.) in water (30 ml) were treated with diallyl dicarbonate (2.13 ml, 1.05 equiv.) in DME (30 ml). The mixture was stirred at room temperature for about 16 hours and then poured into 15% citric acid. The resulting suspension was extracted with EtOAc (2×100 ml). The combined organic layers were washed with water (3×100 ml) and brine, dried and evaporated to give a colorless foam which was pure enough to carry on to the next step (3.002 g, 98%). $^1$H-NMR (CDCl$_3$/CD$_3$OD): δ3.13 (2H, AB q, Phe CH$_2$), 4.52 (2H, d, CH$_2$—O), 4.64 (1H, q, Phe CH), 5.20 (2H, q, vinyl CH$_2$), 5.85 (1H, m, vinyl CH), 7.21 (5H, m, Ph); MS (DCI): 250 (MH)$^+$, 192 (M—C3H50)$^+$;

Anal. calc. for C$_{13}$H$_{15}$NO$_4$—H$_2$O: C-58.42, H-6.40, N-5.24; Found: C-58.81, H-5.87, N-5.36.

EXAMPLE 17

Preparation of Alloc-D-Phe-NHS (17)

Alloc-D-Phe (16) (3.002 g, 12.04 mmoles) and NHS (1.525 g, 1.1 equiv.) in CH$_2$Cl$_2$ at about 0° C. were treated with DCC (2.733 g, 1.1 equiv.). The ice bath was allowed to warm to room temperature and the mixture was stirred at room temperature for about 16 hours. Workup as described above for Z-Phe-NHS (4) gave the product as a colorless foam which was used without further purification (4.045 g, 97%).

EXAMPLE 18

Preparation of Alloc-D-Phe-Phe (18)

Alloc-D-Phe-NHS (17) (1.7654 g, 5.10 mmoles) in DME (30 ml) at room temperature was treated with a solution of Phe (1.263 g, 1.5 equiv.) and NaHCO3 (642.3 mg, 1.5 equiv.) in water (20 ml). The mixture was stirred at room temperature for about 16 hours. The mixture was then poured into 15% citric acid (100 ml) and the resulting suspension was extracted with EtOAc (2×100 ml). The combined organic layers were washed with water (3×) and brine, and then dried and evaporated to give a colorless glass. To this was added ether (30 ml) and the mixture was sonicated at room temperature for about 15 minutes and then stored in the freezer for about 1 hour. The solid product was collected by filtration and washed with ether (1.6973 g, 84%). $^1$H-NMR (CDCl$_3$/CD$_3$OD): δ2.83–3.16 (4H, m, Ph—CH$_2$), 4.45 (2H, d, CH$_2$—O), 4.63 and 4.89 (each 1H, m, N—CH), 5.21 (2H, q, vinyl CH$_2$), 5.81 (1H, m, vinyl CH), 6.93–7.34 (1OH, m, Ph); MS (DCI): 397 (MH)$^+$;

Anal. calc. for C$_{22}$H$_{24}$N$_2$O$_5$: C-66.65, H-6.10, N-7.07; Found: C-66.42, H-6.19, N-7.09.

EXAMPLE 19

Preparation of Alloc-D-Phe-Phe-NHS (19)

Alloc-D-Phe-Phe (18) (1.0151 g, 2.60 mmoles) and NHS (324.2 mg, 1.1 equiv.) in CH$_2$Cl$_2$ (25 ml) at 0° C. were treated with DCC (555 mg, 1.05 equiv.). The ice bath was allowed to warm to room temperature and the mixture was stirred for about 18 hours. The solid DCU was removed by filtration and the solvent was evaporated. The residue was dissolved in EtOAc and the solution was washed with water (2×) and brine, dried and evaporated to give a white solid which was used without further purification (1.2897 g, 100%).

EXAMPLE 20

Preparation of Alloc-D-Phe-Phe-N$^\epsilon$-Alloc-Lys (20)

Alloc-D-Phe-Phe-NHS (19) (1.2897 g, 2.61 mmoles) in DME (40 ml) was added a solution of N$^\epsilon$-alloc-Lys-TFA (945 mg, 1.05 equiv.) and NaHCO$_3$ (461 mg, 2.1 equiv.) in water (20 ml). The mixture was stirred vigorously at room temperature for about 16 hours. Workup as described above for Alloc-D-Phe-Phe (18) gave a crude white solid. This was suspended in ether and alternately sonicated and heated at about 40° C. for several minutes. The mixture was then stored at about 4° C. for about 2 hours and filtered to remove the white, solid product, which was washed with cold ether (1.2046 g, 76%). $^1$H-NMR (CDCl$_3$/CD$_3$OD): δ 1.21–1.94 (6H, 4×m, Lys CH$_2$), 2.79 and 2.91 (each 2H, m, Phe CH$_2$), 3.08 (2H, m, N—CH$_2$), 4.29 (1H, m, Lys CH), 4.38 and 4.59 (each 1H, m, Phe CH), 4.45 and 4.53 (each 2H, d, allyl O—CH$_2$), 5.20 (4H, m, vinyl CH$_2$), 5.85 (2H, m, vinyl CH), 7.06–7.27 (1OH, m, Ph); MS (FAB): 609 (MH)$^+$, 631 (M+Na)$^+$, 647 (M+K)$^+$;

Anal. calc. for C$_{32}$H$_{40}$N$_4$O$_8$: C-63.14, H-6.62, N-9.20; Found: C-63.05, H-6.78, N-9.25.

EXAMPLE 21

Preparation of Alloc-D-Phe-Phe-N$^\epsilon$-Alloc-Lys-PAB-OH (21)

Alloc-D-Phe-Phe-N$^\epsilon$-alloc-Lys (20) (616.8 mg, 1.013 mmoles) and p-aminobenzyl alcohol (137.3 mg, 1.1 equiv.) in THF (12 ml) at room temperature were treated with EEDQ (276 mg, 1.1 equiv.). The mixture was stirred at room temperature for about 18 hours. Workup as described above for Z-Phe-Ne-alloc-Lys-PAB-OH (6) gave the product as a white solid (685.7 mg, 95%). $^1$H-NMR (CDCl$_3$/CD$_3$OD): δ1.20–1.98 (6H, 4×m, Lys CH$_2$), 2.95 (4H, m, Phe CH$_2$), 3.08 (2H, m, N—CH$_2$), 4.25 (2H, AB q, allyl O—CH$_2$), 4.49 (2H, d, allyl O—CH$_2$), 4.57 (2H, s, PAB CH$_2$), 5.15 (4H, m, vinyl CH$_2$), 5.62 and 5.87 (each 1H, m, vinyl CH), 6.96 and 7.54 (each 2H, m, PAB Ph), 7.06–7.31 (1OH, m, Ph); MS (FAB): 714 (MH)$^+$, 736 (M$^+$Na)$^+$, 752 (M+K)$^+$; Accurate mass calc. for C$_{39}$H$_{48}$N$_5$O$_8$: 714.3503; found: 714.3494;

Anal. calc. for C$_{39}$H$_{47}$N$_5$O$_8$·H$_2$O: C-64.01, H-6.75, N-9.57; Found: C-64.39, H-6.63, N-9.54.

EXAMPLE 22

Preparation of Alloc-D-Phe-Phe-N$^\epsilon$-Alloc-Lys-PABC-PNP (22)

Alloc-D-Phe-Phe-N$^\epsilon$-alloc-Lys-PAB-OH (21) (330.8 mg, 463.4 μmoles) and p-nitrophenyl chloroformate (140.1 mg, 1.5 equiv.) in CH$_2$Cl$_2$ (20 ml) at room temperature were treated with dry pyridine (56.2 μl, 1.5 equiv.). Workup as described above for Z-Phe-Ne-alloc-Lys-PABC-PNP (7) gave the product as a white solid (379.0 mg, 93%). $^1$H-NMR (CDCl$_3$/CD$_3$OD): δ1.20–2.00 (6H, 4×m, Lys CH$_2$), 2.97 (4H, m, Phe CH$_2$), 3.10 (2H, m, N—CH$_2$), 4.21 (2H, AB q, allyl O—CH$_2$), 4.30, 4.52 and 4.67 (each 1H, m, N—CH), 4.49 (2H, d, allyl O—CH$_2$), 5.10 (2H, m, vinyl CH$_2$), 5.22 (2H, s, PAB CH$_2$), 5.58 and 5.87 (each 1H, m, vinyl CH), 6.93 and 7.66 (each 2H, m, PAB Ph), 7.04–7.25 (1OH, m, Ph), 7.32 and 8.04 (each 2H, m, PNP Ph); MS (FAB): 879 (MH)$^+$, 901 (M+Na)$^+$, 917 (M+K)$^+$; Accurate mass calc. for C$_{46}$H$_{51}$N$_6$O$_{12}$: 879.3565; found: 879.3533.

EXAMPLE 23

Preparation of Alloc-D-Phe-Phe-N$^\epsilon$-alloc-Lys-PABC-DOX (23)

Alloc-D-Phe-Phe-Ne-alloc-Lys-PABC-PNP (22) (379.0 mg, 431.2 mmoles) and DOX-HCl (262.6 mg, 1.05 equiv.) in NMP (10 ml) at room temperature were treated with triethylamine (63 ml, 1.05 equiv.). The mixture was stored in the dark at room temperature for 2 days and then diluted with 10% i-propyl alcohol/EtOAc (150 ml). The resulting solution was washed with water (4×) and brine, filtered to remove a small amount of orange solid by-product, and then evaporated to give an orange solid. This was chromatographed on silica, eluting with 1) 30:1 and 2) 15:1 CH$_2$Cl$_2$/CH$_3$OH, to give the product as an orange solid (418.8 mg, 76%). $^1$H-NMR (CDCl$_3$/CD$_3$OD): δ 1.21 (3H, d, sugar CH$_3$), 1.28–1.96 (6H, 4×m, Lys CH$_2$), 1.76 (2H, m, D-ring CH$_2$) , 2.18 (D-ring CH$_2$), 2.87 (2H, m, sugar CH$_2$), 3.05 (2H, m, N—CH$_2$), 3.55 (1H, s, sugar HO—CH), 3.78 (1H, m, sugar N—CH), 3.99 (3H, s, CH$_3$—O), 4.10 (1H, m, sugar CH$_3$—CH), 4.26 (2H, m, allyl O—CH$_2$), 4.40 (3H, m, CO—CH), 4.45 (2H, d, allyl O—CH$_2$), 4.70 (2H, s, CO—CH$_2$—OH), 4.89 (2H, m, PAB CH$_2$), 5.16 (4H, m, vinyl CH$_2$), 5.20 (1H, s, anomeric CH), 5.41 (1H, s, DOX Ph—CH), 5.52 and 5.80 (each 1H, m, vinyl CH), 6.85–7.52

113

(14H, m, Ph), 7.32, 7.72 and 7.97 (each 1H, m, DOX Ph); MS (FAB⁻): 1282.4 (MH)⁻; Accurate mass calc. for C$_{67}$H$_{74}$N$_6$O$_{20}$Na: 1305.4856; found: 1305.4877.

EXAMPLE 24

Preparation of D-Phe-Phe-Lys-PABC-DOX-2HCl (24)

Alloc-D-Phe-Phe-N$^\epsilon$-alloc-Lys-PABC-DOX (23) (164.0 mg, 127.8 μmoles)) in degassed 2:1 CH$_2$Cl$_2$/CH$_3$OH (4 ml) at room temperature under argon was treated with acetic acid (37 μl, 5 equiv.) and then 460 μl of a solution of Pd(PPh$_3$)$_4$ (Pd$_2$dba$_3$ (6.4 mg) and PPh$_3$ (18 mg) in degassed 2:1 CH$_2$Cl$_2$/CH$_3$OH (1 ml)). To this was added triethylsilane (61 μl, 3 equiv.) and the mixture was stirred in the dark for about 16 hours at room temperature The solvents were removed on the rotovap (40° C.) and the orange, glassy residue was treated with ether (2 ml) and 1M HCl in ether (1 ml). This was sonicated for several minutes. The resulting orange solid was collected by filtration and then taken up as far as possible in water. The insoluble material was filtered off and the filtrate evaporated to dryness. The residue was chromatographed on celite, eluting with 1) 50:1, 2) 12:1, and 3) 5:1 CH$_2$Cl$_2$/CH$_3$OH. The first solvent system eluted any uncharged material, the second eluted singly-charged (mono-deprotected) material, and the product eluted in the third (100.4 mg, 66%). ¹H-NMR (CDCl$_3$/CD$_3$OD): δ 1.12 (3H, d, sugar CH$_3$), 1.00–1.90 (8H, m, Lys CH$_2$ and D-ring CH$_2$), 2.07 (2H, m, D-ring CH$_2$), 2.55–3.16 (8H, m, ⁺H$_3$N—CH$_2$ sugar CH$_2$, Phe CH$_2$), 3.45 (1H, s, sugar HO—CH), 3.70 (1H, m, sugar N—CH), 3.90 (3H, s, O—CH$_3$), 4.21, 4.33 and 4.43 (each 1H, m, CO—CH), 4.61 (2H, s, CO—CH$_2$—OH), 4.80 (2H, m, PAB CH$_2$), 5.12 (1H, brs, anomeric CH), 5.33 (1H, brs, DOX Ph—CH), 6.80–7.90 (17H, m, Ph); HPLC: (C-18, 15 cm column, 8:2 MeOH/50 mM Et$_3$N—HCO$_2$H buffer (pH 2.8), 1 ml/min., 495 nm): single peak, retention time 5.5–5.8 min.; MS (FAB⁻): 1114.6 (MH)⁻.

EXAMPLE 25

Preparation of Z-Val-Cit (26)

To a solution of Z-Val-NHS (10) (2.98 g, 8.566 mmoles) in DME (25 ml) at room temperature was added a solution of citrulline (2.25 g, 1.5 equiv.) and NaHCO$_3$ (1.08 g, 1.5 equiv.) in water (25 ml). The mixture was stirred vigorously for 2 days. Water (20 ml) containing 2 ml sat. NaHCO$_3$ was added and the mixture was washed with EtOAc and acidified to pH 3 with 10% HCl. The resulting suspension was extracted with 10% Bu—OH/EtOAc (3×). The combined organic layers were dried and evaporated to give a white solid (3.39 g, 97%). ¹H-NMR (CDCl$_3$/CD$_3$OD): δ 0.73 (6H, q, Val CH$_3$), 1.31, 1.46 and 1.63 (4H, m, Cit CH$_2$), 1.87 (1H, m, Val CH$_3$—CH), 2.88 (2H, m, N—CH$_2$), 3.72 (1H, AB q, Cit CH), 4.17 (1H, m, Val COCH), 4.86 (2H, s, Z CH$_2$), 7.10 (5H, m, Z Ph); MS (FAB): 409 (MH)⁺, 431 (M+Na)⁺, 447 (M+K)⁺; Accurate mass calc. for C$_{19}$H29N$_4$O$_6$: 409.2087; found: 409.2086.

EXAMPLE 26

Preparation of Z-Val-Cit-PAB-OH (27)

Z-Val-Cit (26) (1,0397 g, 2.545 mmoles) and p-aminobenzyl alcohol (470.2 mg, 1.5 equiv.) in THF (10 ml) at room temperature were treated with EEDQ (944.2 mg, 1.5 equiv.). The mixture was stirred at room temperature

114 for about 16 hours and then diluted with 10% i-Pr—OH/EtOAc (100 ml). This was washed with 10% citric acid, water and brine, dried and evaporated. The pale-yellow solid residue was sonicated in ether for 15 min. and the crude solid product was collected by filtration (954.2 mg, 73%). ¹H-NMR (CDCl$_3$/CD$_3$OD): δ 0.79 (6H, q, Val CH$_3$), 1.37, 1.53 and 1.72 (4H, m, Cit CH$_2$), 1.92 (1H, m, Val CH$_3$—CH), 3.00 (2H, m, N—CH$_2$), 3.85 (1H, m, Cit CH), 4.41 (1H, m, Val COCH), 4.45 (2H, s, PAB CH2), 4.95 (2H, m, Z CH$_2$), 7.08–7.40 (9H, m, Ph); MS (FAB): 514 (MH)⁺, 536 (M+Na)⁺, 552 (M+K)⁺;

Anal. calc. for C$_{26}$H$_{35}$N$_5$O$_6$-H$_2$O: C-58.74, H-7.01, N-13.17; Found: C-59.01, H-6.62, N-13.17.

EXAMPLE 27

Preparation of Z-Val-Cit-PABC-PNP (28)

Z-Val-Cit-PAB-OH (27) (383.0 mg, 745.7 μmoles) and p-nitrophenyl chloroformate (225.5 mg, 1.5 equiv.) in THF (10 ml) and CH$_2$Cl$_2$ (5 ml) were treated at room temperature with pyridine (91 μl, 1.5 equiv.). Workup as described above for Z-Phe-Ne-alloc-Lys-PABC-PNP (7) gave a crude, pale-yellow solid which was chromatographed on silica, eluting with 1) 30:1 and 2) 12:1 CH$_2$Cl$_2$/CH$_3$OH, to give the product as an off-white solid (440.3 mg, 87%). ¹H-NMR (CDCl$_3$/CD$_3$OD): δ 0.88 (6H, m, Val CH$_3$), 1.42, 1.61 and 1.80 (4H, m, Cit CH$_2$), 2.02 (1H, m, Val CH$_3$—CH), 3.08 (2H, m, N—CH$_2$), 3.99 (1H, m, Cit CH), 4.51 (1H, m, Val COCH), 5.00 (2H, m, Z CH$_2$), 7.20–7.57 (9H, m, Ph), 7.30 and 8.20 (each 2H, m, PNP Ph); MS (FAB): 679 (MH)⁺, 701 (M+Na)⁺, 717 (M+K)⁺; Accurate mass calc. for C$_{33}$H$_{39}$N$_6$O$_{10}$: 679.2728; found: 679.2720.

EXAMPLE 28

Preparation of Z-Val-Cit-PABC-DOX (29)

Z-Val-Cit-PABC-PNP (28) (126.9 mg, 187 μmoles) and DOX-HCl (119.3 mg, 1.1 equiv.) in NMP (5 ml) at room temperature were treated with triethylamine (29 μl, 1.1 equiv.). The mixture was stirred in the dark at room temperature for 2 days. Workup as described above for Alloc-D-Phe-Phe-N$^\epsilon$-alloc-Lys-PABC-DOX (23) gave a crude orange solid. This was chromatographed on silica, eluting with 1) 12:1, 2) 8:1, and 3) 5:1 CH$_2$Cl$_2$/CH$_3$OH, to give the product as a red-orange solid (158.0 mg, 78%). ¹H-NMR (CDCl$_3$/CD$_3$OD): δ 0.74 (6H, m, Val CH$_3$), 1.07 (3H, d, sugar CH$_3$), 1.28–1.88 (4H, m, Cit CH$_2$), 1.64 and 2.08 (each 2H, m, D-ring CH$_2$), 1.88 (1H, m, Val CH$_3$—CH), 2.87 (2H, m, sugar CH$_2$), 3.42 (1H, brs, sugar HO—CH), 3.95 (1H, m, sugar N—CH), 4.11 (3H, s, O—CH$_3$), 4.38 (2H, m, CO—CH), 4.58 (2H, s, CO—CH$_2$—OH), 4.78 (2H, s, PAB CH$_2$), 4.90 (2H, s, Z CH$_2$), 5.04 (1H, brs, anomeric CH), 5.30 (1H, brs, DOX Ph—CH), 7.00–7.86 (12H, m, Ph), 9.31 (1H, brs, PAB NH); HPLC: (C-18, 15 cm column, 8:2 MeOH/50 mM Et$_3$N-HCO$_2$H buffer (pH 2.8), 1 ml/min., 495 nm): single peak, retention time 3.65–3.75 min.; MS, (FAB⁻): 1082.8 (M⁻); Accurate mass calc. for C$_{54}$H$_{63}$N$_6$O$_{18}$: 1083.4199; found: 1083.4161.

EXAMPLE 29

Preparation of Z-Phe-N$^\epsilon$-alloc-Lys-PABC-2'-Taxol (30)

Taxol (15.8 mg, 18.5 μmoles) and Z-Phe-N$^\epsilon$-alloc-Lys-PABC-PNP (7) (14.5 mg, 1 equiv.) in CH$_2$Cl$_2$ (2 ml) at room temperature were treated with DMAP (2.5 mg, 1.1 equiv.).

After 2 days at room temperature TLC (silica; 25:1 $CH_2Cl_2$/$CH_3OH$) indicated completion. EtOAc (25 ml) was added and the mixture was washed with 10% citric acid, water, brine, dried and evaporated to give a pale-yellow glass. This was chromatographed on silica, eluting with 30:1 $CH_2Cl_2$/$CH_3OH$, to give the product as a colorless glass (26.1 mg, 94%). $^1$H-NMR (selected peaks): δ 1.13, 1.23, 1.68 and 1.81 (each 3H, s, Taxol $CH_3$), 2.20 and 2.46 (each 3H, s, Ac $CH_3$), 3.13 (2H, m, CON—$CH_2$), 4.25 (2H, AB q, C-20 $CH_2$), 4.47 (1H, m, C-7 CH), 4.52 (2H, d, alloc O—$CH_2$), 4.97 (2H, m, Z $CH_2$), 5.05 (2H, s, PAB $CH_2$), 5.12 (2H, m, vinyl $CH_2$), 5.45 (1H, d, C-2' CH), 5.88 (1H, m, vinyl CH), 7.10–8.17 (29H, m, Ph), 8.59 (1H, s, PABC NH); MS (Ion spray): 1496.8 $(MH)^+$, 1519.6 $(M+Na)^+$; Accurate mass calc. for $C_{82}H_{89}N_5O_{22}$: 1496.6078; found: 1496.6082.

EXAMPLE 30

Preparation of Z-Phe-Lys-PABC-2'-Taxol-HCl (31)

Z-Phe-$N^ε$-alloc-Lys-PABC-2'-Taxol (30) (18.1 mg, 12.09 μmoles) in dry THF (1 ml) at room temperature under argon was treated with AcOH (1.7 μl, 2.5 equiv.), $Pd(PPh_3)_4$ (45 μl of a solution of $Pd_2dba_3$ (6.2 mg, 6.77 μmoles) and $PPh_3$ (17.8 mg, 10 equiv.) in dry THF (1 ml)), and $Bu_3SnH$ (5 μl, 1.5 equiv.). After about 30 minutes more $Bu_3SnH$ (5 μl) was added. After about 30 more minutes ether (5 ml) and then 1M HCl in ether (1 ml) were added. The resulting suspension was sonicated for several minutes and the white solid was collected by filtration and washed repeatedly with ether (14.37 mg, 82%). $^1$H-NMR ($CDCl_3$/$CD_3OD$)(selected peaks): δ (loss of allyl peaks) 2.98 (2H, m, $^+H_3N$—$CH_2$), 4.27 (2H, AB q, C-20 $CH_2$), 4.39 (1H, m, C-7 CH), 5.02 (2H, m, Z $CH_2$), 5.09 (2H, m, PAB $CH_2$), 7.06–8.20 (29H, m, Ph); HPLC: (C-18, 15 cm column, 8:2 MeOH/50 mM $Et_3N$-$HCO_2H$ buffer (pH 2.8), 1 ml/min., 230 nm): single peak, retention time 4.8 min., (6:4 MeCN/50 mM Et3N-HCO2H buffer (pH 2.8)): single peak, retention time: 9.6 min.; MS (Ion spray): 1413.2 $(MH)^+$; Accurate mass calc. for $C_{78}H_{86}N_5O_{20}$: 1412.5866; found: 1412.5883.

EXAMPLE 31

Preparation of Boc-Phe-NHS (32)

Boc-Phe (5.4257 g, 20.45 mmoles) and NHS (2.354 g, 1 equiv.) in THF (55 ml) at about 0° C. were treated with DCC (4.22 g, 1 equiv.). The ice bath was allowed to melt and the mixture was stirred at room temperature for about 16 hours. The solid DCU was filtered off and the filtrate was evaporated to give a white solid which was used without further purification (7.2624 g, 98%). $^1$H-NMR: δ 1.39 (9H, s, t-Bu), 2.85 (4H, br s, NHS $CH_2$), 3.22 (2H, m, Phe $CH_2$), 4.94 (1H, m, CH), 7.29 (5H, m, Ph).

EXAMPLE 32

Preparation of Boc-Phe-$N^ε$-Fmoc-Lys (33)

$N^ε$-Fmoc-Lys (3.0651 g, 8.32 mmoles) and $NaHCO_3$ (769 mg, 1.1 equiv.) in water (50 ml) and DME (20 ml) were treated, at room temperature, with a solution of Boc-Phe-NHS (32) (3.015 g, 1 equiv.) in DME (40 ml). The mixture was stirred vigorously at room temperature for about 18 hours and then diluted with EtOAc (100 ml) and 10% citric acid. The aqueous layer was re-extracted with EtOAc (50 ml). The combined organic layers were washed with water (2×) and brine, dried and evaporated to give a pale-yellow solid. This was dissolved in ether and a small amount of undissolved solid was removed by filtration. The filtrate was evaporated to dryness and the pale-yellow foamy residue was dried in vacuo (5.0881 g, 99%). $^1$H-NMR ($CDCl_3$/$CD_3OD$): δ 1.30, 1.48, 1.67 and 1.85 (6H, m, Lys $CH_2$), 1.35 (9H, s, t-Bu), 3.01 (2H, m, Phe $CH_2$), 3.12 (2H, m, N—$CH_2$), 4.18 (1H, t, Fmoc CH), 4.36 (2H, d, Fmoc $CH_2$), 4.41 and 4.50 (each 1H, m, CO—CH), 7.12–7.77 (13H, m, Ph); MS (FAB): 616 $(MH)^+$, 638 $(M+Na)^+$, 654 $(M+K)^+$;

Anal. calc. for $C_{35}H_{41}N_3O_7$: C-68.27, H-6.71, N-6.82; Found: C-68.13, H-6.84, N-6.44.

EXAMPLE 33

Preparation of Boc-Phe-$N^ε$-Fmoc-Lys-PAB-OH (34)

Boc-Phe-$N^ε$-Fmoc-Lys (33) (4.8207 g, 7.83 mmoles) and p-aminobenzyl alcohol (1.061 g, 1.1 equiv.) in THF (50 ml) at room temperature were treated with EEDQ (2.13 g, 1.1 equiv.). The mixture was stirred at room temperature for about 16 hours. Workup as described above for Z-Phe-$N^ε$-alloc-Lys-PAB-OH (6) gave the product as an off-white solid (4.4579 g, 79%). $^1$H-NMR ($CDCl_3$/$CD_3OD$): δ 1.28, 1.48, 1.63 and 1.84 (6H, m, Lys $CH_2$), 1.33 (9H, s, t-Bu), 3.00 (2H, m, Phe $CH_2$), 3.11 (2H, m, N—$CH_2$), 4.15 (1H, t, Fmoc CH), 4.31 (2H, d, Fmoc $CH_2$), 4.38 (2H, m, CO—CH), 4.57 (2H, s, PAB $CH_2$), 7.08–7.75 (17H, m, Ph); MS (FAB): 721 $(MH)^+$, 743 $(M+Na)^+$, 759 $(M+K)^+$;

Anal. calc. for $C_{42}H_{48}N_4O_7$-½ $H_2O$: C-69.12, H-6.77, N-7.68; Found: C-68.96, H-6.87, N-7.64.

EXAMPLE 34

Preparation of 2'-Fmoc-Taxol (35)

Taxol (134.6 mg, 157.6 μmoles) and Fmoc-NHS (58.5 mg, 1.1 equiv.) in $CH_2Cl_2$ (3 ml) at room temperature were treated with DMAP (19.3 mg, 1 equiv.). After about 5 days at room temperature TLC (silica; 25:1 $CH_2Cl_2$/$CH_3OH$) indicated completion. EtOAc (50 ml) was added and the mixture was washed with 10% citric acid, water, brine, dried and evaporated. The residue was chromatographed on silica, eluting with 35:1 $CH_2Cl_2$/$CH_3OH$, to give the product as a colorless glass (165.6 mg, 98%). $^1$H-NMR: δ 1.13, 1.24 and 1.67 (each 3H, s, C-16, C-17 and C-19 $CH_3$), 1.92 (3H, s, C-18 $CH_3$), 1.87 and 2.52 (2H, m, C-6 $CH_2$), 2.22 and 2.44 (each 3H, s, Ac $CH_3$), 2.41 (2H, m, C-14 $CH_2$), 2.50 (1H, d, C-7 OH), 3.82 (1H, d, C-3 CH), 4.28–4.51 (6H, m, C-20 $CH_2$, C-7 CH, Fmoc CH and $CH_2$), 4.98 (1H, d, C-5 CH), 5.47 (1H, d, C-2' CH), 5.69 (1H, d, C-2 CH), 6.03 (1H, m, C-3' CH), 6.30 (1H, s, C-10 CH), 6.32 (1H, t, C-13 CH), 6.99 (1H, d, NH), 7.22–8.20 (23H, m, Ph); MS (FAB): 1076 $(MH)^+$, 1098 $(M+Na)^+$, 1114 $(M+K)^+$; Accurate mass calc. for $C_{26}H_{62}NO_{16}$: 1076.4069; found: 1076.4031.

EXAMPLE 35

Preparation of Boc-Phe-$N^ε$-Fmoc-Lys-PABC-7-Taxol-2'-Fmoc (36)

2'-Fmoc-taxol (35) (112.1 mg, 90.3 μmoles) in dry $CH_2Cl_2$ (1 ml) under argon at about 0° C. was treated with pyridine (8 μl, 1.1 equiv.) and diphosgene (6.5 μl, 0.6 equiv.). After about 40 minutes Boc-Phe-$N^ε$-Fmoc-Lys-PAB-OH (65.1 mg, 1 equiv.) and DMAP (0.5 mg) in $CH_2Cl_2$ (1 ml)/pyridine (0.2 ml) were added. The mixture was stirred at about 0° C. for about 30 minutes and then at room temperature for about 4 hours. EtOAc (30 ml) was then added and the solution was washed with 10% citric acid (2×), water and brine, then dried and evaporated to give a white solid. This was chromatographed on silica, eluting with 30:1 $CH_2Cl_2/CH_3OH$, to give the product as a colorless glass (81.7 mg, 50%, two of the three product-containing fractions were contaminated with 2'-Fmoc-taxol)). $^1$H-NMR ($CDCl_3/CD_3OD$): δ 1.19, 1.22 and 1.80 (each 3H, s, C-16, C-17 and C-19 $CH_3$), 1.10–1.90 (6H, m, Lys $CH_2$), 1.38 (9H, s, t-Bu), 1.82 and 2.54 (each 1H, m, C-6 $CH_2$), 2.05 (3H, s, C-18 $CH_3$), 2.23 and 2.42 (each 1H, m, C-14 $CH_2$), 2.18 and 2.47 (each 3H, s, Ac $CH_3$), 3.09 (2H, m, Phe $CH_2$), 3.19 (2H, m, Lys N—$CH_2$), 3.98 (1H, d, C-3 CH), 4.15–4.52 (7H, m, Phe and Lys CO—CH, Fmoc $CH_2$ and CH, C-20 $CH_2$), 4.98 (1H, m, C-5 CH), 5.14 (2H, m, PAB $CH_2$), 5.48 (1H, d, C-2' CH), 5.55 (1H, m, C-7 CH), 5.69 (1H, m, C-2 CH), 6.02 (1H, m, C-3' CH), 6.29 (1H, m, C-13 CH), 6.41 (1H, s, C-10 CH), 6.96–8.18 (40H, m, Ph); MS (FAB): 1823 (MH)$^+$, 1846 (M+Na)$^+$, 1862 (M+K)$^+$.

EXAMPLE 36

Preparation of Boc-Phe-Lys-PABC-7-Taxol-HCl (37)

Boc-Phe-N$^\epsilon$-Fmoc-Lys-PABC-7-Taxol-2'-Fmoc (36) (74.6 mg, 40.95 μmoles) in THF (2 ml) at room temperature was treated with 2% DBU in THF (2 ml). After about 6 minutes at room temperature ether (25 ml) was added and the resulting white solid was collected by filtration and washed with ether. The solid was suspended in ether (5 ml) and treated with 1M HCl in ether (2 ml). After about 2 minutes the solid was filtered off and washed thoroughly with ether. The solid was chromatographed on LH-20 lipophilic sephadex, eluting with 1:1 $CH_2Cl_2/CH_3OH$, to give the product as a colorless glasss (35.6 mg, 90%). $^1$H-NMR ($CDCl_3/CD_3OD$): δ 1.13, 1.19 and 1.78 (each 3H, s, C-16, C-17 and C-19 $CH_3$), 1.37 (9H, s, t-Bu), 1.10–1.90 (6H, m, Lys $CH_2$), 1.86 and 2.54 (each 1H, m, C-6 $CH_2$), 2.05 (3H, s, C-18 $CH_3$), 2.16 and 2.38 (each 3H, s, Ac $CH_3$), 2.97 (2H, m, $^+H_3N$—$CH_2$), 3.12 (2H, m, Phe $CH_2$), 3.90 (1H, d, C-3 CH), 4.24 (2H, m, C-20 $CH_2$), 4.45 and 4.68 (each 1H, m, Phe and Lys CO—CH), 4.83 (1H, brs, C-2' CH), 4.91 (1H, d, C-5 CH), 5.12 (2H, m, PAB $CH_2$), 5.48 (1H, m, C-7 CH), 5.67 (1H, d, C-2 CH), 5.78 (1H, d, c-3' CH), 6.12 (1H, m, C-13 CH), 6.33 (1H, s, C-10 CH), 7.08–8.12 (24H, m, Ph); HPLC: (C-18, 15 cm column, 8:2 MeOH/50 mM $Et_3N$—$HCO_2H$ buffer (pH 2.8), 1 ml/min., 230 nm): single peak, retention time: 7.1–7.3 min.; MS (Ion spray): 1379.2 (MH)$^+$; Accurate mass calac. for $C_{75}H_{88}N5O_{20}$: 1378.6023; found: 1378.6043.

EXAMPLE 37

Preparation of Boc-Phe-N$^\epsilon$-Fmoc-Lys-PABC-Cl (38)

Boc-Phe-N$^\epsilon$-Fmoc-Lys-PAB-OH (34) (211.2 mg, 293 μmoles) in pyridine (0.5 ml) and $CH_2Cl_2$ (2 ml) at –42° C. (dry ice-MeCN) under argon was treated with diphosgene (21.2 μl, 0.6 equiv.). The mixture was stirred at about –42° C. for about 20 minutes during which time solid pyridinium hydrochloride had precipitated out of solution. This solution was used immediately.

EXAMPLE 38

Preparation of Boc-Phe-N$^\epsilon$-Fmoc-Lys-PABC-MMC (39)

To the above solution of Boc-Phe-N$^\epsilon$-Fmoc-Lys-PABC-Cl (38) at about –42° C. was added MMC (118.0 mg, 1.2 equiv.) in NMP (1 ml). The cooling bath was allowed to warm to room temperature gradually and the mixture was stirred in the dark for about 12 hours at room temperature. The mixture was diluted with 10% i-Pr-OH/EtOAc (50 ml) and 10% citric acid (50 ml). The organic layer was washed with water (3×) and brine, dried and evaporated to give a purple-brown residue. This was chromatographed on a 1 mm silica prep. plate, eluting with 12:1 $CH_2Cl_2/CH_3OH$, to give the product as a light purple solid (108.0 mg, 34%). $^1$H-NMR ($CDCl_3/CD_3OD$): δ 1.21, 1.43, 1.61 and 1.81 (6H, m, Lys $CH_2$), 1.32 (9H, s, t-Bu), 2.10 (3H, s, MMC $CH_3$), 2.99 (2H, m, Phe $CH_2$), 3.11 (2H, m, Lys N—$CH_2$), 3.14 (3H, s, O—$CH_3$), 3.20–3.50 (3H, m, C-1 and C-2 CH, and C-3 CH), 3.62 (1H, ABq, C-9 CH), 4.18 (1H, t, Fmoc CH), 4.22 and 4.89 (each 1H, ABq, C-10 $CH_2$), 4.32 (2H, d, Fmoc $CH_2$), 4.41 (1H, d, C-3 CH), 4.45 (2H, m, Phe and Lys CO—CH), 5.01 (2H, m, PAB $CH_2$), 7.05–7.90 (17H, m, Ph); MS (FAB): 1082 (MH)$^+$, 1103 (M+Na)$^+$, 1119 (M+K)$^+$; Accurate mass calc. for $C_{58}H_{64}N_8O_{13}Na$: 1103.4491; found: 1103.4451.

EXAMPLE 39

Preparation of Boc-Phe-Lys-PABC-MMC-HCl (40)

Boc-Phe-N$^\epsilon$-Fmoc-Lys-PABC-MMC (39) (11.2 mg, 10.36 μmoles) in THF (1 ml) at room temperature was treated with 2% DBU in THF (1 ml). A fine purple solid slowly formed. After about 5 minutes the volume was reduced to about 1 ml on the rotovap (bath temp. 30° C.) and ether (10 ml) was added. The resulting solid was collected by filtration and washed with ether. The solid was suspended in ether (2 ml) and treated with 1M HCl in ether (3 ml). After about 2 minutes the solid was filtered off, washed thoroughly with ether, and then triturated with $CH_2Cl_2$ (2 ml). The resulting solid was collected by filtration and washed with $CH_2Cl_2$ (9.1 mg, 98%). $^1$H-NMR ($CDCl_3/CD_3OD$): δ 1.30 (9H, s, t-Bu), 1.20–1.90 (6H, m, Lys $CH_2$), 1.94 (3H, s, MMC $CH_3$), 2.83 (2H, m, $^+H_3N$—$CH_2$), 2.98 (2H, m, Phe $CH_2$), 3.13 (3H, s, O—$CH_3$), 3.20–3.70 (4H, m, C-1 and C-2 CH, C-3 CH and ABq, C-9 CH), 4.14 and 4.82 (each 1H, ABq, C-10 CH), 4.25–4.52 (3H, m, Phe and Lys CO—CH and C-3 CH), 4.97 (2H, m, PAB $CH_2$), 7.12 (5H, brs, Phe Ph), 7.23 and 7.50 (each 2H, m, PAB Ph); HPLC: (C-18, 15 cm column, 65:35 MeOH/50 mM $Et_3N$—$HCO_2H$ buffer (pH 2.8), 1 ml/min., 365 nm): single peak, retention time: 4.1–4.3 min.; MS (FAB): 859 (MH)$^+$, 881 (M+Na)$^+$, 897 (M+K)$^+$; Accurate mass calc. for $C_{43}H_{55}N_8O_{11}$: 859.3990; found: 859.3980.

EXAMPLE 40

Preparation of N$^\alpha$-Fmoc-N$^\epsilon$-Mtr-Lys (41)

N$^\alpha$-Fmoc-Lys (14.840 g, 40.28 mmoles) was suspended in dry $CH_2Cl_2$ (200 ml) at room temperature under argon. Trimethylsilyl chloride (10.9 ml, 2 equiv.) was added with vigorous stirring, and the mixture was heated at reflux for about one hour, and then cooled to about 0° C. DIEA (14.0 ml, 2 equiv.) was added, followed by p-anisyldiphenylmethyl chloride (13.061 g, 1.05 equiv.) in $CH_2Cl_2$ (50 ml). The ice bath was removed and the mixture was stirred for about 2 hours at room temperature. Methanol (8.2 ml, 5 equiv.) was added and stirring was continued for one hour and then the solvents were evaporated. The residue was partitioned between ethyl acetate and pH 5 buffer (biphthalate). The organic layer was washed with water and brine, dried and evaporated, giving a pale orange gum. This was flushed with $CH_2Cl_2$ and dried in vacuo to give a foam

EXAMPLE 41

Preparation of N$^\epsilon$-Mtr-Lys (42)

N$^\alpha$-Fmoc-N$^\epsilon$-Mtr-Lys (41) (10.006 g, 15.615 mmoles) in CH$_2$Cl$_2$ (50 ml) at room temperature was treated with diethylamine (40 ml). The mixture was stirred at room temperature for about 24 hours and then the solvents were evaporated and the residue flushed with CH$_2$Cl$_2$ (3×100 ml). The pale yellow residue was triturated with ether. The resulting suspension was sonicated for several minutes, and the solid was collected by filtration, washed with ether and dried in vacuo for several hours (6.191 g, 95%). $^1$H-NMR (CDCl$_3$/CD$_3$OD) δ 1.34, 1.57 and 1.72 (6H, m, Lys CH$_2$), 2.05 (2H, m, N—CH$_2$), 3.38 (1H, m, CO—CH), 3.68 (3H, s, OCH$_3$), 3.71 (2H, d, MeOPh o-CH), 7.03–7.40 (12H, m, Ph); MS (FAB) 419.2 (MH)$^+$, 441.4 (M+Na)$^+$, 457.4 (M+K)$^+$.

EXAMPLE 42

Preparation of Fmoc-Phe-NHS (43)

Fmoc-Phe (5.1043 g, 13.17 mmoles) and NHS (1.592 g, 1.05 equiv.) in CH$_2$Cl$_2$ (100 ml) at about 0° C. were treated with DCC (2.854 g, 1.05 equiv.). The ice bath was allowed to warm to room temperature and the mixture was stirred for about 14 hours. The DCU by-product was removed by filtration and the filtrate was evaporated. The resulting crude product, a colorless glass, was used without further purification.

EXAMPLE 43

Preparation of Fmoc-Phe-N$^\epsilon$-Mtr-Lys (44)

A suspension of N$^\epsilon$-Mtr-Lys (42) (4.686 g, 11.20 mmoles) and NaHCO$_3$ (941.0 mg, 1 equiv.) in water (100 ml) and DME (50 ml) was treated with a solution of Fmoc-Phe-NHS (43) (11.20 mmoles) in DME (50 ml). THF (25 ml) was then added to aid solubility. The mixture was stirred at room temperature for 2 days and then as much DME as possible was removed on the rotovap (bath at about 30° C.). The resulting gummy suspension was partitioned between ethyl acetate and pH 5 buffer. The organic phase was washed with water and brine, dried and evaporated to give a pale yellow foam. This was flushed with CH$_2$Cl$_2$ (100 ml). TLC showed the product to be fairly pure and it was carried on without further purification (8.559 g, 97%). $^1$H-NMR (CDCl$_3$/CD$_3$OD) δ 1.10–1.93 (6H, m, Lys CH$_2$), 2.31 (2H, t, N—CH$_2$), 3.00 (2H, m, Phe CH$_2$), 3.71 (3H, s, O—CH$_3$), 4.02–4.48 (5H, m, Fmoc CH$_2$ and CH, CO—CH), 6.79 (2H, d, MeOPh o-CH), 7.00–7.75 (25H, m, Ph); MS (FAB) 788.2 (MH)$^+$, 810.4 (M+Na)$^+$, 826 (M+K)$^+$;

Anal. calc. for C$_{50}$H$_{49}$N$_3$O$_6$·H$_2$O: C-74.51, H-6.38, N-5.21; Found: C-74.17, H-6.57, N-5.41.

EXAMPLE 44

Preparation of Fmoc-Phe-N$^\epsilon$-Mtr-Lys-PAB-OH (45)

Fmoc-Phe-N$^\epsilon$-Mtr-Lys (44) (7.728 g, 9.808 mmoles) and p-aminobenzyl alcohol (1.450 g, 1.2 equiv.) in CH$_2$Cl$_2$ (100 ml) at room temperature were treated with EEDQ (3.640 g, 1.5 equiv.). The mixture was stirred at room temperature for about 20 hours and then the solvent was evaporated (water bath at about 30° C.). The solid residue was triturated with ether (200 ml) and the resulting suspension sonicated for about 15 minutes and left to stand at room temperature for about 2 hours. The resulting solid was collected by filtration, washed well with ether, and dried in vacuo (7.6140 g, 87%). $^1$H-NMR (CDCl$_3$/CD$_3$OD) δ 0.98–1.91 (6H, m, Lys CH$_2$), 2.06 (2H, t, N—CH$_2$), 2.97 (2H, m, Phe CH$_2$), 3.71 (3H, s, O—CH$_3$), 4.12 (1H, t, Fmoc—CH), 4.20–4.41 (4H, m, Fmoc CH$_2$ and CO—CH), 4.59 (2H, s, PAB CH$_2$), 6.72 (2H, d, MeOPh o-CH), 7.00–7.73 (29H, m, Ph); MS (FAB) 891.4 (MH)$^+$, 916.7 (M+Na)$^+$, 931 (M+K)$^+$;

Anal. calc. for C$_{57}$H$_{56}$N$_4$O$_6$·H$_2$O: C-75.14, H-6.42, N-6.15; Found: C-75.25, H-6.02, N-6.49.

EXAMPLE 45

Preparation of Phe-N$^\epsilon$-Mtr-Lys-PAB-OH (46)

Fmoc-Phe-N$^\epsilon$-Mr-Lys-PAB-OH (45) (4.2857 g, 4.80 mmoles) in CH$_2$Cl$_2$ (35 ml) at room temperature was treated with diethylamine (50 ml). The mixture was sonicated briefly and stirred at room temperature for 4 hours after which time no starting material was observed by TLC. The solvents were evaporated and the residue was flushed with CH$_2$Cl$_2$ and chromatographed on silica, eluting with 1) 2% methanol/CH$_2$Cl$_2$, 2) 3% methanol/CH$_2$Cl$_2$, and 3) 4% methanol/CH$_2$Cl$_2$, to give the product as a colorless foam (2.230 g, 69%). $^1$H-NMR (CDCl$_3$) δ 1.26–2.00 (6H, m, Lys CH$_2$), 2.12 (2H, t, N—CH$_2$), 2.75 and 3.21 (each 1H, ABq, Phe CH$_2$), 3.68 (1H, ABq, Phe CO—CH), 3.76 (3H, s, O—CH$_3$), 4.42 (1H, q, Lys CO—CH), 4.66 (2H, brs, PAB CH$_2$), 6.79 (2H, d, MeOPh o-CH), 7.10–7.42 (21H, m, Ph), 7.81 (1H, d, amide NH), 8.71 (1H, s, PAB NH); MS (FAB) 693.4 (M+Na)$^+$, 709 (M+K)$^+$;

Anal. calc. for C$_{42}$H$_{46}$N$_4$O$_4$·½H$_2$O: C-74.20, H-6.97, N-8.24; Found: C-74.28, H-7.00, N-8.34.

EXAMPLE 46

Preparation of MC-Phe-N$^\epsilon$-Mtr-Lys-PAB-OH (47)

Phe-N$^\epsilon$-Mtr-Lys-PAB-OH (46) (448.1 mg, 0.668 mmoles) and DIEA (0.128 ml, 1.1 equiv.) in CH$_2$Cl$_2$ (5 ml) at room temperature were treated with MC-NHS (230.4 mg, 1.12 equiv.) in CH$_2$Cl$_2$ (2 ml). The mixture was stirred at room temperature for 3 days. Ethyl acetate (60 ml) was added and the mixture was washed with pH 5 buffer (2×), water and brine, dried and evaporated. The residue was triturated with ether (60 ml) and the resulting solid collected by filtration and washed with ether (563.8 mg, 98%). $^1$H-NMR (CDCl$_3$) δ 1.05–1.96 (12H, m, Lys and caproyl CH$_2$), 2.07 (2H, t, Lys N—CH$_2$), 2.18 (2H, t, CO—CH$_2$), 3.02 (2H, m, Phe CH$_2$), 3.39 (2H, t, M—CH$_2$), 3.71 (3H, s, O—CH$_3$), 4.64 (3H, s and m, PAB CH$_2$ and Lys CO—CH), 4.99 (1H, q, Phe CO—CH), 6.61 (2H, s, M CH), 6.71 (2H, d, MeOPh o-CH), 6.89 (1H, m, amide NH), 7.00–7.55 (21H, m, Ph), 8.97 (1H, brs, PAB NH); MS (FAB) 864 (MH)$^+$, 886 (M+Na)$^+$, 902.4 (M+K)$^+$.

EXAMPLE 47

Preparation of MC-Phe-N$^\epsilon$-Mtr-Lys-PABC-PNP (48)

MC-Phe-N$^\epsilon$-Mtr-Lys-PAB-OH (47) (679.3 mg, 0.786 mmoles) and bis-p-nitrophenyl carbonate (1.196 g, 5 equiv.)

under argon at room temperature were dissolved in $CH_2Cl_2$ (25 ml) and treated with DIEA (0.411 ml, 3 equiv.). After 3 days TLC indicated completion. The volume was reduced to about 5 ml on the rotovap and the residue was diluted with ethyl acetate (80 ml) and washed with pH 5 buffer, water and brine, dried and evaporated. The resulting solid was triturated with ether (80 ml), and the solid was collected by filtration, washed with ether, and chromatographed on silica, eluting with 1) 1:1 and 2) 8:1 ethyl acetate/hexane (the sample was loaded on the column in a minimum amount of 8:1 ethyl acetate/hexane), to give the product as a pale yellow glass (670.7 mg, 83%). $^1$H-NMR (CDCl$_3$) δ 1.10–1.95 (12H, m, Lys and caproyl CH$_2$), 2.04 (2H, t, Lys N—CH$_2$), 2.13 (2H, t, CO—CH$_2$), 3.04 (2H, m, Phe CH$_2$), 3.39 (2H, t, M—CH$_2$), 3.72 (3H, s, O—CH$_3$), 4.58 (1H, q, Lys CO—CH), 4.86 (1H, q, Phe CO—CH), 5.27 (2H, s, PAB CH$_2$), 6.58 (1H, d, amide NH), 6.61 (2H, s, M CH), 6.72 (2H, d, MeOPh o-CH), 7.03–7.62 (27H, m, Ph and NH), 8.22 (2H, d, PNP CH), 8.86 (1H, brs, PAB NH); MS (FAB) 1029 (MH)$^+$, 1051.5 (M+Na)$^+$, 1069.4 (M+K)$^+$.

EXAMPLE 48

Preparation of MC-Phe-N$^\epsilon$-Mtr-Lys-PABC-DOX (49)

MC-Phe-N$^\epsilon$-Mtr-Lys-PABC-PNP (48) (126.6 mg, 0.123 mmoles) and DOX.HCl (71.3 mg, 1 equiv.) in NMP (5 ml) at room temperature were treated with DIEA (21.4 μl, 1 equiv.). After 2 days standing in the dark at room temperature the mixture was diluted with ethyl acetate (60 ml) and washed with water (4×) and brine, dried and evaporated. The residue was chromatographed on silica, eluting with 1) 25:1 and 2) 20:1 $CH_2Cl_2$/methanol, to give the product as an orange glass (149.0 mg, 85%). $^1$H-NMR (CDCl$_3$) δ 1.10–1.95 (14H, m, Lys and caproyl CH$_2$, D-ring CH$_2$), 1.27 (3H, d, sugar CH$_3$), 2.10 (4H, m, Lys N—CH$_2$ and caproyl CO—CH$_2$), 2.23 (2H, m, D-ring CH$_2$), 3.03 (2H, m, Phe CH$_2$), 3.20 (2H, m, sugar CH$_2$), 3.41 (2H, t, M—CH$_2$), 3.67 (1H, brs, sugar HO—CH), 3.77 (3H, s, Mtr O—CH$_3$), 4.08 (3H, s, DOX O—CH$_3$), 4.13 (sugar N—CH), 4.40 (1H, m, Phe CO—CH), 4.56 (2H, m, Lys CO—CH and sugar CH$_3$—CH), 4.76 (2H, brs, CO—CH$_2$—OH), 4.99 (2H, m, PAB CH$_2$), 5.29 (1H, brs, anomer CH), 5.51 (1H, brs, DOX Ph—CH), 5.18, 6.02 and 6.38 (each 1H, m, NH), 6.62 (2H, s, M CH), 6.77 (2H, d, MeOPh o-CH), 7.00–7.60 (22H, m, Ph), 7.78 and 8.03 (each 1H, m, DOX Ph CH), 8.22 (1H, brs, PAB NH); MS (FAB) 1433.8 (MH)$^+$, 1456.0 (M+Na)$^+$, 1471.8 (M+K)$^+$.

EXAMPLE 49

Preparation of MC-Phe-Lys-PABC-DOX.Cl$_2$CHCO$_2$H (50)

A stirred solution of MC-Phe-N$^\epsilon$-Mtr-Lys-PABC-DOX (49) (1.1520 g, 0.804 mmoles) in $CH_2Cl_2$ (50 ml) and anisole (8.73 ml, 100 equiv.) was treated with dichloroacetic acid (0.663 ml, 10 equiv.). After about 1 hour ethyl acetate (80 ml) was added and the resulting suspension was stored in the freezer for about 1.5 hours. The solid was collected by filtration, washed with ethyl acetate, and dried in vacuo. The filtrate was concentrated to about 30 ml on the rotovap (bath at about 27° C.) and then ether (50 ml) was added. The resulting suspension was stored in the freezer for about 1 hour and then filtered. The orange solid was triturated repeatedly with CH2Cl2 and then dried in vacuo (1.0092 g, 97%). $^1$H-NMR (CDCl$_3$/CD$_3$OD) δ 1.10–1.90 (14H, m, Lys and caproyl CH$_2$, D-ring CH$_2$), 1.21 (3H, d, sugar CH$_3$), 2.10 (2H, t, caproyl CO—CH$_2$), 2.20 (2H, m, D-ring CH$_2$), 2.88 (2H, m, Lys N—CH$_2$), 3.02 (2H, m, Phe CH$_2$), 3.12 (2H, m, sugar CH$_2$), 3.38 (2H, t, M—CH$_2$), 3.52 (1H, brs, sugar HO—CH), 3.79 (1H, m, sugar HN—CH), 4.02 (3H, s, DOX O—CH$_3$), 4.10 (1H, m, sugar CH$_3$—CH), 4.43 and 4.54 (each 1H, m, Phe and Lys CO—CH), 4.72 (2H, s, DOX CO—CH$_2$—OH), 4.92 (2H, m, PAB CH$_2$), 5.24 (1H, br s, anomeric CH), 5.44 (1H, br s, DOX Ph—CH—O-sugar), 5.84 (1H, s, Cl$_2$CH), 6.67 (2H, s, M CH), 7.10 (5H, brs, Phe Ph), 7.21 and 7.48 (each 2H, d, PAB Ph), 7.38, 7.77 and 7.99 (each 1H, d, t, and d, resp., DOX Ph); HPLC: (C-18, 15 cm column, 8:2 methanol/50 mM triethylammonium formate buffer (pH 2.8), 1 ml/min., 495 nm): single peak, retention time: 4.4–4.5 min.; MS (FAB$^-$): 1159 (M–H)$^-$; Accurate mass calc. for $C_{60}H_{68}N_6O_{18}Na$: 1183.4488; found: 1183.4457.

EXAMPLE 50

Preparation of MC-Phe-N$^\epsilon$-Mtr-Lys-PABC-MMC (51)

A stirred mixture of MC-Phe-N$^\epsilon$-Mtr-Lys-PABC-PNP (48) (160.4 mg, 0.1559 mmoles), HOBt (211.0 mg, 10 equiv.) and MMC (57.3 mg, 1.1 equiv.) in NMP (5 ml) at room temperature was treated with DIEA (0.271 ml, 10 equiv.). After about 14 hours at room temperature ethyl acetate (100 ml) was added and the mixture was washed with pH 5 buffer, water and brine, dried and evaporated. The residue was chromatographed on silica, eluting with 1) 25:1 and 2) 20:1 $CH_2Cl_2$/methanol, to give the product as a purple glass (136.2 mg, 71%). $^1$H-NMR (CDCl$_3$) δ 1.08–1.90 (12H, m, CH$_2$), 1.73 (3H, s, MMC CH$_3$), 2.10 (4H, m, Lys N—CH$_2$ and CO—CH$_2$), 3.05 (2H, m, Phe CH$_2$), 3.18 (3H, s, MMC O—CH3), 3.23–3.50 (5H, m, C-1, C-2 and C-3 CH and M—CH$_2$), 3.63 (1H, ABq, C-9 CH), 3.74 (3H, s, Mtr O—CH$_3$), 4.28 and 4.90 (each 1H, t and ABq, C-10 CH$_2$), 4.41 (2H, d and m, C-3 CH and Phe CO—CH), 4.71 (1H, m, Lys CO—CH), 5.01 (2H, m, PAB CH$_2$), 5.09 (1H, brs, amide NH), 5.30 (4H, brs, NH$_2$), 6.31 and 6.88 (each 1H, d, amide NH), 6.63 (2H, s, M CH), 6.76 (2H, d, MeOPh o-CH), 7.06–7.57 (21H, m, Ph), 8.81 (1H, brs, PAB NH); MS (FAB) 1246.5 (M+Na)$^+$, 1262.3 (M+K)$^+$.

EXAMPLE 51

Preparation of MC-Phe-Lys-PABC-MMC.CLCH$_2$CO$_2$H (52)

A stirred solution of MC-Phe-N$^\epsilon$-Mtr-Lys-PABC-MMC (51) (68.1 mg, 55.6 μmoles) in $CH_2Cl_2$ (3 ml) and anisole (0.604 ml, 100 equiv.) was treated with chloroacetic acid (1M in $CH_2Cl_2$, 0.56 ml, 10 equiv.). A purple precipitate gradually formed. After 3 hours ether (5 ml) was added. The resulting solid was collected by filtration and washed with ether and $CH_2Cl_2$, and then dissolved in methanol. HPLC showed it to be >95% pure (44.7 mg, 74%). $^1$H-NMR (CDCl$_3$/CD$_3$OD) δ 1.11, 1.40, 1.63 and 1.77 (12H, m, CH$_2$), 2.09 (2H, t, CO—CH$_2$), 3.02 (2H, m, Phe CH$_2$), 3.13 (3H, s, MMC O—CH$_3$), 3.23–3.50 (5H, m, C-1, C-2 and C-3 CH and M—CH$_2$), 3.56 (1H, ABq, C-9 CH), 3.92 (2H, brs, ClCH$_2$), 4.13 and 4.82 (each 1H, t and ABq, C-10 CH$_2$), 4.30 (1H, d, C-3 CH), 4.41 (1H, m, Phe CO—CH), 4.65 (1H, m, Lys CO—CH), 4.99 (2H, q, PAB CH$_2$), 6.63 (2H, s, M CH), 7.10 (5H, brs, Phe Ph), 7.22 and 7.48 (each 2H, d, PAB Ph); MS (FAB) 952.3 (MH)$^+$, 974 (M+Na)$^+$, 990.3 (M+K)$^+$; HPLC: (C-18, 15 cm column, 65:35 methanol/50 mM triethylammonium formate buffer (pH 2.8), 1 ml/min., 360 nm): single peak, retention time: 2.84 min.

EXAMPLE 52

Preparation of 2'-Methoxytrityl-Taxol (53)

A stirred solution of taxol (0.51 g, 0.597 mmoles) and p-methoxytrityl chloride (4.63 g, 25 equiv.) in $CH_2Cl_2$ (14 ml) under nitrogen at room temperature was treated with pyridine (1.23 ml, 25 equiv.). After about 16 hours at room temperature the solvent was evaporated and the residue dissolved in ethyl acetate. The solution was washed with cold pH 5 buffer (2×100 ml), water and brine, dried and evaporated. The residue was chromatographed on silica, eluting with 3% methanol/$CH_2Cl_2$, to give the product as a white solid (482 mg, 72%). $^1$H NMR ($CDCl_3$) δ 1.11, 1.17 and 1.55 (each 3H, s, C-16, C-17 and C-19 $CH_3$), 1.67 (3H, s, C-18 $CH_3$), 1.90 and 2.54 (2H, m, C-6 $CH_2$), 2.26 and 2.51 (each 3H, s, Ac $CH_3$), 2.54 (2H, m, C-14 $CH_2$), 3.66 (1H, d, C-3 CH), 3.78 (3H, s, O—$CH_3$), 4.21 (2H, ABq, C-20 $CH_2$), 4.41 (1H, m, C-7 CH), 4.63 (1H, d, C-2' CH), 4.92 (1H, d, C-5 CH), 5.62 (1H, d, C-2 CH), 5.70 (2H, m, C-13 and C-3' CH), 6.22 (1H, s, C-10 CH), 6.74 (2H, d, MeOPh o-CH), 7.09–7.60 (23H, m, Ph), 7.80 and 8.09 (each 2H, d, Bz o-CH); MS (FAB) 1148 (M+Na)$^+$, 1164 (M+K)$^+$.

EXAMPLE 53

Preparation of MC-Phe-N$^\epsilon$-Mtr-Lys-PABC-7-Taxol-2'-Mtr (54)

2'-Methoxytrityl-taxol (53) (218.8 mg, 0.194 mmoles) in dry $CH_2Cl_2$ (3 ml) under argon at about 0° C. was treated with DIEA (34 μl, 1 equiv.), pyridine (15.7 μl, 1 equiv.) and then diphosgene (12 μl, 0.5 equiv.). The ice bath was removed and the mixture was stirred at room temperature for about 1 hour and then recooled to about 0° C. MC-Phe-N$^\epsilon$-Mtr-Lys-PAB-OH (47) (167.9 mg, 1 equiv.) was flushed with dry $CH_2Cl_2$ (6 ml), dried in vacuo and then dissolved in dry $CH_2Cl_2$ (2 ml) and DIEA (34 μl, 1 equiv.). This solution was added via syringe to the crude chloroformate at about 0° C. After about 10 minutes the ice bath was removed and the mixture was stirred at room temperature for about 18 hours. The mixture was diluted with ethyl acetate and washed with pH 5 buffer, water and brine, dried and evaporated. The residue was chromatographed on silica, eluting with 1) 2:1 $CH_2Cl_2$/ethyl acetate, 2) 1:1 ethyl acetate/$CH_2Cl_2$, 3) 4:1 ethyl acetate/$CH_2Cl_2$ and 4) ethyl acetate, to give the product as a colorless glass (237.9 mg, 61%), along with unreacted starting materials. $^1$H NMR ($CDCl_3$) δ 1.13, 1.16 and 1.57 (each 3H, s, C-16, C-17 and C-19 $CH_3$), 1.10–1.80 (12H, m, Lys and caproyl $CH_2$), 1.88 and 2.61 (each 1H, m, C-6 $CH_2$), 1.78 (3H, s, C-18 $CH_3$), 2.10 (4H, m, Lys N—$CH_2$ and caproyl CO—$CH_2$), 2.17 and 2.29 (each 3H, s, Ac $CH_3$), 3.06 (2H, m, Phe $CH_2$), 3.42 (2H, t, caproyl N—$CH_2$), 3.75 and 3.78 (each 3H, s, O—$CH_3$), 3.82 (1H, m, C-3 CH), 4.21 (2H, ABq, C-20 $CH_2$), 4.42 and 4.70 (each 1H, q, Phe and Lys CO—CH), 4.62 (1H, d, C-2' CH), 4.93 (1H, d, C-5 CH), 5.19 (2H, q, PAB $CH_2$), 5.59 (1H, m, C-7 CH), 5.62 (1H, d, C-2 CH), 5.72 (2H, m, C-3' CH and C-13 CH), 6.17 and 6.60 (each 1H, brd, amide NH), 6.32 (1H, s, C-10 CH), 6.64 (2H, s, M CH), 6.77 (4H, m, MeOPh o-CH), 7.05–7.60 (44H, m, Ph), 7.80 and 8.06 (each 2H, d, Bz o-CH), 8.37 (1H, brs, PAB NH).

EXAMPLE 54

Preparation of MC-Phe-Lys-PABC-7-Taxol.$ClCH_2CO_2H$ (55)

A stirred solution of MC-Phe-N$^\epsilon$-Mtr-Lys-PABC-7-Taxol-2'-Mtr 54 (194.8 mg, 0.097 mmoles) in $CH_2Cl_2$ (4.5 ml) and anisole (1.05 ml, 100 equiv.) was treated with chloroacetic acid (1M in $CH_2Cl_2$, 0.97 ml, 10 equiv.). After about 4 hours ether (25 ml) was added. The resulting solid was collected by filtration and washed with ether (142.0 mg, 94%). $^1$H NMR ($CDCl_3$) δ 1.13, 1.20 and 1.72 (each 3H, s, C-16, C-17 and C-19 $CH_3$), 1.10–1.90 (12H, m, Lys and caproyl $CH_2$), 2.13 and 2.33 (each 3H, s, Ac $CH_3$), 2.96 (2H, m, $^+H_3N$—$CH_2$), 3.05 (2H, m, Phe $CH_2$), 3.38 (2H, m, caproyl N—$CH_2$), 3.86 (1H, d, C-3 CH), 4.21 (2H, m, C-20 $CH_2$), 4.50 and 4.61 (each 1H, m, Phe and Lys CO—CH), 4.77 (1H, brs, C-2' CH), 4.91 (1H, d, C-5 CH), 5.10 (2H, m, PAB $CH_2$), 5.42 (1H, m, C-7 CH), 5.64 (1H, d, C-2 CH), 5.71 (1H, m, C-3' CH), 6.11 (1H, m, C-13 CH), 6.30 (1H, s, C-13 CH), 6.73 (2H, s, M CH), 7.00–8.20 (24H, m, Ph); HPLC (C-18, 15 cm column, 7:3 acetonitrile/50 mM triethylammonium formate buffer (pH 2.8), 1 ml/min., 250 nm): single peak, retention time 2.91 min.; MS (FAB) 1471.6 (MH$^+$), 1509.5 (M+Na)$^+$, 1511.8 (M+K)$^+$.

EXAMPLE 55

Preparation of Fmoc-Val-NHS (56)

Fmoc-Val (5.060 g, 14.91 mmoles) and NHS (1.72 g, 1 equiv.) in THF (50 ml) at about 0° C. were treated with DCC (3.080 g, 1 equiv.). The mixture was stirred at room temperature for about 16 hours and then the solid DCU by-product was filtered off and washed with THF. The solvent was removed on the rotovap and the resulting colorless, glassy solid was used without purification in the next step.

EXAMPLE 56

Preparation of Fmoc-Val-Cit (57)

Fmoc-Val-NHS (56) (14.91 mmoles) in DME (40 ml) was added to a solution of L-citrulline (2.743 g, 1.05 equiv.) and $NaHCO_3$ (1.315 g, 1.05 equiv.) in water (40 ml). THF (20 ml) was added to aid solubility, and the mixture was stirred at room temperature for about 16 hours. Aqueous citric acid (15%, 75 ml) was added and the mixture was extracted with 10% isopropanol/ethyl acetate (2×100 ml). The solid product began to precipitate but remained with the organic layer. The suspension was washed with water (2×150 ml) and the solvents were evaporated. The resulting white solid was dried in vacuo for about 5 hours and then treated with ether (80 ml). After sonication and trituration the white solid product was collected by filtration (5.8007 g, 78%). $^1$H-NMR (DMSO-$d_6$) δ 0.87 (6H, q, Val $CH_3$), 1.40, 1.59 and 1.69 (4H, m, Cit $CH_2$), 1.97 (1H, m, Val $CH_3$—CH), 2.94 (2H, q, Cit N—$CH_2$), 3.92 (1H, t, Fmoc CH), 4.10–4.35 (2H, m, Val and Cit CO—CH), 4.23 (2H, t, Fmoc $CH_2$), 5.37 (2H, brs, Cit $NH_2$), 5.92 (1H, t, Cit NH), 7.28–7.90 (8H, m, Ph), 8.15 (1H, d, amide NH); MS (FAB) 497 (MH)$^+$, 519 (M+Na)$^+$, 535 (M+K)$^+$; Accurate mass calc. for $C_{26}H_{33}N_4O_6$: 497.2400; found: 497.2394;

Anal. calc. for $C_{26}H_{32}N_4O_6$: C-62.89, H-6.50, N-11.28; Found: C-62.92, H-6.67, N-11.07.

EXAMPLE 57

Preparation of Fmoc-Val-Cit-PAB-OH (58)

Fmoc-Val-Cit (57) (1.0443 g, 2.103 mmoles) and p-aminobenzyl alcohol (518.0 mg, 2 equiv.) in 2:1 $CH_2Cl_2$/methanol (35 ml) were treated with EEDQ (1.0402 g, 2 equiv.). The mixture was stirred in the dark at room temperature for 1.5 days. The solvents were removed on the rotovap (bath temp. about 40° C.) and the white solid residue was triturated with ether (75 ml). The resulting suspension was sonicated for about 5 minutes and then left to stand for about 30 minutes. The solid was collected by filtration and washed repeatedly with ether (1.0070 g, 80%). $^1$H-NMR (DMSO-d$_6$) δ 0.88 (6H, t, Val CH$_3$), 1.41 and 1.65 (4H, m, Cit CH$_2$), 2.00 (1H, m, Val CH$_3$—CH), 2.99 (2H, m, Cit N—CH$_2$), 3.92 (1H, t, Fmoc CH), 4.24 (2H, d, Fmoc CH$_2$), 4.19–4.50 (2H, m, Val and Cit CO—CH), 4.43 (2H, d, PAB CH$_2$), 5.11 (1H, t, PAB OH), 5.42 (2H, brs, Cit NH$_2$), 5.98 (1H, t, Cit NH), 7.15–7.92 (12H, m, Ph), 8.12 (1H, d, amide NH), 9.99 (1H, brs, PAB NH); MS (FAB) 602 (MH)$^+$, 624 (M+Na)$^+$, 640 (M+K)$^+$; Accurate mass calc. for C$_{33}$H$_{40}$N$_5$O$_6$: 602.2979; found: 602.2977;

Anal. calc. for C$_{33}$H$_{39}$N$_5$O$_6$: C-65.87, H-6.53, N-11.64; Found: C-65.61, H-6.49, N-11.73.

EXAMPLE 58

Preparation of Val-Cit-PAB-OH (59)

Fmoc-Val-Cit-PAB-OH (58) (245.2 mg, 407.5 μmoles) in NMP (4 ml) at room temperature was treated with diethylamine (0.8 ml). The mixture was left to stand at room temperature for about 16 hours and then the solvents were removed on the rotovap (bath temp about 40° C.). The thick, oily residue was treated with CH$_2$Cl$_2$ (15 ml). With scraping and sonication the first-formed gum became a solid which was collected by filtration and washed with CH$_2$Cl$_2$ (141.6 mg, 92%). $^1$H-NMR (DMSO-d$_6$) δ 0.82 (6H, 2×d, Val CH$_3$), 1.39, 1.59 and 1.66 (4H, m, Cit CH$_2$), 1.92 (1H, m, Val CH$_3$—CH), 2.98 (1H, m, Val CO—CH), 3.03 (2H, d, Val NH$_2$), 4.45 (2H, d, PAB CH$_2$), 4.48 (1H, m, Cit CO—CH), 5.10 (1H, brt, PAB OH), 5.41 (2H, brs, Cit NH$_2$), 5.99 (1H, brt, Cit NH), 7.21 and 7.52 (each 2H, d, PAB Ph), 8.12 (1H, brd, amide NH), 10.03 (1H, brs, PAB NH); MS (FAB) 380 (MH)$^+$, 402 (M+Na)$^+$, 418 (M+K)$^+$.

EXAMPLE 59

Preparation of MC-Val-Cit-PAB-OH (60)

Val-Cit-PAB-OH (59) (136.8 mg, 360.5 μmoles) and MC-NHS (122.3 mg, 1.1 equiv.) in NMP (5 ml) at room temperature were left to stand for about 16 hours. The NMP was removed on the rotovap (bath temp. about 40° C.) and the thick, oily residue was triturated with ether (20 ml). The solid product was collected by filtration and washed repeatedly with ether (205.7 mg, 99.6%). $^1$H-NMR (DMSO-d$_6$) δ 0.82 (6H, ABq, Val CH$_3$), 1.10–1.90 (10H, m, Cit and caproyl CH$_2$), 1.92 (1H, m, Val CH$_3$—CH), 2.16 (2H, t, caproyl CO—CH$_2$), 2.98 (2H, m, Cit N—CH$_2$), 3.33 (2H, t, M—CH$_2$), 4.19 (1H, t, Val CO—CH), 4.38 (1H, m, Cit CO—CH), 4.42 (2H, brd, PAB CH$_2$), 5.10 (1H, brt, PAB OH), 5.42 (2H, brs, Cit NH$_2$), 5.97 (1H, brt, Cit NH), 6.99 (2H, s, M CH), 7.21 and 7.52 (each 2H, d, PAB Ph), 7.82 and 8.07 (each 1H, d, amide NH), 9.90 (1H, brs, PAB NH); MS (FAB) 573 (MH)$^+$, 595 (M+Na)$^+$, 611 (M+K)$^+$; Accurate mass calc. for C$_{28}$H$_{41}$N$_6$O$_7$: 573.3037; found: 573.3016.

EXAMPLE 60

Preparation of MC-Val-Cit-PABC-PNP (61)

MC-Val-Cit-PAB-OH (60) (112.4 mg, 196.3 μmoles) under argon at room temperature was dissolved in dry pyridine (3 ml). The solution was cooled to about 0° C. and p-nitrophenyl chloroformate (119 mg, 3 equiv.) in CH$_2$Cl$_2$ (2 ml) was added all at once. After about 10 minutes at about 0° C. the ice bath was removed and the mixture was stirred at room temperature for about 2 hours. Ethyl acetate (50 ml) and 15% citric acid (75 ml) were added. The organic phase was washed with more citric acid, water and brine, dried and evaporated to give a light-yellow gum. This was chromatographed on silica, eluting with 1) 20:1 and 2) 15:1 CH$_2$Cl$_2$/methanol, to give the product as a white solid (21.5 mg, 15%). $^1$H-NMR (CDCl$_3$/CD$_3$OD) δ 0.90 (6H, d, Val CH$_3$), 1.16–1.95 (10H, m, Cit and caproyl CH$_2$), 2.12 (1H, m, Val CH$_3$—CH), 2.23 (2H, t, caproyl CO—CH$_2$), 3.17 (2H, m, Cit N—CH$_2$), 3.48 (2H, t, M—CH$_2$), 4.20 (1H, m, Val CO—CH), 4.59 (1H, m, Cit CO—CH), 5.22 (2H, s, PAB CH$_2$), 6.66 (2H, s, M CH), 6.91 and 7.79 (each 1H, d, amide NH), 7.34 and 7.60 (each 2H, d, PAB Ph), 7.34 and 8.23 (each 2H, d, PNP Ph), 9.49 (1H, brs, PAB NH); MS (FAB) 738 (MH)$^+$, 760 (M+Na)$^+$, 776 (M+K)$^+$.

EXAMPLE 61

Preparation of MC-Val-Cit-PABC-DOX (62)

MC-Val-Cit-PABC-PNP (61) (21.2 mg, 28.7 μmoles) and DOX.HCl (18.3 mg, 1.1 equiv.) in NMP (1.5 ml) at room temperature were treated with diisopropylethylamine (5.5 μl, 1.1 equiv.). The mixture was left to stand in the dark at room temperature for 2 days and then CH$_2$Cl$_2$ (25 ml) was added. A fine precipitate formed. The suspension was stored in the freezer overnight and then the orange solid was collected by filtration and washed with CH$_2$Cl$_2$. TLC showed some product remaining in the mother liquors along with most of the close-moving impurities. The crude solid was chromatographed on silica, eluting with 1) 15:1, 2) 10:1 and 3) 5:1 CH$_2$Cl$_2$/methanol (the sample was loaded in a minimum amount of 2:1 CH$_2$Cl$_2$/methanol), to give the product as an orange solid (22.4 mg, 68%). $^1$H-NMR (CDCl$_3$/CD$_3$OD) δ 0.83 (6H, d, Val CH$_3$), 1.18 (3H, d, sugar CH$_3$), 1.20–1.86 (12H, m, Cit and caproyl CH$_2$, D-ring CH$_2$), 1.93 (1H, m, Val CH$_3$—CH), 2.12 (2H, m, D-ring CH$_2$), 2.17 (2H, t, caproyl CO—CH$_2$), 2.90–3.20 (4H, q and m, sugar CH$_2$ and Cit N—CH$_2$), 3.39 (2H, t, M—CH$_2$), 3.50 (1H, brs, HO—CH), 3.98 (3H, s, O—CH$_3$), 4.02 (1H, m, Val CO—CH), 4.05 (1H, m, sugar CH$_3$—CH), 4.46 (1H, m, Cit CO—CH), 4.68 (2H, s, CO—CH$_2$—OH), 4.88 (2H, q, PAB CH$_2$), 5.16 (1H, brs, anomeric CH), 5.39 (1H, brs, DOX Ph—CH), 6.62 (2H, s, M CH), 7.13 and 7.42 (each 2H, d, PAB Ph), 7.32, 7.71 and 7.92 (each 1H; d, t and d; DOX Ph); MS (FAB) 1141 (M)$^+$, 1164.6 (M+Na)$^+$, 1180 (M+K)$^+$; Accurate mass calc. for C$_{56}$H$_{67}$N$_7$O$_{19}$Na: 1164.4389; found: 1164.4363.

EXAMPLE 62

Preparation of N-Boc-aminocaproic acid (63)

6-Aminocaproic acid (5.2331 g, 39.89 mmoles) and NaHCO$_3$ (3.3514 g, 1 equiv.) in water (50 ml) were treated with d-t-butyl dicarbonate (9.58 g, 1.1 equiv.). The mixture was stirred at room temperature overnight and then water (150 ml) and sat. NaHCO$_3$ (5 ml) were added. The solution was extracted with ether (100 ml) and then solid citric acid (10 g) was added, giving an oily suspension. This was extracted with Ethyl acetate (3×). The combined organic phases were washed with water and brine, dried and evaporated to give a colorless oil which solidified under vacuum (9.23 g, quant.). $^1$H-NMR (DMSO-d$_6$) δ 1.10–1.55 (6H, m, caproyl CH$_2$), 1.33 (9H, s, CH$_3$), 2.28 (2H, m, CO—CH$_2$), 2.88 (2H, m, N—CH$_2$), 6.77 (1H, m, NH); MS (DCI) 232 (MH)$^+$, 176 (MH-C$_4$H$_9$)$^+$;

Anal. calc. for C$_{11}$H$_{21}$NO$_4$: C-57.12, H-9.15, N-6.06; Found: C-57.11, H-9.22, N-6.09.

EXAMPLE 63

Preparation of Boc-NH-C-NHS (64)

N-Boc-aminocaproic acid (63) (9.23 g, 39.9 mmoles) and NHS (5.05 g, 1.1 equiv.) in THF (75 ml) at room temperature were treated with DCC (9.05 g, 1.1 equiv.). The mixture was stirred at room temperature for about 16 hours and then the solid DCU by-product was filtered off. The filtrate was evaporated to give a thick oil which was dissolved in $CH_2Cl_2$ (150 ml). After standing for about 1 hour more DCU was filtered off. The filtrate was again evaporated and the thick oily residue dried in vacuo upon which it gradually solidified. The product was used without further purification (13.052 g, 99.6%).

EXAMPLE 64

Preparation of Boc-NH-C-Phe (65)

A solution of Boc-NH-C-NHS (64) (12.52 g, 38.13 mmoles) in DME (100 ml) was added to a solution of L-Phe (6.930 g, 1.1 equiv.) and $NaHCO_3$ (3.524 g, 1.1 equiv.) in water (100 ml) at room temperature THF (30 ml) was added to increase solubility. The mixture was stirred at room temperature for about 16 hours and then 15% citric acid (100 ml) was added. The suspension was extracted with 10% isopropanol/ethyl acetate (3×80 ml) and the combined organic phases were washed with water and brine, dried and evaporated to give a white solid. This was triturated with ether and the resulting white solid was collected by filtration and washed with ether (12.122 g, 84%). $^1$H-NMR (DMSO-$d_6$) δ 1.09 and 1.30 (6H, m, caproyl $CH_2$), 1.38 (9H, s, $CH_3$), 1.80–2.25 (2H, m, CO—$CH_2$), 2.82 (4H, m, Phe $CH_2$ and N—$CH_2$), 4.52 (1H, m, CO—CH), 6.73 (1H, m, NH), 7.20 (5H, m, Ph); MS (DCI) 379 $(MH)^+$, 323 $(MH-C_4H_9)^+$, 279 $(MH-C_5H_9O_2)^+$;

Anal. calc. for $C_{20}H_{30}N_2O_5$: C-63.47, H-7.99, N-7.40; Found: C-63.37, H-8.05, N-7.76.

EXAMPLE 65

Preparation of Boc-NH-C-Phe-NHS (66)

Boc-NH-C-Phe (65) (11.527 g, 30.46 mmoles) and NHS (3.86 g, 1.1 equiv.) in THF (100 ml) at about 0° C. were treated with DCC (6.913 g, 1.1 equiv.). The mixture was stirred at room temperature for about 16 hours and worked up as described above for Boc-NH-C-NHS (64) to give the product as a colorless glass which was used without further purification (14.369 g, 99.2%).

EXAMPLE 66

Preparation of Boc-NH-C-Phe-N-Fmoc-Lys (67)

Boc-NH-C-Phe-NHS (66) (14.369 g, 30.22 mmoles) in DME (100 ml) was added to a solution of $N^\epsilon$-Fmoc-Lys (11.222 g, 1 equiv.) and $NaHCO_3$ (2.560 g, 1 equiv.) in water (50 ml) and DME (50 ml). The mixture was stirred vigorously at room temperature for about 16 hours and then 15% citric acid (150 ml) and 10% isopropanol/ethyl acetate (250 ml) were added. The aqueous phase was extracted with more 10% isopropanol/ethyl acetate (2×100 ml). The combined organic phases were washed with water and brine, dried and evaporated to give an off-white solid. This was triturated with ether and the white, solid product was collected by filtration and washed with ether (17.842 g, 81%). $^1$H-NMR ($CDCl_3/CD_3OD$) δ 1.00–1.92 (12H, m, Lys and caproyl $CH_2$), 1.42 (9H, s, $CH_3$), 2.09 (2H, m, CO—$CH_2$), 2.96 (2H, m, Phe $CH_2$), 3.10 (2H, m, caproyl N—$CH_2$), 3.31 (2H, m, Lys N—$CH_2$), 4.18 (1H, t, Fmoc CH), 4.37 (2H, d, Fmoc $CH_2$), 4.46 and 4.71 (each 1H, m, Phe and Lys CO—CH), 7.10–7.80 (13H, m, Ph); MS (FAB) 729 $(MH)^+$, 751 $(M+Na)^+$, 767 $(M+K)^+$;

Anal. calc. for $C_{41}H_{52}N_4O_8$—$H_2O$: C-65.93, H-7.32, N-7.66; Found: C-66.07, H-7.32, N-7.66.

EXAMPLE 67

Preparation of Boc-NH-C-Phe-$N^\epsilon$-Fmoc-Lys-PAB-OH (68)

Boc-NH-C-Phe-$N^\epsilon$-Fmoc-Lys (67) (15.716 g, 21.56 mmoles) and p-aminobenzyl alcohol (3.983 g, 1.5 equiv.) in THF (100 ml) at room temperature were treated with EEDQ (8.000 g, 1.5 equiv.). The mixture was stirred at room temperature for about 16 hours and then evaporated to dryness (water bath temperature 30° C.). The residue was triturated with ether (100 ml) and the white, solid product was collected by filtration and washed with ether (16.453 g, 92%). $^1$H-NMR (DMSO-$d_6$) δ 0.90–1.80 (12H, m, Lys and caproyl $CH_2$), 1.35 (9H, s, $CH_3$), 2.00 (2H, t, CO—$CH_2$), 2.66–3.07 (6H, m, N—$CH_2$ and Phe $CH_2$), 4.19 (1H, m, Fmoc CH), 4.23 (2H, d, Fmoc $CH_2$), 4.36 and 4.58 (each 1H, m, Phe and Lys CO—CH), 4.41 (2H, s, PAB $CH_2$), 7.10–8.22 (17H, m, Ph), 9.94 (1H, brs, PAB NH); MS (FAB) 834 $(MH)^+$, 856 $(M+Na)^+$, 872 $(M+K)^+$;

Anal. calc. for $C_{48}H_{59}N_5O_8$-½$H_2O$: C-68.39, H-7.17, N-8.31; Found: C-68.18, H-7.12, N-8.42.

EXAMPLE 68

Preparation of MC-NH-C-Phe-$N^\epsilon$-Fmoc-Lys-PAB-OH (69)

Boc-NH-C-Phe-$N^\epsilon$-Fmoc-Lys-PAB-OH (60) (2.1323 g, 2.860 mmoles) was dissolved in 2:1 $CH_2Cl_2$/TFA (30 ml). The mixture was sonicated at room temperature for about 15 minutes and then left to stand for about 1 hour. The solvents were evaporated and the residual brown oil was dried in vacuo for about 1 hour. Ether (75 ml) was added and the oil was scraped until it solidified. The solid was collected by filtration, washed with ether and dried in vacuo for several hours. It was then dissolved in 3:1 DME/water (40 ml) and treated with a solution of MC-NHS (788.2 mg, 1 equiv.) in DME (20 ml) and solid $NaHCO_3$ (540 mg, 2.5 equiv.). The mixture was stirred at room temperature for about 16 hours. As much DME as possible was removed on the rotovap (water bath temp. about 30° C.), leaving a gummy solid (which eventually solidified) in water. The solid was filtered, washed with water and dried in vacuo. It was then triturated with ether (25 ml) and the solid product was collected by filtration and washed with ether (1.4283 g, 60%). $^1$H-NMR ($CDCl_3/CD_3OD$) δ 1.00–1.90 (18H, m, Lys and caproyl $CH_2$), 2.07 (4H, m, Phe $CH_2$ and CO—$CH_2$), 2.22 (2H, t, CO—$CH_2$), 3.05 (4H, m, Lys N—$CH_2$ and caproyl N—$CH_2$), 3.41 (2H, m, M—$CH_2$), 4.11 (1H, t, Fmoc CH), 4.28 (2H, d, Fmoc $CH_2$), 4.38 and 4.63 (each 1H, m, Phe and Lys CO—CH), 4.52 (2H, s, PAB $CH_2$), 5.61 (2H, s, M CH), 6.96–7.71 (17H, m, Ph); MS (FAB) 927.5 $(MH)^+$, 949.3 $(M+Na)^+$, 965.3 $(M+K)^+$; Accurate mass calc. for $C_{53}H_{63}N_6O_9$: 927.4657; found: 927.4642.

EXAMPLE 69

Preparation of MC-NH-C-Phe-$N^\epsilon$-Fmoc-Lys-PABC-PNP (70)

MC-NH-C-Phe-$N^\epsilon$-Fmoc-Lys-PAB-OH (69) (1.3783 g, 1.487 mmoles) and p-nitrophenyl chloroformate (449.5 mg, 1.5 equiv.) in $CH_2Cl_2$ (50 ml) at room temperature were treated with pyridine (0.18 ml, 1.5 equiv.). The suspension was sonicated at room temperature for about 30 minutes and then stirred for about 16 hours. More p-nitrophenyl chloroformate (150 mg, 0.5 equiv.) and pyridine (0.06 ml, 0.5 equiv.) were added and the mixture was again sonicated for about 30 minutes and stirred for about 4 hours. Workup as described above for MC-Val-Cit-PABC-PNP (61) gave the crude product as a gummy solid. This was chromatographed on silica, eluting with 1) 35:1, 2) 25:1 and 3) 20:1 $CH_2Cl_2$/methanol, to give the product as a pale-yellow, gummy solid (593.1 mg, 0.543 mmoles). $^1$H-NMR ($CDCl_3/CD_3OD$) δ 1.10–1.95 (18H, m, Lys and caproyl $CH_2$), 2.12 (4H, m, caproyl $CO—CH_2$), 3.00 (2H, m, Phe $CH_2$), 3.11 (4H, m, Lys and caproyl $N—CH_2$), 3.44 (2H, t, $M—CH_2$), 4.13 (1H, t, Fmoc CH), 4.32 (2H, d, Fmoc $CH_2$), 4.39 and 4.63 (each 1H, m, Phe and Lys CO—CH), 5.18 (2H, s, PAB $CH_2$), 6.63 (2H, s, M CH), 7.00–8.25 (21H, m, Ph); MS (FAB): 1114 $(M+Na)^+$, 1130 $(M+K)^+$; Accurate mass calc. for $C_{60}H_{66}N_7O_{13}$: 1092.4719; found: 1092.4680.

EXAMPLE 70

Preparation of MC-NH-C-Phe-N$^ε$-Fmoc-Lys-PABC-DOX (71)

MC-NH-C-Phe-N$^ε$-Fmoc-Lys-PABC-PNP (70) (382.8 mg, 0.350 mmoles) and DOX.HCl (213 mg, 1.05 equiv.) in NMP (16 ml) were treated with diisopropylethylamine (61 μl, 1 equiv.). The mixture was allowed to stand in the dark for 2 days. Workup as described above for MC-Val-Cit-PABC-DOX (62) gave the product as an orange glass (293.1 mg, 56%). $^1$H-NMR ($CDCl_3/CD_3OD$) δ 1.00–1.85 (20H, m, Lys and caproyl $CH_2$, D-ring $CH_2$), 1.21 (3H, d, sugar $CH_3$), 2.09 (4H, m, caproyl $CO—CH_2$), 2.17 (2H, m, D-ring $CH_2$), 2.80–3.27 (8H, m, Lys and caproyl $N—CH_2$, sugar $CH_2$, Phe $CH_2$), 3.40 (2H, t, $M—CH_2$), 3.53 (1H, brs, HO—CH), 3.78 (1H, m, sugar N—CH), 3.99 (3H, s, O—$CH_3$), 4.11 (2H, t, Fmoc CH and sugar $CH_3$—CH), 4.29 (2H, d, Fmoc $CH_2$), 4.33 and 4.57 (each 1H, m, Phe and Lys CO—CH), 4.71 (2H, s, $CO—CH_2$—OH), 4.89 (2H, q, PAB $CH_2$), 5.20 (1H, brs, anomeric CH), 5.42 (1H, brs, DOX Ph—CH), 6.60 (2H, s, M CH), 6.90–8.00 (20H, m, Ph); MS (FAB) 1519 $(M+Na)^+$, 1534 $(M+K)^+$; Accurate mass calc. for $C_{81}H_{89}N_7O_{21}Na$: 1518.6009; found: 1518.5962.

EXAMPLE 71

Preparation of MC-NH-C-Phe-Lys-PABC-DOX.HCl (72)

MC-NH-C-Phe-N$^ε$-Fmoc-Lys-PABC-DOX (71) (95.2 mg, 63.6 μmoles) in NMP (0.3 ml) was diluted with THF (10 ml) and then, with stirring, treated with 2% DBU in THF (10 ml). After about 45 seconds ether (40 ml) was added and the resulting blue solid was collected by filtration and washed with ether. The solid was resuspended in ether (10 ml) and treated with 1M HCl in ether (10 ml). After several minutes the orange solid was filtered off, washed repeatedly with ether and triturated with $CH_2Cl_2$ (25 ml). The resulting orange-red solid was collected by filtration and chromatographed on LH-20 lipophilic SEPHADEX, eluting with 1:1 $CH_2Cl_2$/methanol. The product-containing fractions were combined and re-chromatographed on LH-20, eluting with methanol, to give the product as an orange glass, with minor contaminents as shown by HPLC (40.2 mg, 48.2%). $^1$H-NMR ($CDCl_3/CD_3OD$) δ (selected peaks) 1.00–1.95 (23H, m, sugar $CH_3$, Lys and caproyl $CH_2$, D-ring $CH_2$), 2.00–2.40 (6H, m, caproyl $CO—CH_2$ and D-ring $CH_2$), 2.96 (2H, m, $^+H_3N—CH_2$), 4.05 (3H, s, O—$CH_3$), 4.72 (2H, s, $CO—CH_2$—OH), 4.93 (2H, brs, PAB $CH_2$), 5.17 (1H, brs, anomeric CH), 5.42 (1H, brs, DOX Ph—CH), 6.63 (2H, brs, M CH), 6.90–8.20 (12H, m, Ph).

EXAMPLE 72

Preparation of Fmoc-Phe-N$^ε$-Mtr-Lys-NHS (73)

A stirred mixture of Fmoc-Phe-N$^ε$-Mtr-Lys (44) (1.8873 g, 2.40 mmoles) and NHS (303.2 mg, 1.1 equiv.) in $CH_2Cl_2$ (40 ml) at about 0° C. was treated with DCC (543.6 mg, 1.1 equiv.). After about 24 hours at room temperature the DCU was filtered off and the filtrate evaporated and the residue taken up in ethyl acetate. This was washed with water (2×) and brine, dried and evaporated. The residue was chromatographed on silica, eluting with 1:1 ethyl acetate/hexane. Much of the product decomposed on the column (472.5 mg, 22%). $^1$H-NMR ($CDCl_3$) δ 1.00–1.98 (6H, m, $CH_2$), 2.01 (2H, t, N—$CH_2$), 2.77 (4H, brs, NHS $CH_2$), 3.09 (2H, m, Phe $CH_2$), 3.76 (3H, s, O—$CH_3$), 4.10–4.51 (4H, m, Fmoc $CH_2$ and CH, Phe CO—CH), 4.83 (1H, m, Lys CO—CH), 5.48 and 6.41 (each 1H, m, NH), 6.79 (2H, d, MeOPh o-CH), 7.06–7.80 (25H, m, Ph).

EXAMPLE 73

Preparation of Fmoc-Phe-N$^ε$-Mtr-Lys-GABA (74)

A solution of Fmoc-Phe-N$^ε$-Mtr-Lys-NHS (73) (472.5 mg, 0.534 mmoles) in DME (25 ml) was added to a stirred solution of GABA (83 mg, 1.5 equiv.) and $NaHCO_3$ (67 mg, 1.5 equiv.) in water (15 ml) at room temperature. After 16 hours at room temperature as much DME as possible was removed on the rotovap and the resulting suspension was partitioned between ethyl acetate and pH 5 buffer. The organic phase was washed with water and brine, dried and evaporated. The residue was triturated with ether and the resulting white solid collected by filtration (387.0 mg, 83%). $^1$H-NMR ($CDCl_3$) δ 0.96–1.99 (8H, m, $CH_2$), 2.10–2.42 (4H, m, Lys N—$CH_2$ and CO—$CH_2$), 3.03 (2H, m, Phe $CH_2$), 3.22 (2H, m, GABA N—$CH_2$), 4.03–4.66 (5H, m, Fmoc $CH_2$ and CH, CO—CH), 6.78 (2H, d, MeOPh o-CH), 7.00–7.77 (25H, m, Ph); MS (FAB) 895 $(M+Na)^+$, 911 $(M+K)^+$.

EXAMPLE 74

Preparation of Fmoc-Phe-N$^ε$-Mtr-Lys-GABA-MMC (75)

A stirred mixture of Fmoc-Phe-N-Mtr-Lys-GABA (74) (296.9 mg, 0.340 mmoles), HOBt (46 mg, 1 equiv.) and MMC (119.4 mg, 1.05 equiv.) in NMP (3 ml) and $CH_2Cl_2$ (3 ml) at room temperature was treated with DCC (77.2 mg, 1.1 equiv.). After about 14 hours at room temperature ethyl acetate was added and the solution was washed with water (3×) and brine, dried and evaporated. The residue was chromatographed on silica, eluting with 25:1 $CH_2Cl_2$/methanol, to give the product as a purple glass (303.1 mg, 75%). $^1$H-NMR ($CDCl_3$) δ 0.97–1.90 (8H, m, $CH_2$), 1.71 (3H, s, MMC $CH_3$), 2.08 (2H, m, Lys N—$CH_2$), 2.46 (2H, m, CO—$CH_2$), 2.99 (2H, m, Phe $CH_2$), 3.12 (2H, m, GABA N—$CH_2$), 3.20 (3H, s, MMC O—$CH_3$), 3.28–3.55 (3H, m, C-1, C-2 and C-3 CH), 3.68 (1H, ABq, C-9 CH), 3.73 (3H, s, Mtr O—$CH_3$), 4.04–4.51 and 4.64 (7H, m, Fmoc $CH_2$ and CH, C-10 $CH_2$, CO—CH), 5.14 (2H, br, $NH_2$), 5.38, 5.49, 5.70 and 6.67 (each 1H, br, NH), 6.79 (2H, d, MeOPh o-CH), 7.03–7.78 (25H, m, Ph); MS (FAB) 1189.8 $(MH)^+$, 1211 $(M+Na)^+$, 1227.5 $(M+K)^+$.

EXAMPLE 75

Preparation of Phe-N$^\epsilon$-Mtr-Lys-GABA-MMC (76)

Fmoc-Phe-N$^\epsilon$-Mtr-Lys-GABA-MMC (75) (236.1 mg, 0.198 mmoles) in CH$_2$Cl$_2$ (2 ml) at room temperature was treated with diethylamine (2 ml). After about 3 hours the solvents were evaporated and the residue was flushed with CH$_2$Cl$_2$ (10 ml). The residue was chromatographed on silica, eluting with 1) 25:1 and 2) 15:1 CH$_2$Cl$_2$/methanol, to give the product as a purple glass (157.4 mg, 82%). $^1$H-NMR (CDCl$_3$) δ 1.15–1.83 (8H, m, CH$_2$), 1.77 (3H, s, MMC CH$_3$), 2.10 (2H, t, Lys N—CH$_2$), 2.46 (2H, m, CO—CH$_2$), 2.69 and 3.21 (each 1H, ABq, Phe CH$_2$), 3.19 (3H, s, MMC O—CH$_3$), 3.20–3.53 (5H, m, GABA N—CH$_2$, C-1, C-2 and C-3 CH), 3.48 (2H, brs, NH$_2$), 3.68 (2H, m, C-9 CH and Phe CO—CH), 3.76 (3H, s, Mtr O—CH$_3$), 4.09 and 4.82 (each 1H, t and ABq, C-10 CH$_2$), 4.29 (1H, m, Lys CO—CH), 4.41 (1H, d, C-3 CH), 5.29 (2H, brs, NH$_2$), 6.60 (1H, brt, GABA NH), 6.79 (2H, d, MeOPh o-CH), 7.10–7.48 (17H, m, Ph), 7.72 (1H, d, amide NH); MS (FAB) 967.4 (MH)$^+$, 989.2 (M+Na)$^+$, 1005.3 (M+K)$^+$.

EXAMPLE 76

Preparation of MC-Phe-N$^\epsilon$-Mtr-Lys-GABA-MMC (77)

A solution of Phe-N$^\epsilon$-Mtr-Lys-GABA-MMC (76) (108.9 mg, 0.113 mmoles) in CH$_2$Cl$_2$ (15 ml) was added to MC-NHS (0.124 mmoles). The mixture was stirred at room temperature for 3 days and then the solvent was evaporated. The residue was chromatographed on silica, eluting with 1) 20:1 and 2) 15:1 CH$_2$Cl$_2$/methanol, to give the product as a purple glass (75.8 mg, 58%). $^1$H-NMR (CDCl$_3$) δ 1.05–1.90 (14H, m, CH$_2$), 1.76 (3H, s, MMC CH$_3$), 2.07 (4H, m, Lys N—CH$_2$ and caproyl CO—CH$_2$), 2.49 (2H, m, GABA CO—CH$_2$), 2.98 and 3.20 (each 1H, ABq, Phe CH$_2$), 3.19 (2H, m, GABA N—CH$_2$), 3.23 (3H, s, MMC O—CH$_3$), 3.33 (2H, t, M—CH$_2$), 3.20–3.53 (3H, m, C-1, C-2 and C-3 CH), 3.68 (1H, ABq, C-9 CH), 3.78 (3H, s, Mtr O—CH$_3$), 4.11 and 4.62 (each 1H, t and ABq, C-10 CH$_2$), 4.24 (1H, m, Lys CO—CH), 4.49 (1H, d, C-3 CH), 5.19 (2H, br, NH$_2$), 6.27 (1H, d, NH), 6.67 (2H, s, M CH), 6.72 (1H, brt, NH), 6.80 (2H, d, MeOPh o-CH), 7.10–7.47 (17H, m, Ph), 7.19 (1H, d, NH).

EXAMPLE 77

Preparation of MC-Phe-Lys-GABA-MMC . ClCH$_2$CO$_2$H (78)

MC-Phe-N$^\epsilon$-Mtr-Lys-GABA-MMC (77) (43.2 mg, 37.2 μmoles) in CH$_2$Cl$_2$ (2 ml) was treated with anisole (0.405 ml, 100 equiv.) and chloroacetic acid (1M in CH$_2$Cl$_2$, 0.40 ml, 11 equiv.). After about 3 hours ether (5 ml) was added and the mixture was stored in the freezer for about 1 hour. The resulting solid was collected by filtration, washed with ether, and triturated with CH$_2$Cl$_2$ (36.1 mg, 99%). $^1$H-NMR (CDCl$_3$/CD$_3$OD) δ 1.03–1.82 (8H, m, CH$_2$), 1.71 (3H, s, MMC CH$_3$), 2.08 (2H, t, caproyl CO—CH$_2$), 2.40 (2H, brt, GABA CO—CH$_2$), 2.83 (4H, m, GABA N—CH$_2$ and N$^+$—CH$_2$), 3.39 (2H, t, M—CH$_2$), 3.59 (1H, ABq, C-9 CH) 3.95 (1H, t, C-10 CH$_2$), 4.18 (1H, m, Lys CO—CH), 4.42 (1H, d, C-3 CH), 4.67 (2H, m, Phe CO—CH and C-10 CH$_2$), 6.63 (2H, s, M CH), 7.17 (5H, m, Ph); HPLC: (C-18, 15 cm column, 65:35 methanol/50 mM triethylammonium formate buffer (pH 2.8), 1 ml/min., 360 nm): single peak, retention time: 2.19 min.

EXAMPLE 78

Preparation of Taxol-2'-ethyl carbonate-7-chloroformate (83)

A stirred solution of taxol-2'-ethyl carbonate (82) (154.2 mg, 0.1665 mmoles) in CH$_2$Cl$_2$ (3 ml) at 0° C. under argon was treated with pyridine (13.5 μl, 1 equiv.) and then diphosgene (10.0 μl, 0.5 equiv.). The ice bath was removed and the mixture was stirred at room temperature for one hour and then re-cooled to 0° C. and used immediately.

EXAMPLE 79

Preparation of MC-Phe-N$^\epsilon$-Mtr-Lys-PABC-7-Taxol-2'-ethyl carbonate (84)

A solution of MC-Phe-N$^\epsilon$-Mtr-Lys-PAB-OH (47) (143.9 mg, 0.1665 mmoles) in CH$_2$Cl$_2$ (4 ml) was added to the above solution of taxol-2'-ethyl carbonate-7-chloroformate (83) (0.1665 mmoles) at about 0° C. The ice bath was removed and the mixture was stirred at room temperature for about 3 hours. Ethyl acetate was then added and the solution was washed with pH 5 buffer, water, and brine, dried and evaporated to give a colorless glass which was chromatographed on silica, eluting with 1) 2:1 and 2) 1:1 CH$_2$Cl$_2$/ethyl acetate, to give the product as a colorless glass (251.0 mg, 83%). $^1$H-NMR (CDCl$_3$) δ 1.16, 1.21 and 1.78 (each 3H, s, C-16, C-17 and C-19 CH$_3$), 1.10–1.90 (12H, m, Lys and caproyl CH$_2$), 1.31 (3H, t, ethyl CH$_3$), 1.91 and 2.60 (each 1H, m, C-6 CH$_2$), 2.04 (3H, s, C-18 CH$_3$), 2.12 (4H, t, Lys N—CH$_2$ and caproyl CO—CH$_2$), 2.18 and 2.48 (each 3H, s, Ac CH$_3$), 2.22 and 2.40 (each 1H, m, C-14 CH$_2$), 3.03 (2H, m, Phe CH$_2$), 3.42 (2H, t, caproyl N—CH$_2$), 3.97 (1H, d, C-3 CH), 4.29 (2H, m, C-20 CH$_2$), 4.21 (2H, q, ethyl CH$_2$), 4.46 and 4.72 (each 1H, m, Phe and Lys CO—CH), 4.96 (1H, d, C-5 CH), 5.16 (2H, q, PAB CH$_2$), 5.44 (1H, d, C-2' CH), 5.56 (1H, m, C-7 CH), 5.70 (1H, d, C-2 CH), 5.97 (1H, m, C-3' CH), 6.26 (1H, m, C-13 CH), 6.40 (1H, s, C-10 CH), 6.65 (2H, s, M CH), 6.78 (2H, d, MeOPh o-CH), 6.98 and 7.60 (each 1H, d, NH), 7.04–8.20 (31H, m, Ph), 8.38 (1H, brs, PAB NH); MS (FAB) 1837.2 (M+Na)$^+$, 1853.5 (M+K)$^+$.

EXAMPLE 80

Preparation of MC-Phe-Lys-PABC-7-Taxol-2'-ethyl carbonate.ClCH$_2$CO$_2$H (85)

A stirred solution of MC-Phe-N$^\epsilon$-Mtr-Lys-PABC-7-Taxol-2'-ethyl carbonate (84) (80.2 mg, 44.2 μmoles) in CH$_2$Cl$_2$ (3.5 ml) at room temperature was treated with anisole (0.48 ml, 100 equiv.) and chloroacetic acid (1M in CH$_2$Cl$_2$, 0.442 ml, 10 equiv.). After about 3 hours ether (15 ml) was added and the mixture was stored in the freezer for about 2 hours. The resulting white solid was collected by filtration and washed with ether (72.2 mg, 99%). $^1$H-NMR (CDCl$_3$) δ 1.16, 1.20 and 1.80 (each 3H, s, C-16, C-17 and C-19 CH$_3$), 1.10–1.90 (12H, m, Lys and caproyl CH$_2$), 1.30 (3H, t, ethyl CH$_3$), 1.91 and 2.58 (each 1H, m, C-6 CH$_2$), 2.02 (3H, s, C-18 CH$_3$), 2.13 (2H, m, caproyl CO—CH$_2$), 2.17 and 2.45 (each 3H, s, Ac CH$_3$), 2.20 and 2.39 (each 1H, m, C-14 CH$_2$), 2.97 (2H, m, Lys N—CH$_2$), 3.01 (2H, m, Phe CH$_2$), 3.42 (2H, t, caproyl N—CH$_2$), 3.97 (1H, d, C-3 CH), 4.29 (4H, m, C-20 CH$_2$ and ethyl CH$_2$), 4.56 and 4.83 (each 1H, m, Phe and Lys CO—CH), 4.95 (1H, d, C-5 CH), 5.17 (2H, q, PAB CH$_2$), 5.42 (1H, d, C-2' CH), 5.54 (1H, m, C-7 CH), 5.69 (1H, d, C-2 CH), 5.97 (1H, m, C-3' CH), 6.29 (1H, m, C-13 CH), 6.41 (1H, s, C-10 CH), 6.66 (2H, s, M CH), 6.98 and 8.39 (each 1H, d, NH), 7.08–8.14 (19H, m, Ph), 9.25 (1H, brs, PAB NH).

EXAMPLE 81

Conjugate Synthesis

A solution (10 ml) of mAb BR96 (10.46 mg/ml, 6.54× $10^{-5}$M; concentration determined by UV absorption at 280 nm, 1 mg/ml of mAb equals 1.4 abs. units) in 0.125M potassium phosphate buffer was treated with a freshly prepared solution (0.523 ml) of 10 mM dithiothreitol (DTT) at about 37° C. for about 3 hours under nitrogen. The solution was transferred to an Amicon cell and was diafiltrated against phosphate buffered saline (PBS) until the effluent was free of SH groups (Ellman reagent). The mAb and SH group concentration was determined (10.11 mg/ml (6.32× $10^{-5}$M) and 4.48×$10^{-4}$M, respectively, representing a molar ratio (MR) of SH to mAb of 7.01). This solution was treated with MC-Phe-Lys-PABC-DOX (5 mg/ml, 4.77×$10^{-3}$M) in distilled water (1.2 ml), then left to stand overnight at about 4° C. The solution was transferred to a dialysis tube and dialyzed 3 times against 1 L PBS for about 24 hours at about 4° C. The conjugate solution was filtered through a MILLEX-GV 0.22 μm filter unit (Millipore Corp.), and the filtrate was shaken gently for several hours with Bio-beads (Bio-Rad Laboratories), followed by another filtration through a MILLIVEXX-GV unit. The concentration of DOX was determined from the UV absorbance at 495 nm ($\epsilon$=8030, 283 μm, 164 μg/ml) and that of the mAb at 280 nm with a correction for DOX absorbance at 280 nm according to the formula:

$$mAb\,(mg/ml) = \frac{A280 - (0.724 \times A495)}{1.4}$$

where A is the observed absorbance at the noted wavelength.

EXAMPLE 82

A solution of Phe-($N^\epsilon$-MTR)Lys-PABC-DOX in an appropriate solvent is treated with an equivalent amount of N-Succinimidyl p-(iodoacetamido)benzoate. The solution is kept at about 30° C. for about 1 hour and then the solvent is evaporated under reduced pressure. The protecting group MTR is removed from the peptide in the usual manner and the iodoacetylated peptide is dissolved in water or an organic water miscible solvent to a known concentration. An appropriate amount of this solution is added to a solution of thiolated mAb BR96 in PBS to react with all thiol groups generated in the mAb. The solution is kept at about 4° C. for about one hour and then chromatographed over a size exclusion column to eliminate low molecular weight compounds from the conjugate. Finally the conjugate solution is shaken with a small amount of Bio-Beads for a few hours, then filtered through a 0.22 micron filter. The concentration of mAb and DOX is determined from their absorption at 280 and 495 nm, respectively and the MR of drug to mAb is calculated.

EXAMPLE 83

A solution of Phe-($N^\epsilon$-MTR)Lys-PABC-DOX in an appropriate solvent is treated with an equivalent amount of N-Succinimidyl-3-(2-pyridynyldithio)-propionate (SPDP). The solution is kept at about 30° C. for about 1 hour and then the solvent is evaporated under reduced pressure. The protecting group MTR is removed from the peptide in the usual manner and the peptide is dissolved in water or an organic water miscible solvent to a known concentration. An appropriate amount of this solution is added to a solution of thiolated mAb BR96 in PBS to react with all thiol groups generated in the mAb. The solution is kept at about 4° C. for about one hour and then chromatographed over a size exclusion column to eliminate low molecular weight compounds from the conjugate. Finally the conjugate solution is shaken with a small amount of Bio-Beads for a few hours, then filtered through a 0.22 micron filter. The concentration of mAb and DOX is determined from their absorption at 280 and 495 nm, respectively and the MR of drug to mAb is calculated.

The invention has been described with reference to specific examples, materials and data. As one skilled in the art will appreciate, alternate means for using or preparing the various aspects of the invention may be available. Such alternate means are to be construed as included within the intent and spirit of the present invention as defined by the following claims.

We claim:

1. A compound of the Formula (I):

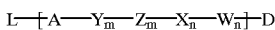

in which

L is a ligand, wherein L is capable of specifically targeting a selected cell population;

A is a carboxylic acyl unit;

Y is an amino acid;

Z is an amino acid;

X and W are each a self-immolative spacer;

D is a drug moiety having pendant to the backbone thereof a chemically reactive functional group, said functional group selected from the group consisting of a primary or secondary amine, hydroxyl, sulfhydryl, carboxyl, aldehyde and a ketone;

n is an integer of 0 or 1, with the proviso that n cannot be the integer 0 for both $X_n$ and $W_n$; and m is an integer of 1, 2, 3, 4, 5 or 6;

and wherein Y and Z comprise a protein peptide sequence which is selectively enzymatically cleavable by tumor associated proteases.

2. A compound of claim 1 in which Y is an amino acid selected from the group consisting of alanine, valine, leucine, isoleucine, methionine, phenylalanine, tryptophan and proline.

3. A compound of claim 1 in which Z an amino acid selected from the group consisting of lysine, lysine protected with acetyl or formyl, arginine, arginine protected with tosyl or nitro groups, histidine, ornithine, ornithine protected with acetyl or formyl, and citrulline.

4. A compound of claim 1 in which the

group is phenylalanine-lysine.

5. A compound of claim 1 in which the

group is valine-citrulline.

6. A compound of claim 1 in which the

group is valine-lysine.

7. A compound of claim 2 in which Y is phenylalanine.
8. A compound of claim 2 in which Y is valine.
9. A compound of claim 3 in which Z is lysine.
10. A compound of claim 3 in which Z is citrulline.
11. The compound of claim 1 in which D is a cytotoxic drug.
12. The compound of claim 2 in which D is a cytotoxic drug.
13. The compound of claim 3 in which D is a cytotoxic drug.
14. The compound of claim 4 in which D is a cytotoxic drug.
15. The compound of claim 5 in which D is a cytotoxic drug.
16. The compound of claim 6 in which D is a cytotoxic drug.
17. A compound of claim 1 in which D is an amino containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, and derivatives thereof.
18. A compound of claim 2 in which D is an amino containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, and derivatives thereof.
19. A compound of claim 3 in which D is an amino containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, and derivatives thereof.
20. A compound of claim 4 in which D is an amino containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1- (2 chloroethyl)-1,2-dimethanesulfonyl hydrazide, tallysomycin, and derivatives thereof.
21. A compound of claim 5 in which D is an amino containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, and derivatives thereof.
22. A compound of claim 6 in which D is an amino containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, $N^8$-acetyl spermidine, 1-(2 chloroethyl)-1,2-dimethanesulfonyl hydrazide, tallysomycin, and derivatives thereof.

23. A compound of claim 17 in which D is doxorubicin.
24. A compound of claim 18 in which D is doxorubicin.
25. A compound of claim 19 in which D is doxorubicin.
26. A compound of claim 20 in which D is doxorubicin.
27. A compound of claim 21 in which D is doxorubicin.
28. A compound of claim 22 in which D is doxorubicin.
29. A compound of claim 17 in which D is mitomycin-C.
30. A compound of claim 18 in which D is mitomycin-C.
31. A compound of claim 19 in which D is mitomycin-C.
32. A compound of claim 20 in which D is mitomycin-C.
33. A compound of claim 21 in which D is mitomycin-C.
34. A compound of claim 22 in which D is mitomycin-C.
35. A compound of claim 17 in which D is mitomycin-A.
36. A compound of claim 18 in which D is mitomycin-A.
37. A compound of claim 19 in which D is mitomycin-A.
38. A compound of claim 20 in which D is mitomycin-A.
39. A compound of claim 21 in which D is mitomycin-A.
40. A compound of claim 22 in which D is mitomycin-A.
41. A compound of claim 17 in which D is tallysomycin.
42. A compound of claim 18 in which D is tallysomycin.
43. A compound of claim 19 in which D is tallysomycin.
44. A compound of claim 20 in which D is tallysomycin.
45. A compound of claim 21 in which D is tallysomycin.
46. A compound of claim 22 in which D is tallysomycin.
47. A compound of claim 17 in which D is N-(5,5-diacetoxypentyl)doxorubicin.
48. A compound of claim 18 in which D is N-(5,5-diacetoxypentyl)doxorubicin.
49. A compound of claim 19 in which D is N-(5,5-diacetoxypentyl)doxorubicin.
50. A compound of claim 20 in which D is N-(5,5-diacetoxypentyl)doxorubicin.
51. A compound of claim 21 in which D is N-(5,5-diacetoxypentyl)doxorubicin.
52. A compound of claim 22 in which D is N-(5,5-diacetoxypentyl)doxorubicin.
53. A compound of claim 1 in which D is a hydroxyl containing drug moiety selected from the group consisting of etoposide, camptothecin, taxol, esperamicin, 1,8-dihydroxy-bicyclo[7.3.1]trideca-4,9-diene-2,6-diyne-13-one, anguidine, doxorubicin, morpholino-doxorubicin, N-(5,5-diacetoxypentyl)doxorubicin, vincristine, vinblastine and derivatives thereof.
54. A compound of claim 2 in which D is a hydroxyl containing drug moiety selected from the group consisting of etoposide, camptothecin, taxol, esperamicin, 1,8-dihydroxy-bicyclo[7.3.1]trideca-4,9-ene-2,6-diyne-13-one, anguidine, doxorubicin, morpholino-doxorubicin, N-(5,5-diacetoxypentyl)doxorubicin, vincristine, vinblastine and derivatives thereof.
55. A compound of claim 3 in which D is a hydroxyl containing drug moiety selected from the group consisting of etoposide, camptothecin, taxol, esperamicin, 1,8-dihydroxy-bicyclo[7.3.1]trideca-4,9-ene-2,6-diyne-13-one, anguidine, doxorubicin, morpholino-doxorubicin, N-(5,5-diacetoxypentyl)doxorubicin, vincristine, vinblastine and derivatives thereof.
56. A compound of claim 4 in which D is a hydroxyl containing drug moiety selected from the group consisting of etoposide, camptothecin, taxol, esperamicin, 1,8-dihydroxy-bicyclo[7.3.1]trideca-4,9-ene-2,6-diyne-13-one, anguidine, doxorubicin, morpholino-doxorubicin, N-(5,5-diacetoxypentyl)doxorubicin, vincristine, vinblastine and derivatives thereof.
57. A compound of claim 5 in which D is a hydroxyl containing drug moiety selected from the group consisting of etoposide, camptothecin, taxol, esperamicin, 1,8-dihydroxy-bicyclo[7.3.1]trideca-4,9-ene-2,6-diyne-13-one, anguidine, doxorubicin, morpholino-doxorubicin, N-(5,5-diacetoxypentyl)doxorubicin, vincristine, vinblastine and derivatives thereof.
58. A compound of claim 6 in which D is a hydroxyl containing drug moiety selected from the group consisting of etoposide, camptothecin, taxol, esperamicin, 1,8-dihydroxy-bicyclo[7.3.1]trideca-4,9-ene-2,6-diyne-13-one, anguidine, doxorubicin, morpholino-doxorubicin, and derivatives thereof.
59. A compound of claim 53 in which D is taxol.
60. A compound of claim 54 in which D is taxol.
61. A compound of claim 55 in which D is taxol.
62. A compound of claim 56 in which D is taxol.
63. A compound of claim 57 in which D is taxol.
64. A compound of claim 58 in which D is taxol.
65. A compound of claim 53 in which D is etoposide.
66. A compound of claim 54 in which D is etoposide.
67. A compound of claim 55 in which D is etoposide.
68. A compound of claim 56 in which D is etoposide.
69. A compound of claim 57 in which D is etoposide.
70. A compound of claim 58 in which D is etoposide.
71. A compound of claim 53 in which D is morpholino-doxorubicin.
72. A compound of claim 54 in which D is morpholino-doxorubicin.
73. A compound of claim 55 in which D is morpholino-doxorubicin.
74. A compound of claim 56 in which D is morpholino-doxorubicin.
75. A compound of claim 57 in which D is morpholino-doxorubicin.
76. A compound of claim 58 in which D is morpholino-doxorubicin.
77. A compound of claim 53 in which D is N-(5,5-diacetoxypentyl)doxorubicin.
78. A compound of claim 54 in which D is N-(5,5-diacetoxypentyl)doxorubicin.
79. A compound of claim 55 in which D is N-(5,5-diacetoxypentyl)doxorubicin.
80. A compound of claim 56 in which D is N-(5,5-diacetoxypentyl)doxorubicin.
81. A compound of claim 57 in which D is N-(5,5-diacetoxypentyl)doxorubicin.
82. A compound of claim 58 in which D is N-(5,5-diacetoxypentyl)doxorubicin.
83. A compound of claim 1 in which D is a sulfhydryl containing drug moiety selected from the group consisting of esperamicin, 6-mercaptopurine, or derivatives thereof.
84. A compound of claim 2 in which D is a sulfhydryl containing drug moiety selected from the group consisting of esperamicin, 6-mercaptopurine, or derivatives thereof.
85. A compound of claim 3 in which D is a sulfhydryl containing drug moiety selected from the group consisting of esperamicin, 6-mercaptopurine, or derivatives thereof.
86. A compound of claim 4 in which D is a sulfhydryl containing drug moiety selected from the group consisting of esperamicin, 6-mercaptopurine, or derivatives thereof.
87. A compound of claim 5 in which D is a sulfhydryl containing drug moiety selected from the group consisting of esperamicin, 6-mercaptopurine, or derivatives thereof.
88. A compound of claim 6 in which D is a sulfhydryl containing drug moiety selected from the group consisting of esperamicin, 6-mercaptopurine, or derivatives thereof.
89. A compound of claim 1 in which D is a carboxyl containing drug moiety selected from the group consisting of methotrexate, camptothecin (ring-opened form of the lactone), butyric acid, retinoic acid, and derivatives thereof.

90. A compound of claim 2 in which D is a carboxyl containing drug moiety selected from the group consisting of methotrexate, camptothecin (ring-opened form of the lactone), butyric acid, retinoic acid, and derivatives thereof.

91. A compound of claim 3 in which D is a carboxyl containing drug moiety selected from the group consisting of methotrexate, camptothecin (ring-opened form of the lactone), butyric acid, retinoic acid, and derivatives thereof.

92. A compound of claim 4 in which D is a carboxyl containing drug moiety selected from the group consisting of methotrexate, camptothecin (ring-opened form of the lactone), butyric acid, retinoic acid, and derivatives thereof.

93. A compound of claim 5 in which D is a carboxyl containing drug moiety selected from the group consisting of methotrexate, camptothecin (ring-opened form of the lactone), butyric acid, retinoic acid, and derivatives thereof.

94. A compound of claim 6 in which D is a carboxyl containing drug moiety selected from the group consisting of methotrexate, camptothecin (ring-opened form of the lactone), butyric acid, retinoic acid, and derivatives thereof.

95. A compound of claim 89 in which D is camptothecin.
96. A compound of claim 90 in which D is camptothecin.
97. A compound of claim 91 in which D is camptothecin.
98. A compound of claim 92 in which D is camptothecin.
99. A compound of claim 93 in which D is camptothecin.
100. A compound of claim 94 in which D is camptothecin.
101. A compound of claim 1 in which D is an aldehyde containing drug.
102. A compound of claim 2 in which D is an aldehyde containing drug.
103. A compound of claim 3 in which D is an aldehyde containing drug.
104. A compound of claim 4 in which D is an aldehyde containing drug.
105. A compound of claim 5 in which D is an aldehyde containing drug.
106. A compound of claim 6 in which D is an aldehyde containing drug.
107. A compound of claim 101 in which D is an anthracycline.
108. A compound of claim 102 in which D is an anthracycline.
109. A compound of claim 103 in which D is an anthracycline.
110. A compound of claim 104 which D is an anthracycline.
111. A compound of claim 105 in which D is an anthracycline.
112. A compound of claim 106 in which D is an anthracycline.
113. A compound of claim 1 in which D is a ketone containing drug.
114. A compound of claim 2 in which D is a ketone containing drug.
115. A compound of claim 3 in which D is a ketone containing drug.
116. A compound of claim 4 in which D is a ketone containing drug.
117. A compound of claim 5 in which D is a ketone containing drug.
118. A compound of claim 6 in which D is a ketone containing drug.
119. A compound of claim 113 in which D is an anthracycline.
120. A compound of claim 114 in which D is an anthracycline.
121. A compound of claim 115 in which D is an anthracycline.
122. A compound of claim 116 in which D is an anthracycline.
123. A compound of claim 117 in which D is an anthracycline.
124. A compound of claim 118 in which D is an anthracycline.
125. A compound of claim 1 in which L is an immunoglobulin, or a fragment thereof.
126. A compound of claim 2 in which L is an immunoglobulin, or a fragment thereof.
127. A compound of claim 3 in which L is an immunoglobulin, or a fragment thereof.
128. A compound of claim 4 in which L is an immunoglobulin, or a fragment thereof.
129. A compound of claim 5 in which L is an immunoglobulin, or a fragment thereof.
130. A compound of claim 6 in which L is an immunoglobulin, or a fragment thereof.
131. A compound of claim 125 in which L is an immunoglobulin selected from the group consisting of BR96, BR64, L6, a reduced BR96, a reduced BR64, a reduced L6, a chimeric BR96, a relaxed chimeric BR64, a chimeric L6, a reduced chimeric BR96, a reduced chimeric BR64, a reduced chimeric L6; and, a fragment thereof.
132. A compound of claim 126 in which L is an immunoglobulin selected from the group consisting of BR96, BR64, L6, a reduced BR96, a reduced BR64, a reduced L6, a chimeric BR96, a relaxed chimeric BR64, a chimeric L6, a reduced chimeric BR96, a reduced chimeric BR64, a reduced chimeric L6; and, a fragment thereof.
133. A compound of claim 127 in which L is an immunoglobulin selected from the group consisting of BR96, BR64, L6, a reduced BR96, a reduced BR64, a reduced L6, a chimeric BR96, a relaxed chimeric BR64, a chimeric L6, a reduced chimeric BR96, a reduced chimeric BR64, a reduced chimeric L6; and, a fragment thereof.
134. A compound of claim 128 in which L is an immunoglobulin selected from the group consisting of BR96, BR64, L6, a reduced BR96, a reduced BR64, a reduced L6, a chimeric BR96, a relaxed chimeric BR64, a chimeric L6, a reduced chimeric BR96, a reduced chimeric BR64, a reduced chimeric L6; and, a fragment thereof.
135. A compound of claim 129 in which L is an immunoglobulin selected from the group consisting of BR96, BR64, L6, a reduced BR96, a reduced BR64, a reduced L6, a chimeric BR96, a relaxed chimeric BR64, a chimeric L6, a reduced chimeric BR96, a reduced chimeric BR64, a reduced chimeric L6; and, a fragment thereof.
136. A compound of claim 130 in which L is an immunoglobulin selected from the group consisting of BR96, BR64, L6, a reduced BR96, a reduced BR64, a reduced L6, a chimeric BR96, a relaxed chimeric BR64, a chimeric L6, a reduced chimeric BR96, a reduced chimeric BR64, a reduced chimeric L6; and, a fragment thereof.
137. A compound of claim 131 in which L is a chimeric BR96, a reduced chimeric BR96; or a fragment thereof.
138. A compound of claim 132 in which L is a chimeric BR96, a reduced chimeric BR96; or a fragment thereof.
139. A compound of claim 133 in which L is a chimeric BR96, a reduced chimeric BR96; or a fragment thereof.
140. A compound of claim 134 in which L is a chimeric BR96, a reduced chimeric BR96; or a fragment thereof.
141. A compound of claim 135 in which L is a chimeric BR96, a reduced chimeric BR96; or a fragment thereof.
142. A compound of claim 136 in which L is a chimeric BR96, a reduced chimeric BR96; or a fragment thereof.
143. A compound of claim 1 in which L is a ligand selected from the group consisting of bombesin, EDG, transferrin, gastrin, gastrin-releasing peptide, platelet-derived growth factor, IL-2, IL-6, TFG-α, TFG-β, VGF, insulin and insulin-like growth factors I and II.

144. A compound of claim 2 in which L is a ligand selected from the group consisting of bombesin, EDG, transferrin, gastrin, gastrin-releasing peptide, platelet-derived growth factor, IL-2, IL-6, TFG-α, TFG-β, VGF, insulin and insulin-like growth factors I and II.

145. A compound of claim 3 in which L is a ligand selected from the group consisting of bombesin, EDG, transferrin, gastrin, gastrin-releasing peptide, platelet-derived growth factor, IL-2, IL-6, TFG-α, TFG-β, VGF, insulin and insulin-like growth factors I and II.

146. A compound of claim 4 in which L is a ligand selected from the group consisting of bombesin, EDG, transferrin, gastrin, gastrin-releasing peptide, platelet-derived growth factor, IL-2, IL-6, TFG-α, TFG-β, VGF, insulin and insulin-like growth factors I and II.

147. A compound of claim 5 in which L is a ligand selected from the group consisting of bombesin, EDG, transferrin, gastrin, gastrin-releasing peptide, platelet-derived growth factor, IL-2, IL-6, TFG-α, TFG-β, VGF, insulin and insulin-like growth factors I and II.

148. A compound of claim 6 in which L is a ligand selected from the group consisting of bombesin, EDG, transferrin, gastrin, gastrin-releasing peptide, platelet-derived growth factor, IL-2, IL-6, TFG-α, TFG-β, VGF, insulin and insulin-like growth factors I and II.

149. A compound of claim 1 in which L is a ligand selected from the group consisting of carbohydrates, lectins, and apoprotein from low density lipoproteins.

150. A compound of claim 2 in which L is a ligand selected from the group consisting of carbohydrates, lectins, and apoprotein from low density lipoproteins.

151. A compound of claim 3 in which L is a ligand selected from the group consisting of carbohydrates, lectins, and apoprotein from low density lipoproteins.

152. A compound of claim 4 in which L is a ligand selected from the group consisting of carbohydrates, lectins, and apoprotein from low density lipoproteins.

153. A compound of claim 5 in which L is a ligand selected from the group consisting of carbohydrates, lectins, and apoprotein from low density lipoproteins.

154. A compound of claim 6 in which L is a ligand selected from the group consisting of carbohydrates, lectins, and apoprotein from low density lipoproteins.

155. A compound of claim 1 in which X is the compound having the Formula

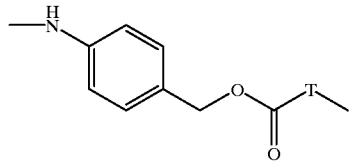

in which T is O, N, or S.

156. A compound of claim 2 in which X is the compound having the Formula

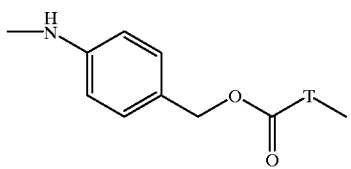

in which T is O, N, or S.

157. A compound of claim 3 in which X is the compound having the Formula

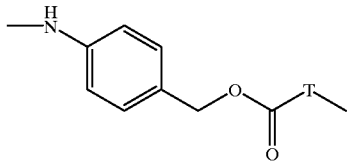

in which T is O, N, or S.

158. A compound of claim 4 in which X is the compound having the Formula

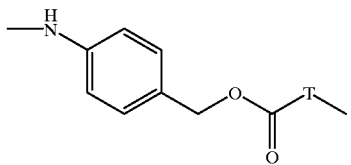

in which T is O, N, or S.

159. A compound of claim 5 in which X is the compound having the Formula

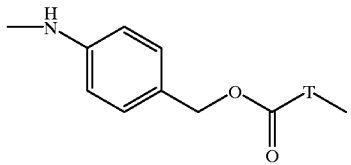

in which T is O, N, or S.

160. A compound of claim 6 in which X is the compound having the Formula

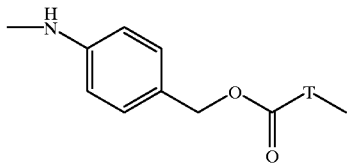

in which T is O, N, or S.

161. A compound of claim 155 in which X is p-aminobenzyl-carbamoyloxy.
162. A compound of claim 156 in which X is p-aminobenzyl-carbamoyloxy.
163. A compound of claim 157 in which X is p-aminobenzyl-carbamoyloxy.
164. A compound of claim 158 in which X is p-aminobenzyl-carbamoyloxy.
165. A compound of claim 159 in which X is p-aminobenzyl-carbamoyloxy.

166. A compound of claim 160 in which X is p-aminobenzyl-carbamoyloxy.

167. A compound of claim 1 in which X is the compound having the Formula

in which $R^1$ is $C_1$–$C_5$ alkyl, T is O, N or S.

168. A compound of claim 2 in which X is the compound having the Formula

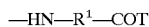

in which $R^1$ is $C_1$–$C_5$ alkyl, T is O, N or S.

169. A compound of claim 3 in which X is the compound having the Formula

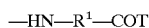

in which $R^1$ is $C_1$–$C_5$ alkyl, T is O, N or S.

170. A compound of claim 4 in which X is the compound having the Formula

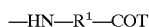

in which $R^1$ is $C_1$–$C_5$ alkyl, T is O, N or S.

171. A compound of claim 5 in which X is the compound having the Formula

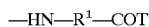

in which $R^1$ is $C_1$–$C_5$ alkyl, T is O, N or S.

172. A compound of claim 6 in which X is the compound having the Formula

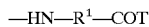

in which $R^1$ is $C_1$–$C_5$ alkyl, T is O, N or S.

173. A compound of claim 167 in which X is γ-aminobutyric acid.
174. A compound of claim 168 in which X is γ-aminobutyric acid.
175. A compound of claim 169 in which X is γ-aminobutyric acid.
176. A compound of claim 170 in which X is γ-aminobutyric acid.
177. A compound of claim 171 in which X is γ-aminobutyric acid.
178. A compound of claim 172 in which X is γ-aminobutyric acid.
179. A compound of claim 167 in which X is α,α-dimethyl γ-aminobutyric acid.
180. A compound of claim 168 in which X is α,α-dimethyl γ-aminobutyric acid.
181. A compound of claim 169 in which X is α,α-dimethyl γ-aminobutyric acid.
182. A compound of claim 170 in which X is α,α-dimethyl γ-aminobutyric acid.
183. A compound of claim 171 in which X is α,α-dimethyl γ-aminobutyric acid.
184. A compound of claim 172 in which X is α,α-dimethyl γ-aminobutyric acid.
185. A compound of claim 167 in which X is β,β-dimethyl γ-aminobutyric acid.
186. A compound of claim 168 in which X is β,β-dimethyl γ-aminobutyric acid.
187. A compound of claim 169 in which X is β,β-dimethyl γ-aminobutyric acid.
188. A compound of claim 170 in which X is β,β-dimethyl γ-aminobutyric acid.
189. A compound of claim 171 in which X is β,β-dimethyl γ-aminobutyric acid.
190. A compound of claim 172 in which X is β,β-dimethyl γ-aminobutyric acid.

191. A compound of claim 1 in which X is the compound having the Formula

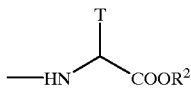

in which T is O, N, or S, $R^2$ is H or $C_1$–$C_5$ alkyl.

192. A compound of claim 2 in which X is the compound having the Formula

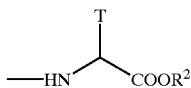

in which T is O, N, or S, $R^2$ is H or $C_1$–$C_5$ alkyl.

193. A compound of claim 3 in which X is the compound having the Formula

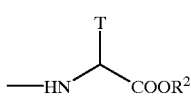

in which T is O, N, or S, $R^2$ is H or $C_1$–$C_5$ alkyl.

194. A compound of claim 4 in which X is the compound having the Formula

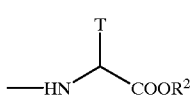

in which T is O, N, or S, $R^2$ is H or $C_1$–$C_5$ alkyl.

195. A compound of claim 5 in which X is the compound having the Formula

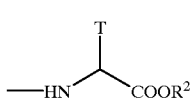

in which T is O, N, or S, $R^2$ is H or $C_1$–$C_5$ alkyl.

196. A compound of claim 6 in which X is the compound having the Formula

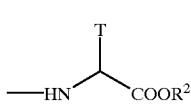

in which T is O, N, or S, $R^2$ is H or $C_1$–$C_5$ alkyl.

197. A compound of claim 1 in which W is

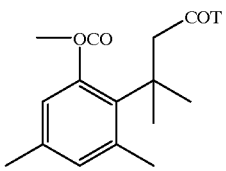

in which T is O, S or N.

198. A compound of claim 2 in which W is

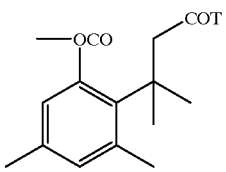

in which T is O, S or N.

199. A compound of claim 3 in which W is

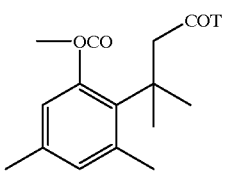

in which T is O, S or N.

200. A compound of claim 4 in which W is

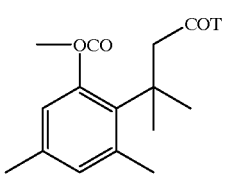

in which T is O, S or N.

201. A compound of claim 5 in which W is

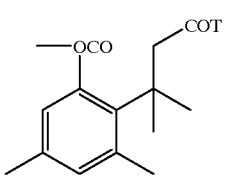

in which T is O, S or N.

202. A compound of claim 6 in which W is

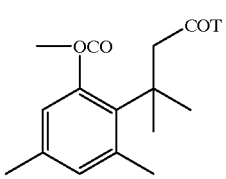

in which T is O, S or N.

203. A compound of claim 1 in which A is

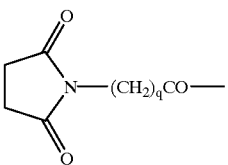

in which q is 1–10.

204. A compound of claim 2 in which A is

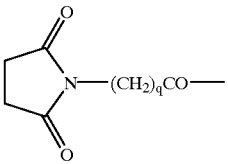

in which q is 1–10.

205. A compound of claim 3 in which A is

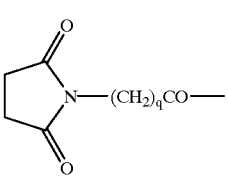

in which q is 1–10.

206. A compound of claim 4 in which A is

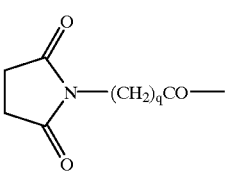

in which q is 1–10.

207. A compound of claim 5 in which A is

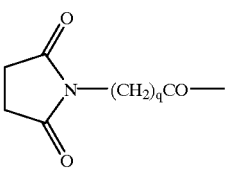

in which q is 1–10.

208. A compound of claim 6 in which A is

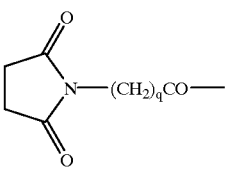

in which q is 1–10.

209. A compound of claim 1 in which A is 4-(N-succinimidomethyl)cyclohexane-1-carbonyl.

210. A compound of claim 2 in which A is 4-(N-succinimidomethyl)cyclohexane-1-carbonyl.

211. A compound of claim 3 in which A is 4-(N-succinimidomethyl)cyclohexane-1-carbonyl.

212. A compound of claim 4 in which A is 4-(N-succinimidomethyl)cyclohexane-1-carbonyl.

213. A compound of claim 5 in which A is 4-(N-succinimidomethyl)cyclohexane-1-carbonyl.

214. A compound of claim 6 in which A is 4-(N-succinimidomethyl)cyclohexane-1-carbonyl.

215. A compound of claim 1 in which A is m-succinimidobenzoyl.

216. A compound of claim 2 in which A is m-succinimidobenzoyl.

217. A compound of claim 3 in which A is m-succinimidobenzoyl.

218. A compound of claim 4 in which A is m-succinimidobenzoyl.

219. A compound of claim 5 in which A is m-succinimidobenzoyl.

220. A compound of claim 6 in which A is m-succinimidobenzoyl.

221. A compound of claim 1 in which A is 4-(p-succinimidophenyl)butyryl.

222. A compound of claim 2 in which A is 4-(p-succinimidophenyl)butyryl.

223. A compound of claim 3 in which A is 4-(p-succinimidophenyl)butyryl.

224. A compound of claim 4 in which A is 4-(p-succinimidophenyl)butyryl.

225. A compound of claim 5 in which A is 4-(p-succinimidophenyl)butyryl.

226. A compound of claim 6 in which A is 4-(p-succinimidophenyl)butyryl.

227. A compound of claim 1 in which A is 4-(2-acetamido)benzoyl.

228. A compound of claim 2 in which A is 4-(2-acetamido)benzoyl.

229. A compound of claim 3 in which A is 4-(2-acetamido)benzoyl.

230. A compound of claim 4 in which A is 4-(2-acetamido)benzoyl.

231. A compound of claim 5 in which A is 4-(2-acetamido)benzoyl.

232. A compound of claim 6 in which A is 4-(2-acetamido)benzoyl.

233. A compound of claim 1 in which A is 3-thiopropionyl.

234. A compound of claim 2 in which A is 3-thiopropionyl.

235. A compound of claim 3 in which A is 3-thiopropionyl.

236. A compound of claim 4 in which A is 3-thiopropionyl.

237. A compound of claim 5 in which A is 3-thiopropionyl.

238. A compound of claim 6 in which A is 3-thiopropionyl.

239. A compound of claim 1 in which A is 4-(1-thioethyl)-benzoyl.

240. A compound of claim 2 in which A is 4-(1-thioethyl)-benzoyl.

241. A compound of claim 3 in which A is 4-(1-thioethyl)-benzoyl.

242. A compound of claim 4 in which A is 4-(1-thioethyl)-benzoyl.

243. A compound of claim 5 in which A is 4-(1-thioethyl)-benzoyl.

244. A compound of claim 6 in which A is 4-(1-thioethyl)-benzoyl.

245. A compound of claim 1 in which A is 6-(3-thiopropionylamido)-hexanoyl.

246. A compound of claim 2 in which A is 6-(3-thiopropionylamido)-hexanoyl.

247. A compound of claim 3 in which A is 6-(3-thiopropionylamido)-hexanoyl.

248. A compound of claim 4 in which A is 6-(3-thiopropionylamido)-hexanoyl.

249. A compound of claim 5 in which A is 6-(3-thiopropionylamido)-hexanoyl.

250. A compound of claim 6 in which A is 6-(3-thiopropionylamido)-hexanoyl.

251. A compound of claim 1 which is BR96-succinimidocaproyl-phenylalanine-lysine-p-aminobenzyl-carbamoyloxy-doxrubicin.

252. A compound of claim 1 which is BR96-succinimidocaproyl-valine-lysine-p-aminobenzyl-carbamoyloxy-doxorubicin.

253. A compound of claim 1 which is BR96-succinimidocaproyl-valine-citrulline-p-aminobenzyl-carbamoyloxy-doxorubicin.

254. A compound of claim 1 which is BR96-succinimidocaproyl-phenylalanine-lysine-p-aminobenzyl-carbamoyloxy-2'-taxol.

255. A compound of claim 1 which is BR96-succinimidocaproyl-phenylalanine-lysine-p-aminobenzyl-carbamoyloxy-7-taxol.

256. A compound of claim 1 which is BR96-succinimidocaproyl-phenylalanine-lysine-p-aminobenzyl-carbamoyloxy-mitomycin-C.

257. A compound of claim 1 which is BR96-succinimidocaproyl-phenylalanine-lysine-gamma-aminobutyric acid-mitomycin-C.

258. A pharmaceutical composition comprising a therapeutically effective amount of a compound of claim 1 and a pharmaceutically acceptable carrier.

* * * * *